US010626101B2

(12) United States Patent
Li et al.

(10) Patent No.: US 10,626,101 B2
(45) Date of Patent: Apr. 21, 2020

(54) SOLID FORMS OF 2-(4-CHLOROPHENYL)-N-((2-(2,6-DIOXOPIPERIDIN-3-YL)-1-OXOISOINDOLIN-5-YL)METHYL)-2,2-DIFLUOROACETAMIDE, AND THEIR PHARMACEUTICAL COMPOSITIONS AND USES

(71) Applicant: Celgene Corporation, Summit, NJ (US)

(72) Inventors: Ying Li, Millburn, NJ (US); Hon-Wah Man, Princeton, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 16/216,914

(22) Filed: Dec. 11, 2018

(65) Prior Publication Data

US 2019/0106405 A1    Apr. 11, 2019

Related U.S. Application Data

(62) Division of application No. 15/400,630, filed on Jan. 6, 2017, now Pat. No. 10,189,808.

(60) Provisional application No. 62/276,750, filed on Jan. 8, 2016.

(51) Int. Cl.
| | |
|---|---|
| *C07D 401/04* | (2006.01) |
| *A61K 9/00* | (2006.01) |
| *A61K 45/06* | (2006.01) |
| *A61K 9/08* | (2006.01) |
| *A61K 9/19* | (2006.01) |
| *A61K 31/513* | (2006.01) |
| *A61K 31/454* | (2006.01) |
| *A61K 39/395* | (2006.01) |
| *C07K 16/00* | (2006.01) |
| *A61K 39/00* | (2006.01) |

(52) U.S. Cl.
CPC .......... *C07D 401/04* (2013.01); *A61K 9/0014* (2013.01); *A61K 9/0019* (2013.01); *A61K 9/08* (2013.01); *A61K 9/19* (2013.01); *A61K 31/454* (2013.01); *A61K 31/513* (2013.01); *A61K 39/395* (2013.01); *A61K 45/06* (2013.01); *C07K 16/00* (2013.01); *A61K 2039/505* (2013.01); *C07B 2200/13* (2013.01)

(58) Field of Classification Search
CPC .................................................. C07D 401/04
USPC ........................................... 546/200; 514/323
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,044,126 A | 8/1977 | Cook et al. | |
| 4,364,923 A | 12/1982 | Cook et al. | |
| 4,414,209 A | 11/1983 | Cook et al. | |
| 4,522,811 A | 6/1985 | Eppstein et al. | |
| 4,810,643 A | 3/1989 | Souza | |
| 4,994,443 A | 2/1991 | Folkman et al. | |
| 4,999,291 A | 3/1991 | Souza | |
| 5,001,116 A | 3/1991 | Folkman et al. | |
| 5,033,252 A | 7/1991 | Carter | |
| 5,052,558 A | 10/1991 | Carter | |
| 5,059,595 A | 10/1991 | Le Grazie | |
| 5,073,543 A | 12/1991 | Marshall et al. | |
| 5,120,548 A | 6/1992 | McClelland et al. | |
| 5,229,496 A | 7/1993 | Deeley et al. | |
| 5,323,907 A | 6/1994 | Kalvelage | |
| 5,354,556 A | 10/1994 | Sparks et al. | |
| 5,391,485 A | 2/1995 | Deeley et al. | |
| 5,393,870 A | 2/1995 | Deeley et al. | |
| 5,528,823 A | 6/1996 | Rudy, Jr. et al. | |
| 5,580,755 A | 12/1996 | Souza | |
| 5,591,767 A | 1/1997 | Mohr et al. | |
| 5,639,476 A | 6/1997 | Oshlack et al. | |
| 5,639,480 A | 6/1997 | Bodmer et al. | |
| 5,674,533 A | 10/1997 | Santus et al. | |
| 5,709,874 A | 1/1998 | Hanson et al. | |
| 5,733,566 A | 3/1998 | Lewis | |
| 5,739,108 A | 4/1998 | Mitchell | |
| 5,759,542 A | 6/1998 | Gurewich | |
| 5,811,097 A | 9/1998 | Allison | |
| 5,840,674 A | 11/1998 | Yatvin et al. | |
| 5,855,887 A | 1/1999 | Allison et al. | |
| 5,891,474 A | 4/1999 | Busetti et al. | |
| 5,900,252 A | 5/1999 | Calanchi et al. | |
| 5,922,356 A | 7/1999 | Koseki et al. | |
| 5,948,893 A | 9/1999 | June et al. | |
| 5,972,366 A | 10/1999 | Haynes et al. | |
| 5,972,891 A | 10/1999 | Kamei et al. | |
| 5,980,945 A | 11/1999 | Ruiz | |
| 5,985,307 A | 11/1999 | Hanson et al. | |

(Continued)

FOREIGN PATENT DOCUMENTS

| | | |
|---|---|---|
| WO | WO 2003/042402 A2 | 5/2003 |
| WO | WO 2008/156712 A1 | 12/2008 |

(Continued)

OTHER PUBLICATIONS

Anguille et al., "Leukemia-associated antigens and their relevance to the immunotherapy of acute myeloid leukemia," *Leukemia*, 26(10):2186-2196 (2012).

(Continued)

*Primary Examiner* — Patricia L Morris
(74) *Attorney, Agent, or Firm* — Jones Day

(57) ABSTRACT

Solid forms comprising 2-(4-chlorophenyl)-N-((2-(2,6-dioxopiperidin-3-yl)-1-oxoisoindolin-5-yl)methyl)-2,2-difluoroacetamide, compositions comprising the solid forms, methods of making the solid forms and methods of their uses are disclosed.

10 Claims, 29 Drawing Sheets

(56) References Cited

U.S. PATENT DOCUMENTS

| | | | |
|---|---|---|---|
| 5,993,855 A | 11/1999 | Yoshimoto et al. |
| 6,004,534 A | 12/1999 | Langer et al. |
| 6,039,975 A | 3/2000 | Shah et al. |
| 6,045,830 A | 4/2000 | Igari |
| 6,048,736 A | 4/2000 | Kosak |
| 6,051,227 A | 4/2000 | Allison et al. |
| 6,060,082 A | 5/2000 | Chen et al. |
| 6,071,495 A | 6/2000 | Unger et al. |
| 6,087,324 A | 7/2000 | Igari et al. |
| 6,113,943 A | 9/2000 | Okada et al. |
| 6,120,751 A | 9/2000 | Unger |
| 6,131,570 A | 10/2000 | Schuster et al. |
| 6,139,865 A | 10/2000 | Friend et al. |
| 6,197,350 B1 | 3/2001 | Yamagata et al. |
| 6,207,157 B1 | 3/2001 | Gu et al. |
| 6,248,363 B1 | 6/2001 | Patel et al. |
| 6,264,970 B1 | 7/2001 | Hata et al. |
| 6,267,981 B1 | 7/2001 | Okamoto et al. |
| 6,271,359 B1 | 8/2001 | Norris et al. |
| 6,274,552 B1 | 8/2001 | Tamarkin et al. |
| 6,316,652 B1 | 11/2001 | Steliou |
| 6,352,694 B1 | 3/2002 | June et al. |
| 6,376,461 B1 | 4/2002 | Igari et al. |
| 6,419,961 B1 | 7/2002 | Igari et al. |
| 6,613,358 B2 | 2/2003 | Randolph et al. |
| 6,534,055 B1 | 3/2003 | June et al. |
| 6,589,548 B1 | 7/2003 | Oh et al. |
| 6,627,646 B2 | 9/2003 | Bakale et al. |
| 6,682,736 B1 | 1/2004 | Hanson et al. |
| 6,692,964 B1 | 2/2004 | June et al. |
| 6,699,500 B2 | 3/2004 | Okada et al. |
| 6,740,634 B1 | 5/2004 | Saikawa et al. |
| 6,887,466 B2 | 5/2005 | June et al. |
| 6,905,681 B1 | 6/2005 | June et al. |
| 6,984,720 B1 | 1/2006 | Korman et al. |
| 7,488,802 B2 | 2/2009 | Collins et al. |
| 7,498,171 B2 | 3/2009 | Hariri et al. |
| 7,605,238 B2 | 10/2009 | Korman et al. |
| 7,943,743 B2 | 5/2011 | Korman et al. |
| 8,008,449 B2 | 8/2011 | Korman et al. |
| 8,168,757 B2 | 5/2012 | Finnefrock et al. |
| 8,217,149 B2 | 7/2012 | Irving et al. |
| 9,499,514 B2 | 11/2016 | Hansen et al. |
| 2012/0122865 A1 | 5/2012 | Muller et al. |
| 2012/0252844 A1 | 10/2012 | Dewitt |
| 2014/0328832 A1 | 11/2014 | Chopra et al. |

FOREIGN PATENT DOCUMENTS

| | | |
|---|---|---|
| WO | WO 2009/145899 A1 | 12/2009 |
| WO | WO 2010/036959 A2 | 4/2010 |
| WO | WO 2010/053732 A1 | 5/2010 |
| WO | WO 2010/089411 A2 | 8/2010 |
| WO | WO 2011/066342 A2 | 6/2011 |
| WO | WO 2011/082400 A2 | 7/2011 |
| WO | WO 2011/159877 A2 | 12/2011 |
| WO | WO 2011/161699 A2 | 12/2011 |
| WO | WO 2016/007848 A1 | 1/2016 |

OTHER PUBLICATIONS

Bernstein, "Crystal structure prediction and polymorphism," *ACA Transactions*, 39:14-23 (2004).
Bernstein, in *Polymorphism in Moleclar Crystals*, pp. 115-118, 272 (2002).
Braga et al., "Making crystals from crystals: a green route to crystal engineering and polymorphism," *Chem. Commun.*, 7(29):3635-3645 (2005).
Brignone et al., "A soluble form of lymphocyte activation gene-3 (IMP321) induces activation of a large range of human effector cytotoxic cells," *J. Immunol.*, 179(6):4202-4211 (2007).
Buchwald et al., "Long-term, continuous intravenous heparin administration by an implantable infusion pump in ambulatory patients with recurrent venous thrombosis," *Surgery*, 88:507-516 (1980).
Carstensen, *Drug Stability: Principles & Practices*, Second Edition, Marcel Dekker, New York, NY, pp. 379-380 (1995).
Chemburkar et al., "Dealing with the impact of ritonavir polymorphs on the late stages of bulk drug process development," *Org. Proc. Res. Dev.*, 4:413-417 (2000).
*Concise Encyclopedia Chemistry*, Walter de Gruyter, New York, pp. 872-873 (1993).
Davidovich et al., "Dection of polymorphism by powder x-ray diffraction: interference by preferred orientation," *Am. Pharm. Rev.*, 7(1):10, 12, 14, 16, 100 (2004).
Dean, "Analytical Chemistry Handbook," McGraw-Hill Inc., pp. 10.24-10.26. (1995).
Doelker, "Crystalline modifications and polymorphous changes during drug manufacture," *Ann. Pharm. Fr.*, 60:161-176 (2002). English translation.
Doelker, "Physiochemical behaviors of active substances their consequences for the feasibility and the stability of pharmaceutical forms," *S.T.P. Pharma Pratiques*, 9(5):399-409 (1999). English translation.
Emens et al., "Chemotherapy: friend of foe to cancer vaccines," *Curr. Opin. Mol. Ther.*, 3(1):77-84 (2001).
Folkman et al., "Angiogenesis inhibition and tumor regression caused by heparin or a heparin fragment in the presence of cortisone," *Science*, 221:719-725 (1983).
Foster, "Deuterium isotope effects in the metabolism of drugs and xenobiotics: implications for drug design," *Adv. Drug Res.*, 14:1-40 (1985).
Fourcade et al., "Upregulation of Tim-3 and PD-1 expression is associated with tumor antigen-specific CD8+ T cell dysfunction in melanoma patients," *J. Exp. Med.*, 207(10):2175-2186 (2010).
Gatley et al., "Deuterioglucose: alteration of biodistribution by an isotope effect," *J. Nucl. Med.*, 27(3):388-394 (1986).
Goodson, "Medical Applications of Controlled Release," vol. 2, CRC Press, Inc., Boca Raton, FL, pp. 115-138 (1984).
Gordon et al., "The metabolism of the abortifacient terpene, (R)-(+)-pulegone, to a proximate toxin, menthofuran," *Drug Metab. Dispos.*, 15(5):589-594 (1987).
Guillory "Polymorphism in Pharmaceutical Solids," Brittain ed., NY: Marcel Dekker, Inc., 1-2:183-226 (1999).
Ivanisevic et al., "Uses of X-ray powder diffraction in the pharmaceutical industry," *Pharm. Sci. Encycl: Drug Disc. Dev. Manufacturing*, p. 1-42 (2010).
Jain et al., "Polymorphism in Pharmacy," *Indian Drugs*, 23(6):315-329 (1986).
Jones et al., "Pharmaceutical cocrystals: an emerging approach to physical property enhancement," *MRS Bulletin*, 31:875-879 (2006).
Kirk-Othmer, "Cyrstallization," in *Kirk-Othmer Encyclopedia of Chemical Technology*, John Wiley & Sons, Inc., 8:95-147. (Year: 2002).
Kushner et al., "Pharmacological uses and perspectives of heavy water and deuterated compounds," *Can. J. Physiol. Pharmacol*, 77(2):79-88 (1999).
Lijinsky et al., "Dose-response studies in carcinogenesis by nitroso-N-methyl-N-(2-phenyl)ethylamine in rats and the effects of deuterium substitution," *Food Chem. Toxicol.*, 20(4);393-399 (1982).
Lijinsky et al., "Dose-response studies with nitrosoheptamethyleneimine and its alpha-deuterium-labeled derivative in F344 rats," *J. Natl. Cancer Instit.*, 69(5):1127-1133 (1982).
Mangold et al., "Effects of deuterium labeling on azido amino acid mutagenicity in *Salmonella typhimurium*," Mutat. Res., 308(1):33-42 (1994).
Mellon, "CMU seed fund project on detection and control of pharmaceutical polymorphism," The Department of Physics. Retrieved from the internet http://andrew.cmu.edu/user/suter/polymorph.html, retrieved onlin Apr. 3, 2008, 3 pages. (2002).
Muzaffar et al., "Polymorphism and drug availability," *J. Pharm.*, 1(1):59-66 (1979).
Oncology Tools, Dose Calculator and Dose Calculator Results, U.S. Food and Drug Administration, Center for Drug Evaluation and Research (2008), retrieved on the internet URL:https://web.archive.org/web/20080223150428/http://www.fda.gov/cder/cancer/animalframe.htm, retrieved on Jan. 24, 2017, 1 page.

(56) References Cited

OTHER PUBLICATIONS

Otuska et al., "Effect of polymorphic forms of bulk powders of pharmaceutical properties, of carbamazepine granules," *Chem. Pharm. Bull.*, 47(6):852-856 (1999).
Pardoll, "The blockade of immune checkpoints in cancer immunotherapy," *Nat. Rev. Cancer,* 12(4):252-264 (2012).
Penichet et al., "Antibody-cytokine fusion proteins for the therapy of cancer," *J. Immunol. Methods,* 284:91-101 (2001).
Price, "The computational prediction of pharmaceutical crystal structures and polymorphism," *Adv. Drug Deliv. Rev.,* 56(3):301-309 (2004).
Rodriguez-Spong et al., "General principles of pharmaceutical solid polymorphism: a supramolecular perspective," *Adv. Drug Del. Rev.,* 56:241-274 (2004).
Roitt et al., Immunology, Third Edition, Mosby, St. Louis, MO, 17.1-17.12 (1993).
Sakuishi et al., "Targeting Tim-3 and PD-1 pathways to reverse T cell exhaustion and restore anti-tumor immunity," *J. Exp. Med.,* 207(10):2187-2194 (2010).
Saudek et al., "A preliminary trial of the programmable implantable medication system for insulin delivery," *N. Engl. J. Med.,* 321(9):574-579 (1989).
Seddon, "Pseudopolymorph: a polemic," *Crystal Growth & Design,* 4(6):1087 (2 pages from internet) (2004).
Sefton, "Implantable pumps," Crit. Rev. Biomed. Eng., 14(3):201-240 (1987).
Serajuddin et al., "Selection of solid dosage form composition through drug-excipient compatibility testing," *J. Pharm. Sci.,* 88(7):696-704 (1999).
Singhal et al., "Drug polymorphism and dosage form design: a practical perspective," *Adv. Drug Del. Rev.,* 56:335-347 (2004).
Stockdale, Medicine, vol. 3, Rubenstein and Federman, eds., Chapter 12, Section IV and Section X (1998).
Straathof et al., "An inducible caspase 9 safety switch for T-cell therapy," *Blood,* 105(11):4247-4254 (2005).
Taday et al., "Using terahertz pulse spectoscopy to study the crystalline structure of a druf: a case study of the polymorphs of ranitidine hydrochloride," *J. Pharm. Sci.,* 92(4):831-838 (2003).
Taylor et al., "Protamine is an inhibitor of angiogenesis," *Nature,* 297:307-312 (1982).
The United States Pharmacopeia, $23^{rd}$ Edition, United States Pharmacopeial Convention, Inc., Rockville, MD, pp. 1843-1844 (1995).
The United States Pharmacopeia, $26^{th}$ Edition, United States Pharmacopeial Convention, Inc., Rockville, MD, p. 2228 (2003).
Therasse et al., "New guidelines to evaluate the response to treatment in solid tumors. European Organization for Research and Treatment of Cancer, National Cancer Institute of the United States, National Cancer Institute of Canada," *J. Natl. Cancer Inst.,* 92(3):205-216 (2000).
U.S. Pharmacopia #23, National Formulary #18, pp. 1843-1844 (1995).
Vippagunta et al., "Crystalline solids," *Adv. Drug Deliv. Rev.,*48(1):3-26 (2001).
Wade, "Deuterium isotope effects on noncovalent interactions between molecules," *Chem. Biol. Interact.,* 117:191-217 (1999).
Yu, "Amorphous pharmaceutical solids: preparation, characterization and stabilization," *Adv. Drug Deliv. Rev.,* 48(1):27-42 (2001).
Zello et al., "Plasma and urine enrichments following infusion of L[1-13C]phenylalanine and L-[ring-2H5]phenylalanine in humans: evidence for an isotope effect in renal tubular reabsorption,"*Metabolism,* 43(4):487-491 (1994).
United States Patent and Trademark Office, Office Action in U.S. Appl. No. 15/400,630, dated Jan. 18, 2018 (18 pages).
United States Patent and Trademark Office, final Office Action in U.S. Appl. No. 15/400,630, dated Jun. 28, 2018 (9 pages).
United States Patent and Trademark Office, Notice of Allowance in U.S. Appl. No. 15/400,630, dated Sep. 12, 2018 (6 pages).

SOLID FORMS OF 2-(4-CHLOROPHENYL)-N-((2-(2,6-DIOXOPIPERIDIN-3-YL)-1-OXOISOINDOLIN-5-YL)METHYL)-2,2-DIFLUOROACETAMIDE, AND THEIR PHARMACEUTICAL COMPOSITIONS AND USES

1. CROSS REFERENCE TO RELATED APPLICATIONS

This application is a divisional of U.S. application Ser. No. 15/400,630 filed Jan. 6, 2017, currently allowed, which claims the benefit of the priority of U.S. Provisional Application No. 62/276,750, filed Jan. 8, 2016, the disclosures of each of which are incorporated herein by reference in their entireties.

2. FIELD

Provided herein are solid forms of 2-(4-chlorophenyl)-N-((2-(2,6-dioxopiperidin-3-yl)-1-oxoisoindolin-5-yl)methyl)-2,2-difluoroacetamide, pharmaceutical compositions thereof, and methods of their uses for the treatment of diseases or disorders.

3. BACKGROUND OF THE DISCLOSURE

3.1 Pathobiology of Cancer and Other Diseases

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J and Kale, D., *Immunology*, 17.1-17.12 (3rd ed., Mosby, St. Louis, Mo., 1993).

There is an enormous variety of cancers which are described in detail in the medical literature. Examples include cancers of the lung, colon, rectum, prostate, breast, brain, and intestine. The incidence of cancer continues to climb as the general population ages, as new cancers develop, and as susceptible populations (e.g., people infected with AIDS or excessively exposed to sunlight) grow. However, options for the treatment of cancer are limited. For example, in the case of blood cancers (e.g., multiple myeloma), few treatment options are available, especially when conventional chemotherapy fails and bone-marrow transplantation is not an option. A tremendous demand therefore exists for new methods and compositions that can be used to treat patients with cancer.

Many types of cancers are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties. Examples of these cytokines include acidic and basic fibroblastic growth factor (a,b-FGF), angiogenin, vascular endothelial growth factor (VEGF), and TNF-α. Alternatively, tumor cells can release angiogenic peptides through the production of proteases and the subsequent breakdown of the extracellular matrix where some cytokines are stored (e.g., b-FGF). Angiogenesis can also be induced indirectly through the recruitment of inflammatory cells (particularly macrophages) and their subsequent release of angiogenic cytokines (e.g., TNF-α, b-FGF).

A variety of other diseases and disorders are also associated with, or characterized by, undesired angiogenesis. For example, enhanced or unregulated angiogenesis has been implicated in a number of diseases and medical conditions including, but not limited to, ocular neovascular diseases, choroidal neovascular diseases, retina neovascular diseases, rubeosis (neovascularization of the angle), viral diseases, genetic diseases, inflammatory diseases, allergic diseases, and autoimmune diseases. Examples of such diseases and conditions include, but are not limited to, diabetic retinopathy, retinopathy of prematurity, corneal graft rejection, neovascular glaucoma, retrolental fibroplasia, arthritis, and proliferative vitreoretinopathy.

Accordingly, compounds that can control angiogenesis or inhibit the production of certain cytokines, including TNFα, may be useful in the treatment and prevention of various diseases and conditions.

3.2 Methods of Treating Cancer

Current cancer therapy may involve surgery, chemotherapy, hormonal therapy and/or radiation treatment to eradicate neoplastic cells in a patient (see, e.g., Stockdale, 1998, *Medicine*, vol. 3, Rubenstein and Federman, eds., Chapter 12, Section IV). Recently, cancer therapy could also involve biological therapy or immunotherapy. All of these approaches pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells. Biological therapies and immunotherapies are limited in number and may produce side effects such as rashes or swellings, flu-like symptoms, including fever, chills and fatigue, digestive tract problems or allergic reactions.

With respect to chemotherapy, there is a variety of chemotherapeutic agents available for treatment of cancer. A majority of cancer chemotherapeutics act by inhibiting DNA synthesis, either directly or indirectly by inhibiting the biosynthesis of deoxyribonucleotide triphosphate precursors, to prevent DNA replication and concomitant cell division. Gilman et al., Goodman and Gilman's: *The Pharmacological Basis of Therapeutics*, Tenth Ed. (McGraw Hill, New York).

Despite availability of a variety of chemotherapeutic agents, chemotherapy has many drawbacks. Stockdale, *Medicine*, vol. 3, Rubenstein and Federman, eds., ch. 12, sect. 10, 1998. Almost all chemotherapeutic agents are toxic, and chemotherapy causes significant, and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as pleiotropic drug or multidrug resistance. Because of the drug resistance, many cancers prove or become refractory to standard chemotherapeutic treatment protocols.

Other diseases or conditions associated with, or characterized by, undesired angiogenesis are also difficult to treat. However, some compounds such as protamine, hepain and steroids have been proposed to be useful in the treatment of certain specific diseases. Taylor et al., *Nature* 297:307 (1982); Folkman et al., *Science* 221:719 (1983); and U.S. Pat. Nos. 5,001,116 and 4,994,443.

Still, there is a significant need for safe and effective methods of treating, preventing and managing cancer and other diseases and conditions, including for diseases that are refractory to standard treatments, such as surgery, radiation therapy, chemotherapy and hormonal therapy, while reducing or avoiding the toxicities and/or side effects associated with the conventional therapies.

3.3 Solid Forms

The preparation and selection of a solid form of a pharmaceutical compound is complex, given that a change in solid form may affect a variety of physical and chemical properties, which may provide benefits or drawbacks in processing, formulation, stability and bioavailability, among other important pharmaceutical characteristics. Potential pharmaceutical solids include crystalline solids and amorphous solids. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (see, e.g., S. R. Vippagunta et al., *Adv. Drug. Deliv. Rev.*, (2001) 48:3-26; L. Yu, *Adv. Drug. Deliv. Rev.*, (2001) 48:27-42).

Whether crystalline or amorphous, potential solid forms of a pharmaceutical compound include single-component and multiple-component solids. Single-component solids consist essentially of the pharmaceutical compound in the absence of other compounds. Variety among single-component crystalline materials may potentially arise, e.g., from the phenomenon of polymorphism, wherein multiple three-dimensional arrangements exist for a particular pharmaceutical compound (see, e.g., S. R. Byrn et al., Solid State Chemistry of Drugs, (1999) SSCI, West Lafayette). The importance of studying polymorphs was underscored by the case of Ritonavir, an HIV protease inhibitor that was formulated as soft gelatin capsules. About two years after the product was launched, the unanticipated precipitation of a new, less soluble polymorph in the formulation necessitated the withdrawal of the product from the market until a more consistent formulation could be developed (see S. R. Chemburkar et al., *Org. Process Res. Dev.*, (2000) 4:413-417).

Additional diversity among the potential solid forms of a pharmaceutical compound may arise, e.g., from the possibility of multiple-component solids. Crystalline solids comprising two or more ionic species may be termed salts (see, e.g., Handbook of Pharmaceutical Salts: Properties, Selection and Use, P. H. Stahl and C. G. Wermuth, Eds., (2002), Wiley, Weinheim). Additional types of multiple-component solids that may potentially offer other property improvements for a pharmaceutical compound or salt thereof include, e.g., hydrates, solvates, co-crystals and clathrates, among others (see, e.g., S. R. Byrn et al., Solid State Chemistry of Drugs, (1999) SSCI, West Lafayette). Moreover, multiple-component crystal forms may potentially be susceptible to polymorphism, wherein a given multiple-component composition may exist in more than one three-dimensional crystalline arrangement. The preparation of solid forms is of great importance in the development of a safe, effective, stable and marketable pharmaceutical compound.

Notably, it is not possible to predict a priori if crystalline forms of a compound even exist, let alone how to successfully prepare them (see, e.g., Braga and Grepioni, 2005, "Making crystals from crystals: a green route to crystal engineering and polymorphism," *Chem. Commun.*: 3635-3645 (with respect to crystal engineering, if instructions are not very precise and/or if other external factors affect the process, the result can be unpredictable); Jones et al., 2006, Pharmaceutical Cocrystals: An Emerging Approach to Physical Property Enhancement," *MRS Bulletin* 31:875-879 (At present it is not generally possible to computationally predict the number of observable polymorphs of even the simplest molecules); Price, 2004, "The computational prediction of pharmaceutical crystal structures and polymorphism," *Advanced Drug Delivery Reviews* 56:301-319 ("Price"); and Bernstein, 2004, "Crystal Structure Prediction and Polymorphism," *ACA Transactions* 39:14-23 (a great deal still needs to be learned and done before one can state with any degree of confidence the ability to predict a crystal structure, much less polymorphic forms)).

The variety of possible solid forms creates potential diversity in physical and chemical properties for a given pharmaceutical compound. The discovery and selection of solid forms are of great importance in the development of an effective, stable and marketable pharmaceutical product.

Citation or identification of any reference in Section 2 of this application is not to be construed as an admission that the reference is prior art to the present application.

Provided herein are solid forms of 2-(4-chlorophenyl)-N-((2-(2,6-dioxopiperidin-3-yl)-1-oxoisoindolin-5-yl)methyl)-2,2-difluoroacetamide ("Compound 1"). Compound 1 was described in U.S. Pat. No. 9,499,514 and International Patent Publication No. WO 2016/007848, the disclosures of each which are incorporated herein by reference in their entireties.

4. SUMMARY

Provided herein are solid forms of 2-(4-chlorophenyl)-N-((2-(2,6-dioxopiperidin-3-yl)-1-oxoisoindolin-5-yl)methyl)-2,2-difluoroacetamide, and tautomers thereof (Compound 1)

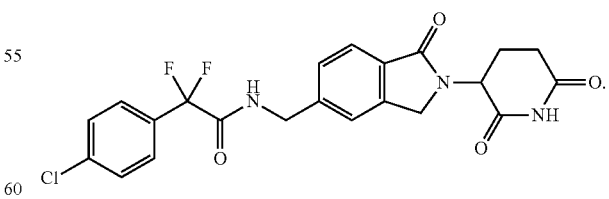

In one embodiment, the solid form is crystalline Form A. In another embodiment, the solid form is crystalline Form B. In yet another embodiment, the solid form is crystalline Form C. In yet another embodiment, the solid form is crystalline Form D. In yet another embodiment, the solid form is crystalline Form E.

Further provided herein is an amorphous form comprising Compound 1.

In certain embodiments, the solid forms are single-component crystal forms of 2-(4-chlorophenyl)-N-((2-(2,6-dioxopiperidin-3-yl)-1-oxoisoindolin-5-yl)methyl)-2,2-difluoroacetamide. In certain embodiments, the solid forms are multiple-component crystal forms of 2-(4-chlorophenyl)-N-((2-(2,6-dioxopiperidin-3-yl)-1-oxoisoindolin-5-yl)methyl)-2,2-difluoroacetamide. In certain embodiments, the solid forms are single-component amorphous forms of 2-(4-chlorophenyl)-N-((2-(2,6-dioxopiperidin-3-yl)-1-oxoisoindolin-5-yl)methyl)-2,2-difluoroacetamide. In certain embodiments, the solid forms are multiple-component amorphous forms of 2-(4-chlorophenyl)-N-((2-(2,6-dioxopiperidin-3-yl)-1-oxoisoindolin-5-yl)methyl)-2,2-difluoroacetamide.

Without intending to be limited by any particular theory, certain solid forms provided herein have particular advantageous physical and/or chemical properties making them useful, e.g., for manufacturing, processing, formulation and/or storage, while also possessing particularly advantageous biological properties, such as, e.g., bioavailability and/or biological activity.

In certain embodiments, solid forms provided herein include solid forms comprising 2-(4-chlorophenyl)-N-((2-(2,6-dioxopiperidin-3-yl)-1-oxoisoindolin-5-yl)methyl)-2,2-difluoroacetamide, including, but not limited to, single-component and multiple-component solid forms comprising 2-(4-chlorophenyl)-N-((2-(2,6-dioxopiperidin-3-yl)-1-oxoisoindolin-5-yl)methyl)-2,2-difluoroacetamide. Certain embodiments herein provide methods of making, isolating and/or characterizing the solid forms provided herein.

Also provided are pharmaceutical compositions formulated for administration by an appropriate route and means containing effective concentrations of a solid form of 2-(4-chlorophenyl)-N-((2-(2,6-dioxopiperidin-3-yl)-1-oxoisoindolin-5-yl)methyl)-2,2-difluoroacetamide, and optionally comprising at least one pharmaceutical carrier.

In one embodiment, the pharmaceutical compositions deliver amounts effective for the treatment of cancer, including solid tumors and blood borne tumors. In one embodiment, the pharmaceutical compositions deliver amounts effective for the prevention of cancer, including solid tumors and blood borne tumors. In one embodiment, the pharmaceutical compositions deliver amounts effective for the amelioration of cancer, including solid tumors and blood borne tumors.

Also provided herein are combination therapies using a solid form of 2-(4-chlorophenyl)-N-((2-(2,6-dioxopiperidin-3-yl)-1-oxoisoindolin-5-yl)methyl)-2,2-difluoroacetamide in combination with a therapy e.g., another pharmaceutical agent with activity against cancer, for example AML, or a myelodysplastic syndrome (MDS), and/or symptoms thereof. Examples of therapies within the scope of the methods include, but are not limited to, surgery, chemotherapy, radiation therapy, hormonal therapy, biological therapy, immunotherapy, and combinations thereof.

The solid form of 2-(4-chlorophenyl)-N-((2-(2,6-dioxopiperidin-3-yl)-1-oxoisoindolin-5-yl)methyl)-2,2-difluoroacetamide provided herein may be administered simultaneously with, prior to, or after administration of one or more of the above therapies. Pharmaceutical compositions containing a solid form of 2-(4-chlorophenyl)-N-((2-(2,6-dioxopiperidin-3-yl)-1-oxoisoindolin-5-yl)methyl)-2,2-difluoroacetamide provided herein and one or more of the above agents are also provided.

In certain embodiments, provided herein are methods of treating, preventing or ameliorating cancer, including solid tumors and blood borne tumors, or one or more symptoms or causes thereof. In certain embodiments, provided herein are methods of preventing cancer, including solid tumors and blood borne tumors, or one or more symptoms or causes thereof. In certain embodiments, provided herein are methods of ameliorating cancer, including solid tumors and blood borne tumors, or one or more symptoms or causes thereof. In certain embodiments, the blood borne tumor is leukemia. In certain embodiments, methods provided herein encompass methods of treating various forms of leukemias such as chronic lymphocytic leukemia, chronic myeloid leukemia, acute lymphocytic leukemia, acute myeloid leukemia and acute myeloblastic leukemia. In certain embodiments, methods provided herein encompass methods of preventing various forms of leukemias such as chronic lymphocytic leukemia, chronic myeloid leukemia, acute lymphocytic leukemia, acute myeloid leukemia and acute myeloblastic leukemia. In certain embodiments, methods provided herein encompass methods of managing various forms of leukemias such as chronic lymphocytic leukemia, chronic myeloid leukemia, acute lymphocytic leukemia, acute myeloid leukemia and acute myeloblastic leukemia. The methods provided herein include treatment of leukemias that are relapsed, refractory or resistant. The methods provided herein include prevention of leukemias that are relapsed, refractory or resistant. The methods provided herein include management of leukemias that are relapsed, refractory or resistant. In one embodiment, methods provided herein encompass methods of treating acute myeloid leukemia. In one embodiment, methods provided herein encompass methods of preventing acute myeloid leukemia. In one embodiment, methods provided herein encompass methods of managing acute myeloid leukemia.

In certain embodiments, provided herein are methods of treating, preventing or ameliorating a myelodysplastic syndrome, or one or more symptoms or causes thereof. In certain embodiments, provided herein are methods of preventing cancer, including a myelodysplastic syndrome, or one or more symptoms or causes thereof. In certain embodiments, provided herein are methods of ameliorating a myelodysplastic syndrome, or one or more symptoms or causes thereof.

In one embodiment, provided herein are methods of treating acute myeloid leukemia by intravenous administration of a composition comprising solid form of 2-(4-chlorophenyl)-N-((2-(2,6-dioxopiperidin-3-yl)-1-oxoisoindolin-5-yl)methyl)-2,2-difluoroacetamide or and tautomers thereof.

In one embodiment, provided herein are methods of treating a myelodysplastic syndrome by intravenous administration of a composition comprising solid form of 2-(4-chlorophenyl)-N-((2-(2,6-dioxopiperidin-3-yl)-1-oxoisoindolin-5-yl)methyl)-2,2-difluoroacetamide or and tautomers thereof.

In practicing the methods, effective amounts of a solid form of 2-(4-chlorophenyl)-N-((2-(2,6-dioxopiperidin-3-yl)-1-oxoisoindolin-5-yl)methyl)-2,2-difluoroacetamide or compositions containing therapeutically effective concentrations of the solid form of 2-(4-chlorophenyl)-N-((2-(2,6-dioxopiperidin-3-yl)-1-oxoisoindolin-5-yl)methyl)-2,2-difluoroacetamide are administered to an individual exhibiting the symptoms of the disease or disorder to be treated. The amounts are effective to ameliorate or eliminate one or more symptoms of the disease or disorder.

Further provided is a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like.

These and other aspects of the subject matter described herein will become evident upon reference to the following detailed description.

5. BRIEF DESCRIPTION OF THE FIGURES

Figure 6:
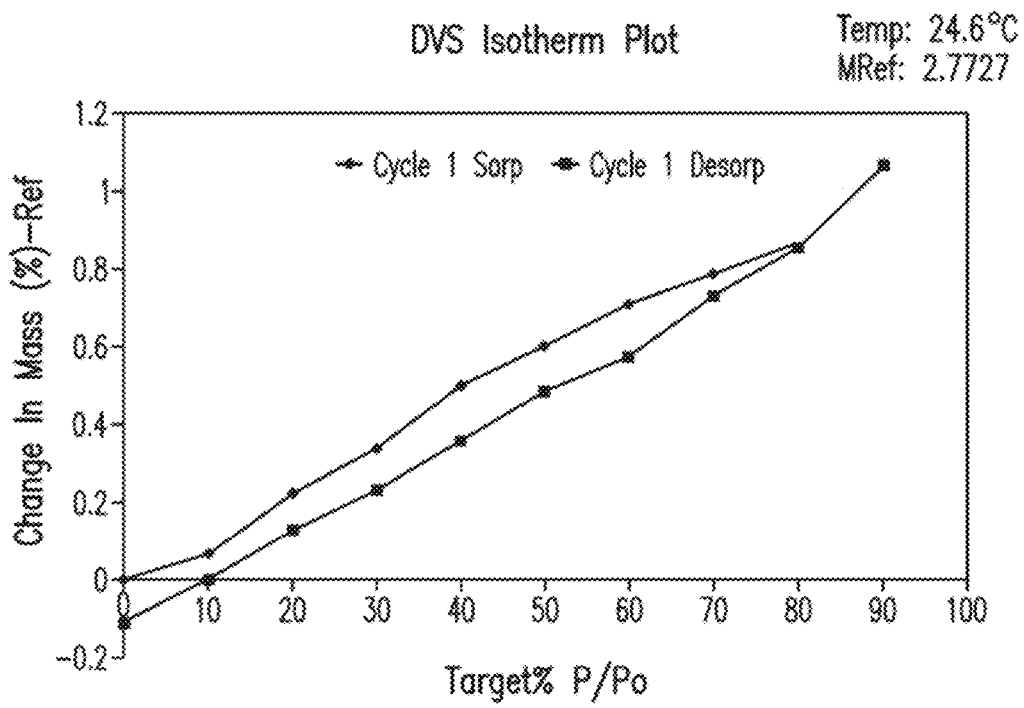

FIG. 6 provides a dynamic vapor sorption (DVS) isotherm plot of Form A of Compound 1.

Figure 7:
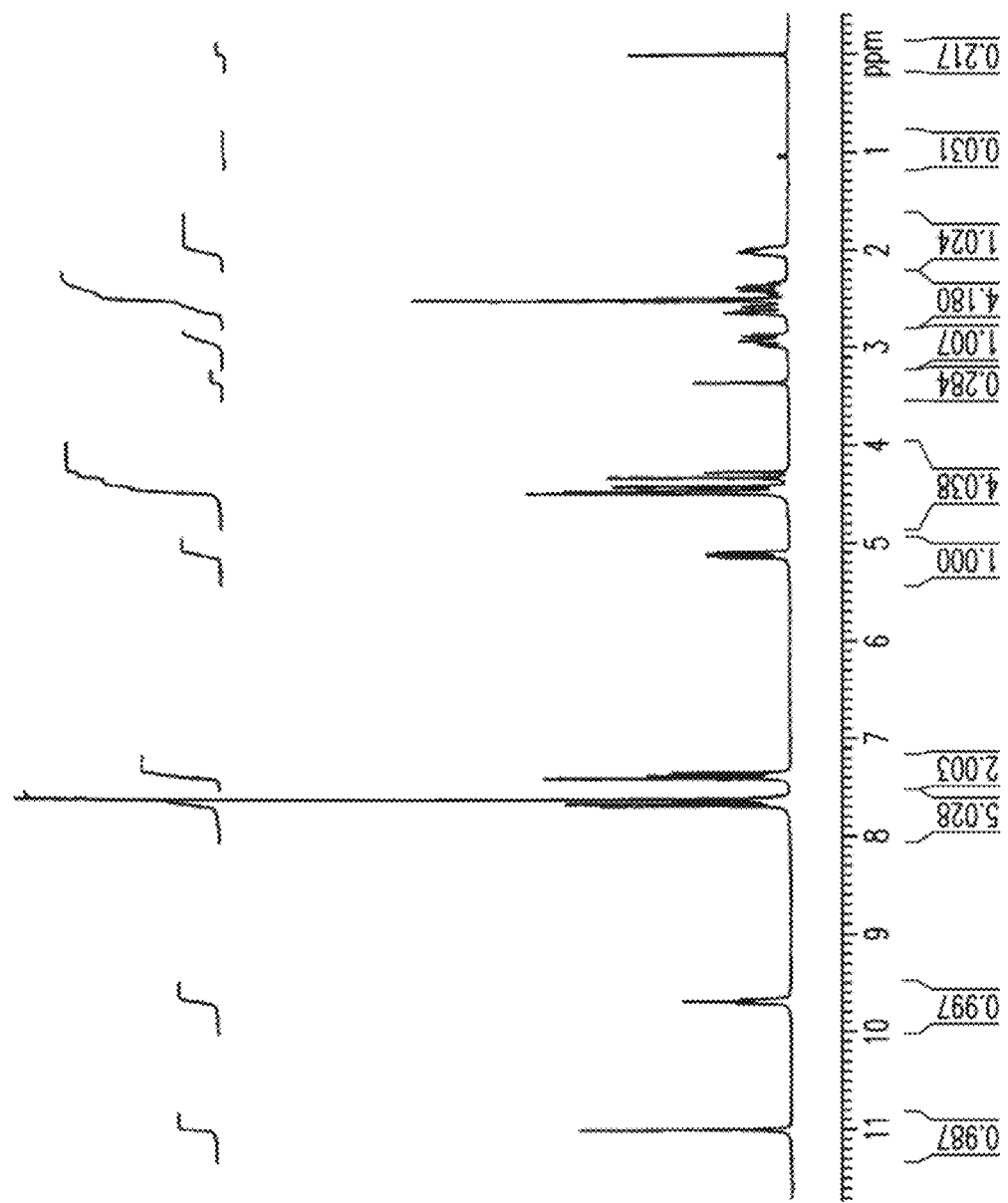

FIG. 7 provides a $^1$H NMR spectrum of Form A of Compound 1.

Figure 8:
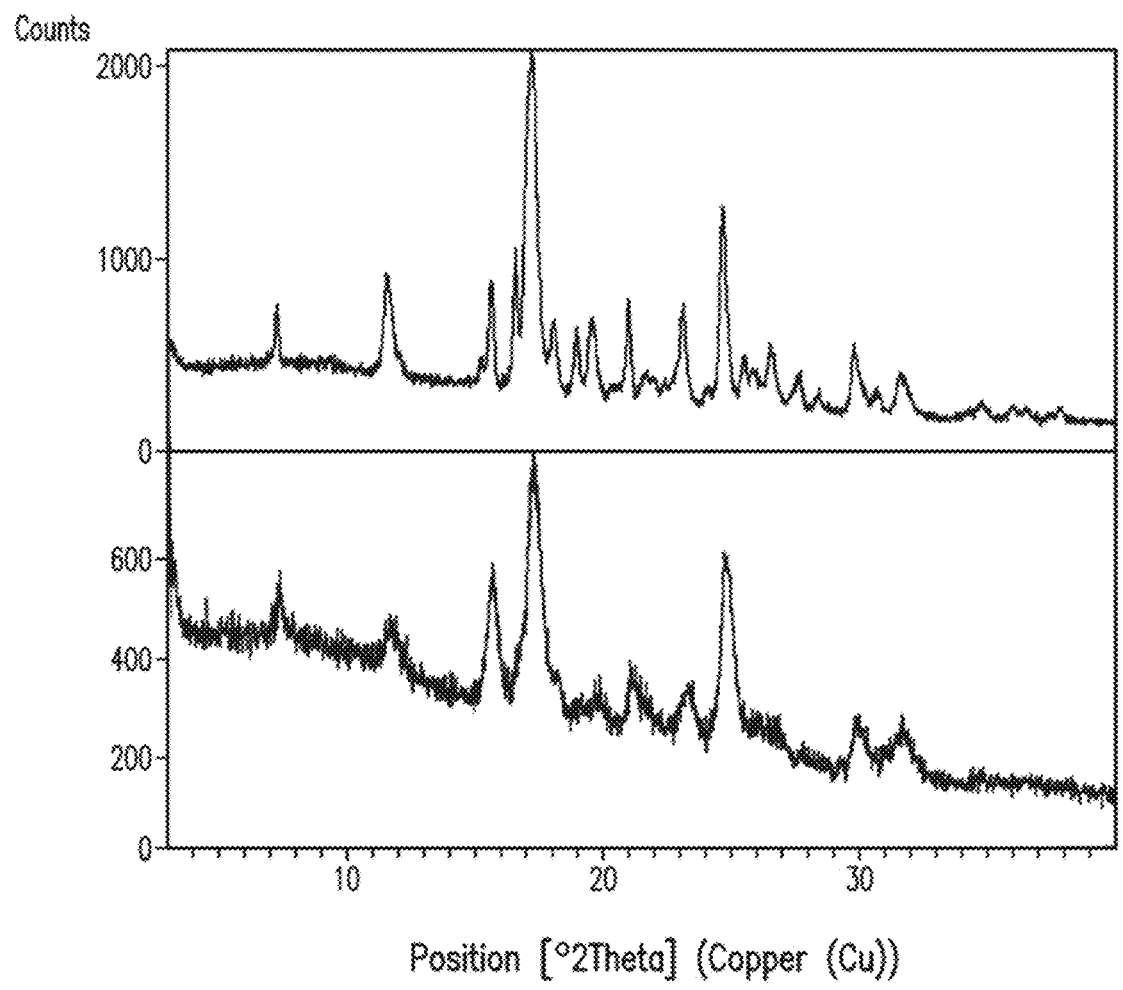

FIG. 8 depicts the comparison of the X-ray powder diffractogram plots of Form A of Compound 1 before (a) and after (b) compression.

Figure 9:
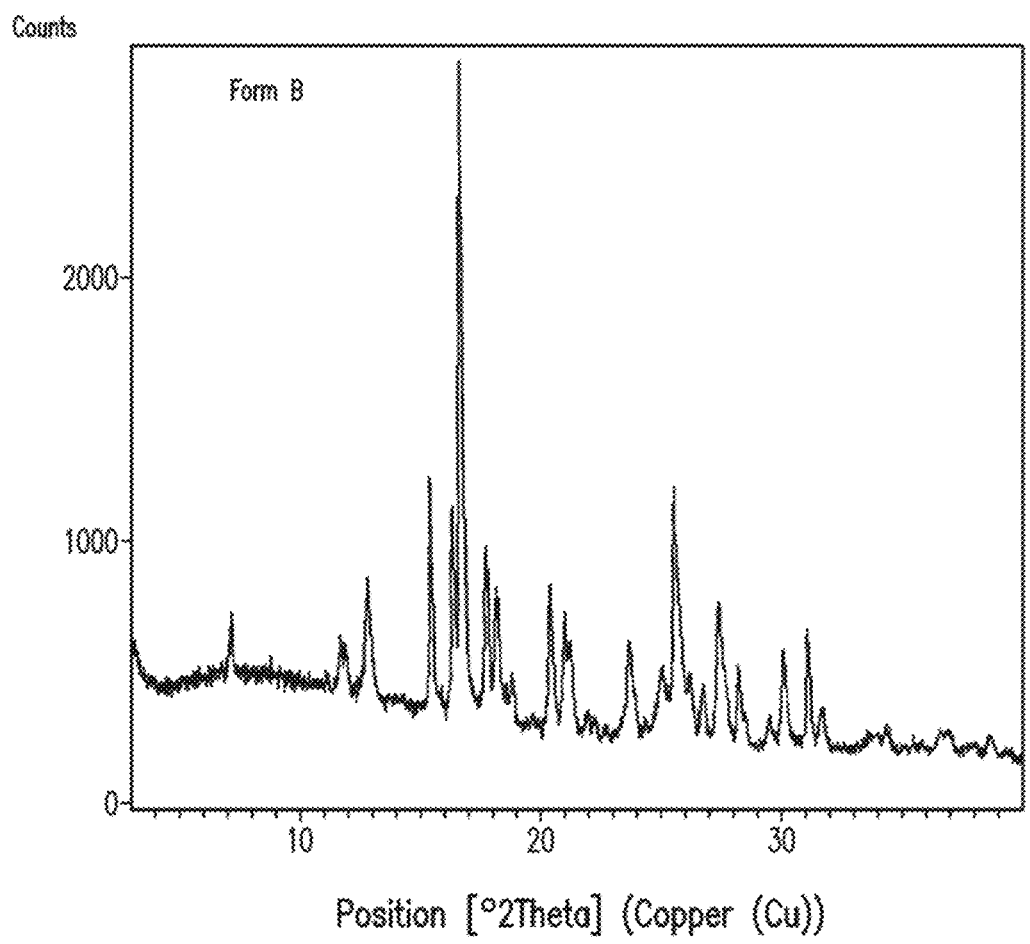

FIG. 9 depicts an XRPD plot of Form B of Compound 1.

Figure 10:
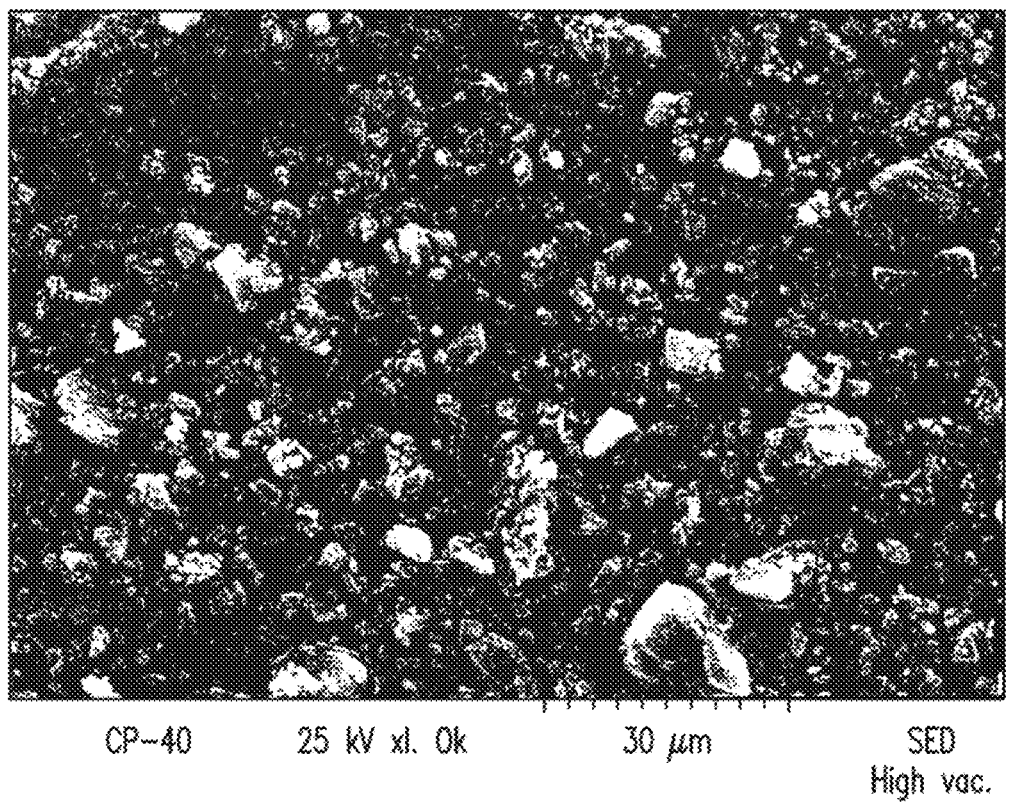

FIG. 10 depicts a SEM image of Form B of Compound 1.

Figure 11:
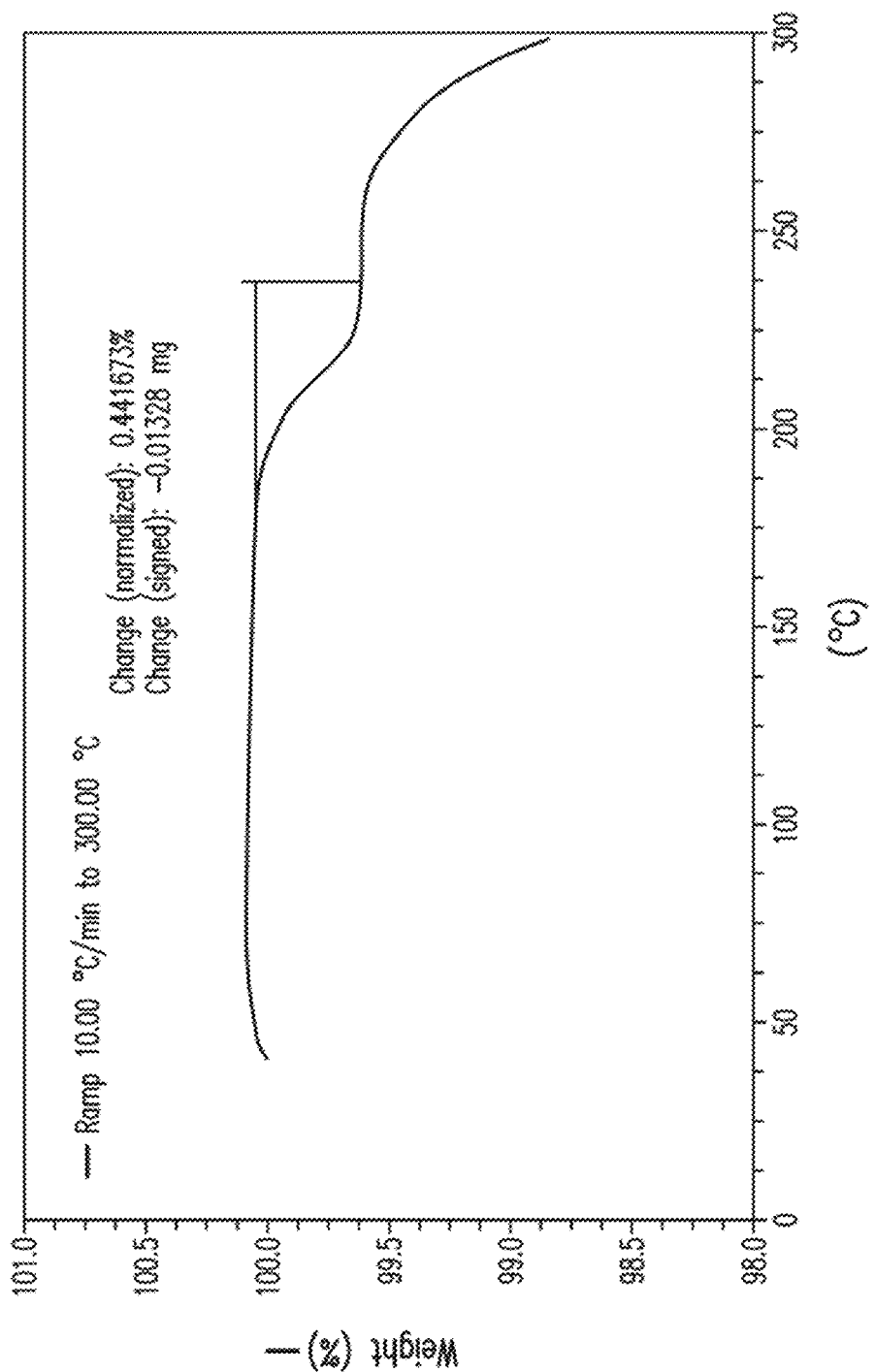

FIG. 11 depicts a TGA thermogram plot of Form B of Compound 1.

Figure 12:
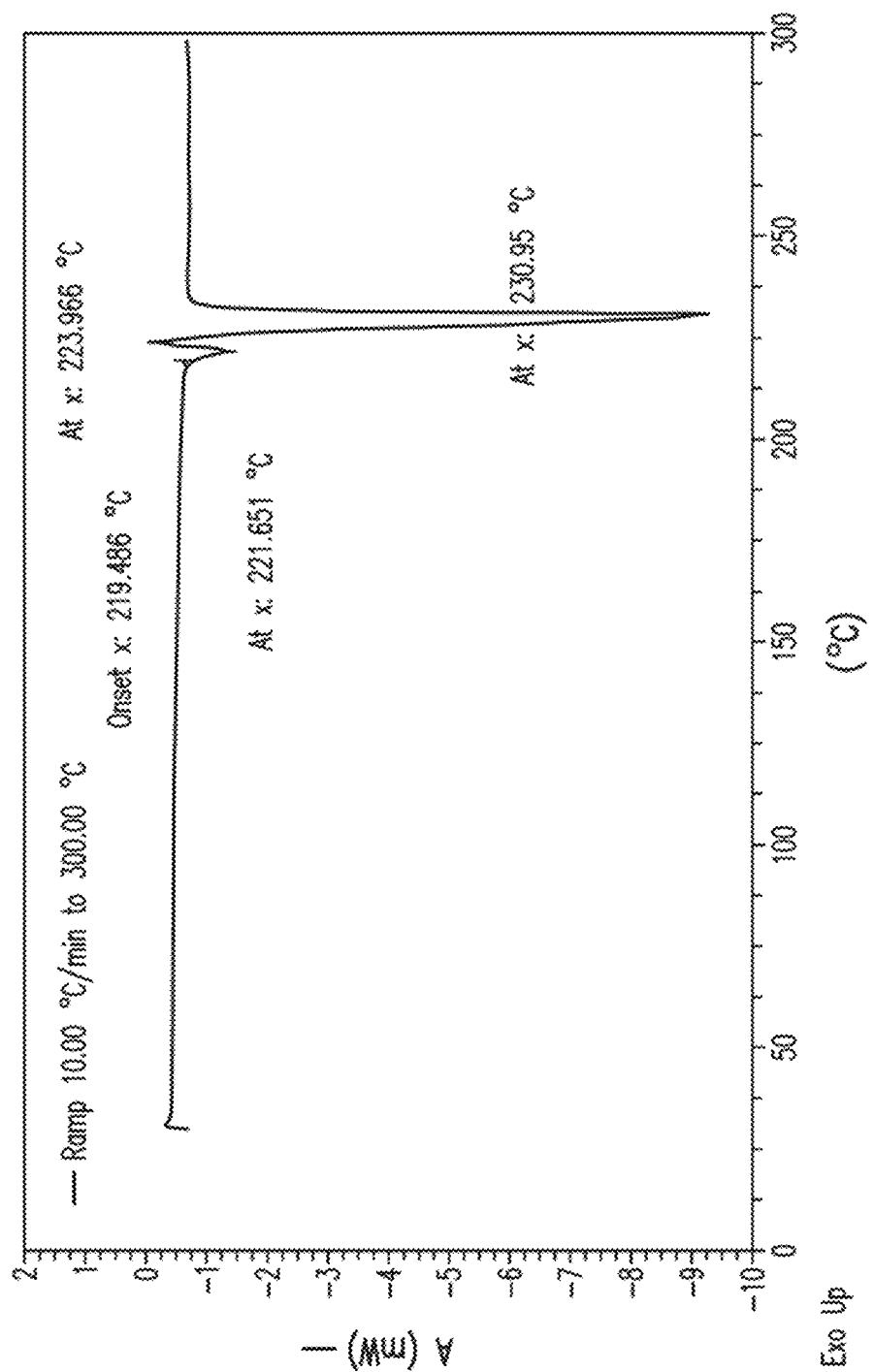

FIG. 12 depicts a DSC thermogram plot of Form B of Compound 1.

Figure 13:
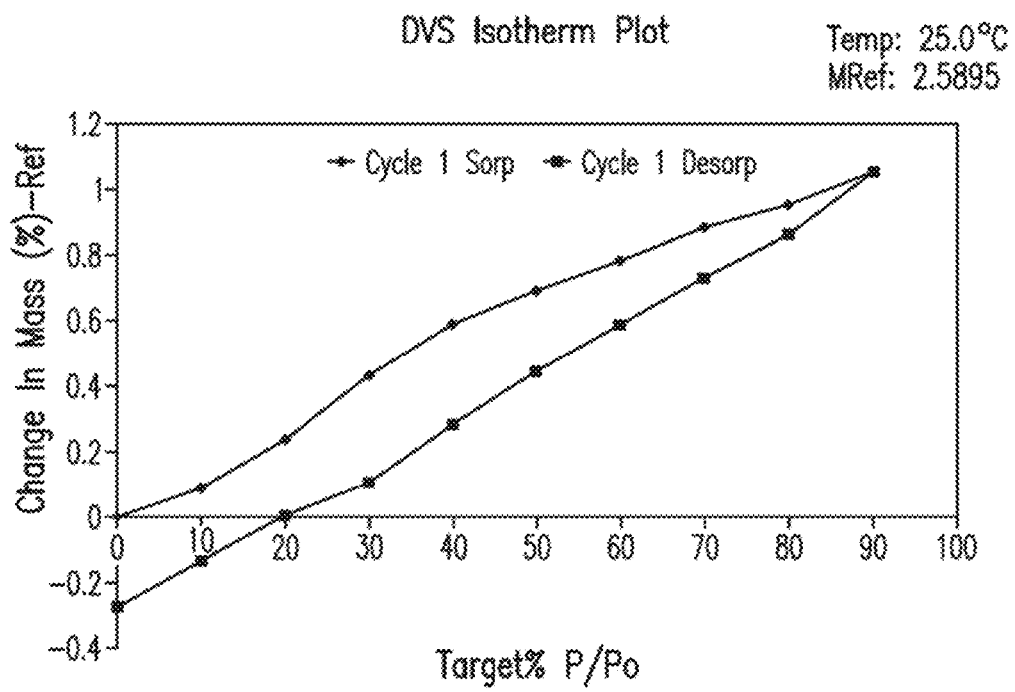

FIG. 13 provides a DVS isotherm plot of Form B of Compound 1.

Figure 14:
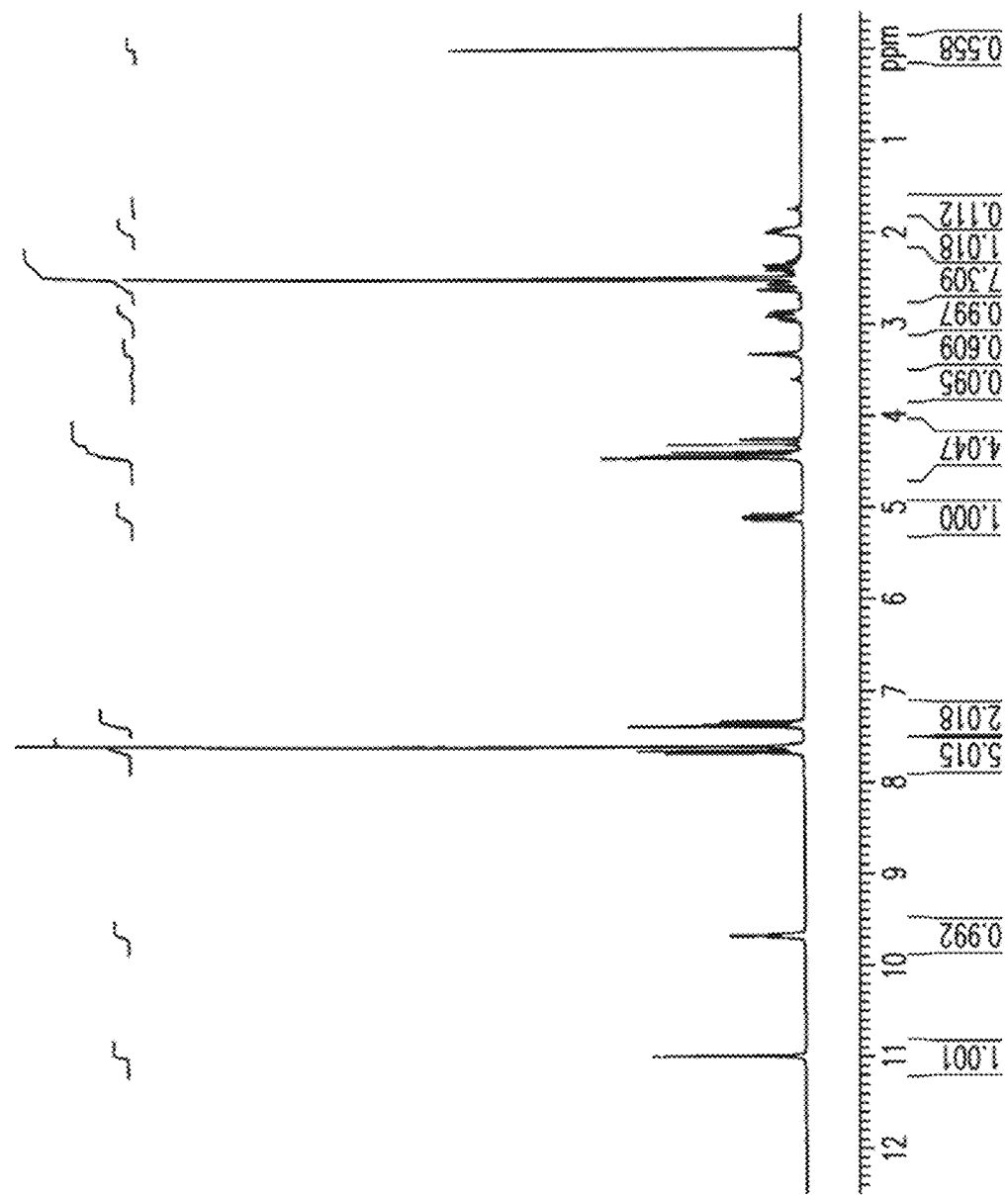

FIG. 14 provides a $^1$H NMR spectrum of Form B of Compound 1.

Figure 15:
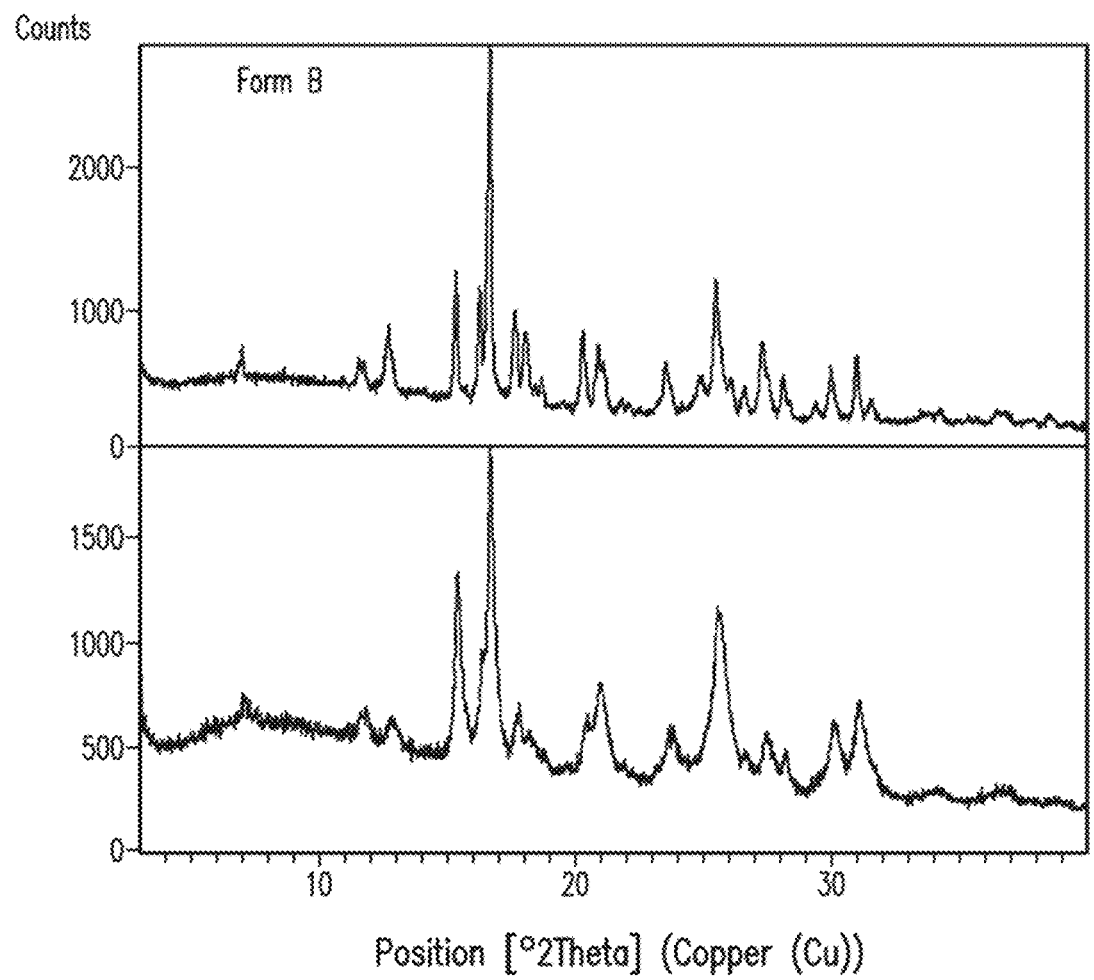

FIG. 15 depicts the comparison of the X-ray powder diffractogram plots of Form B of Compound 1 before (a) and after (b) compression.

Figure 16:
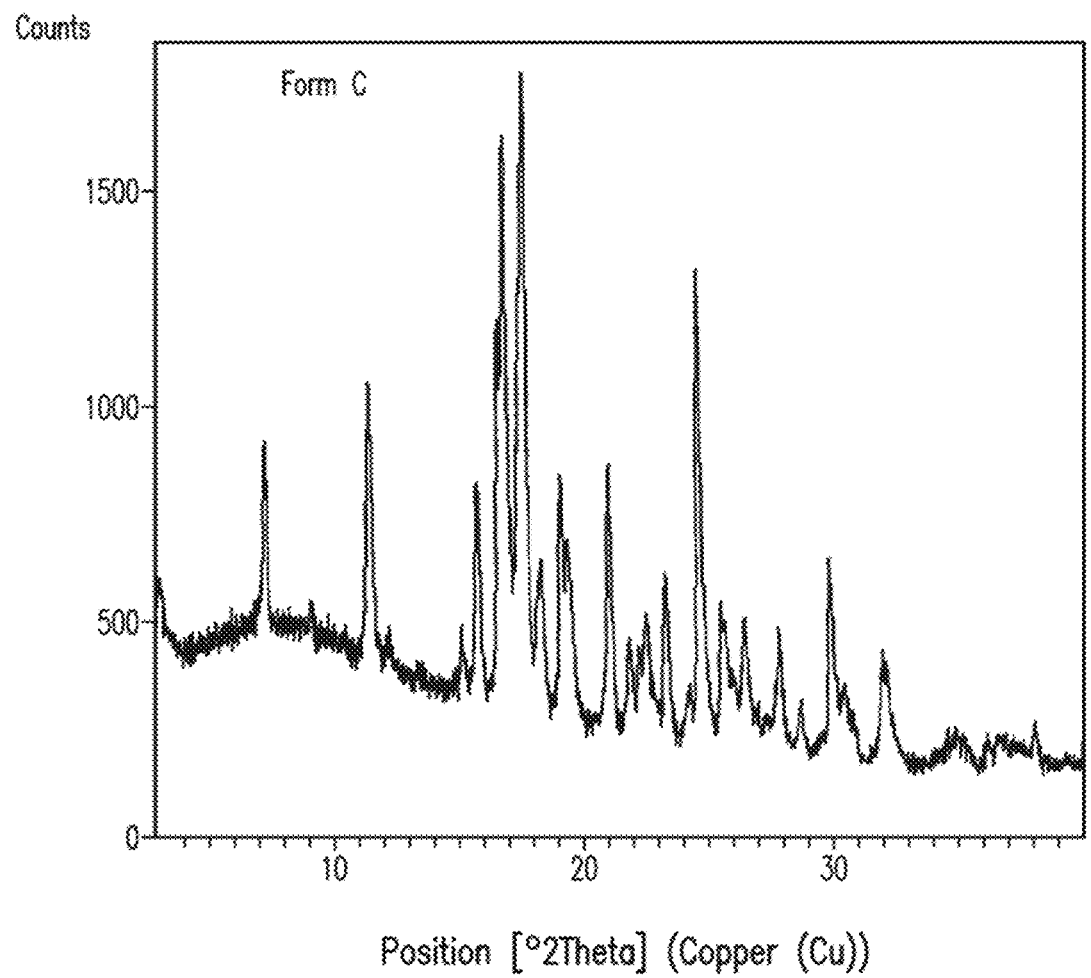

FIG. 16 depicts an XRPD plot of Form C of Compound 1.

Figure 17:
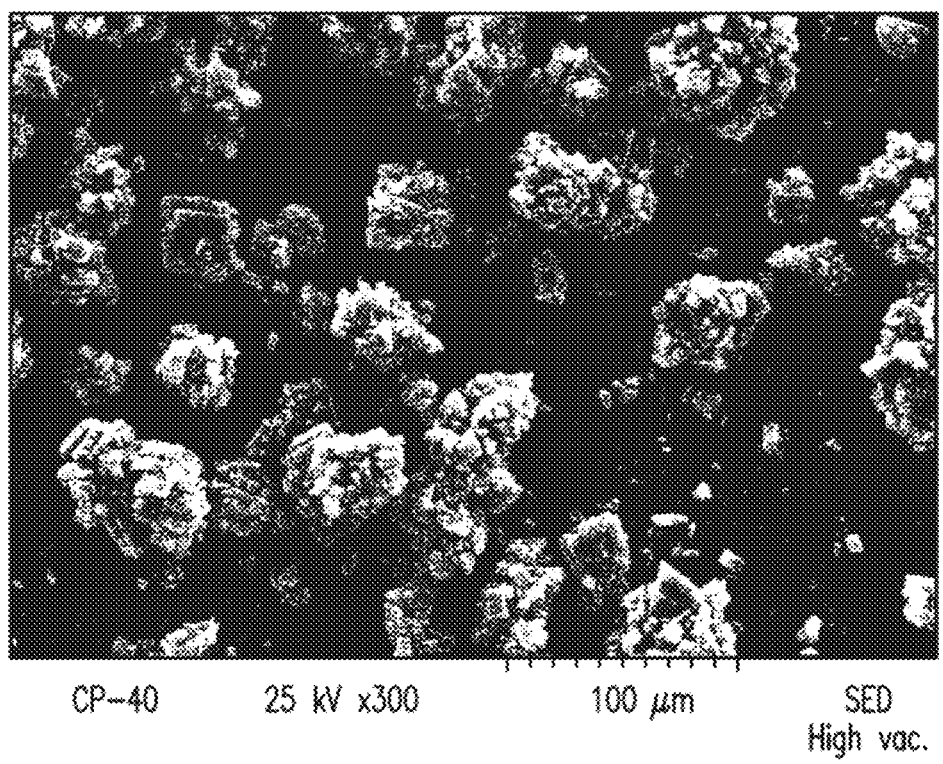

FIG. 17 depicts a SEM image of Form C of Compound 1.

Figure 18:
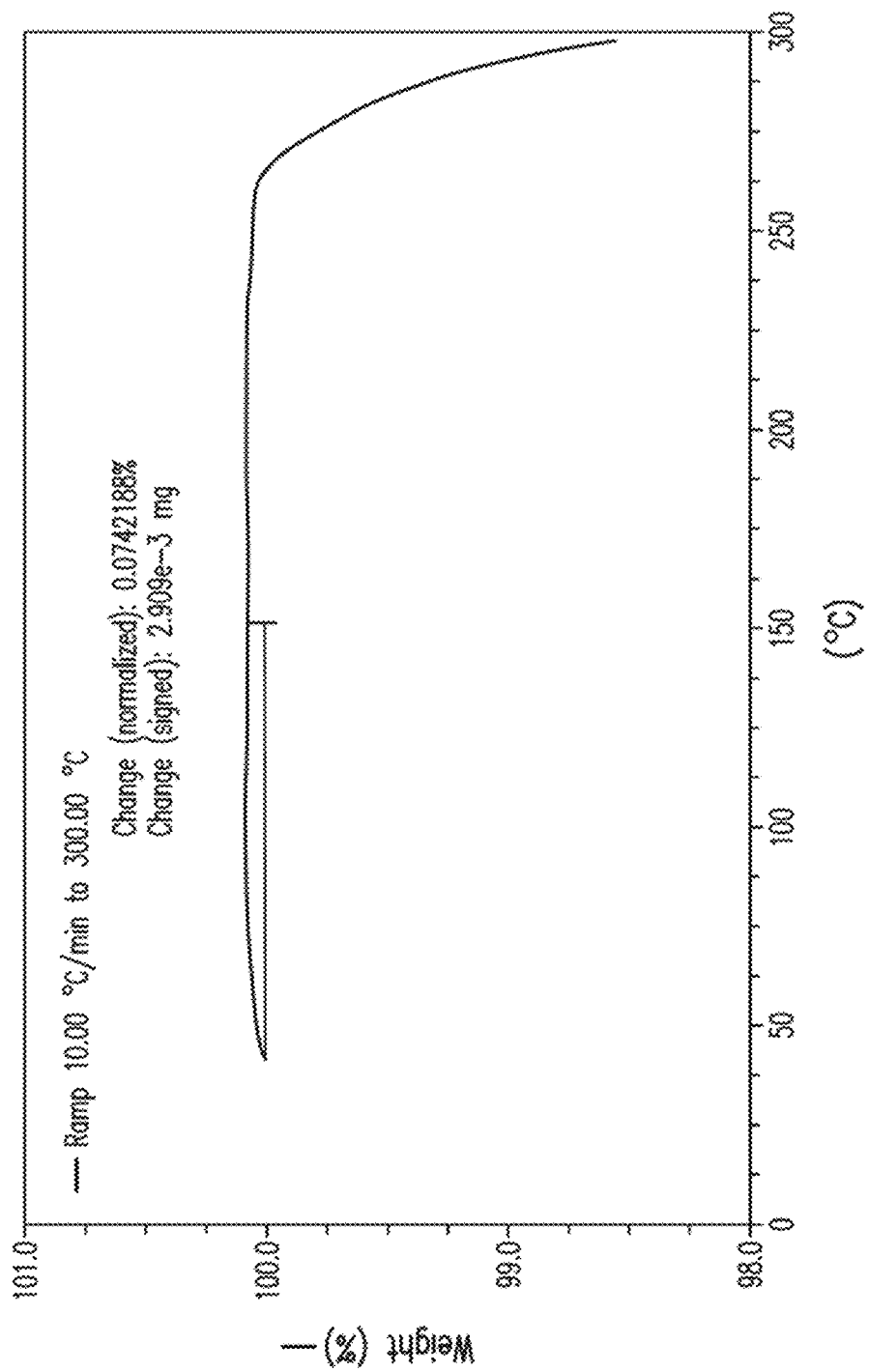

FIG. 18 depicts a TGA thermogram plot of Form C of Compound 1.

Figure 19:
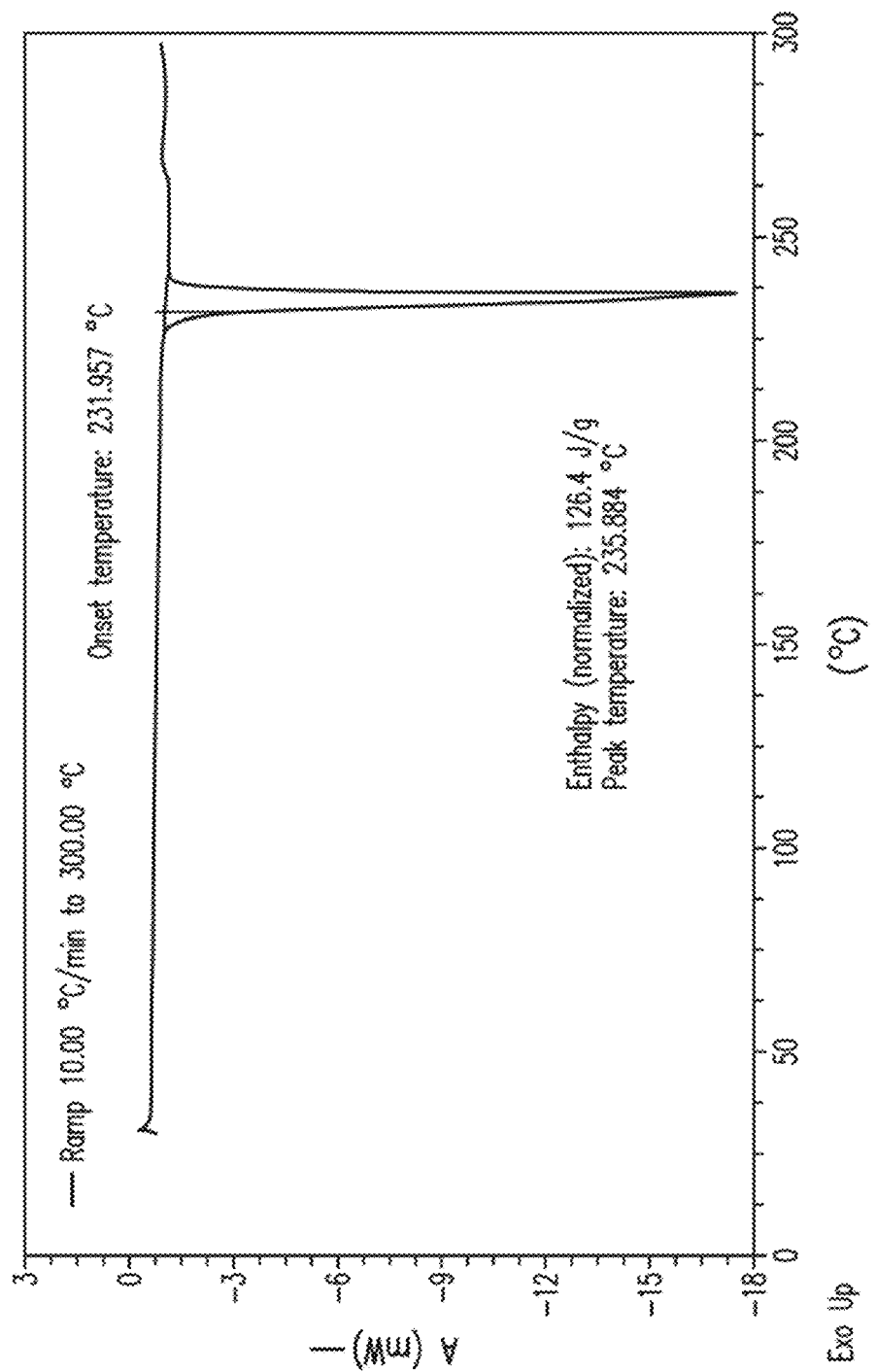

FIG. 19 depicts a DSC thermogram of Form C of Compound 1.

Figure 20:
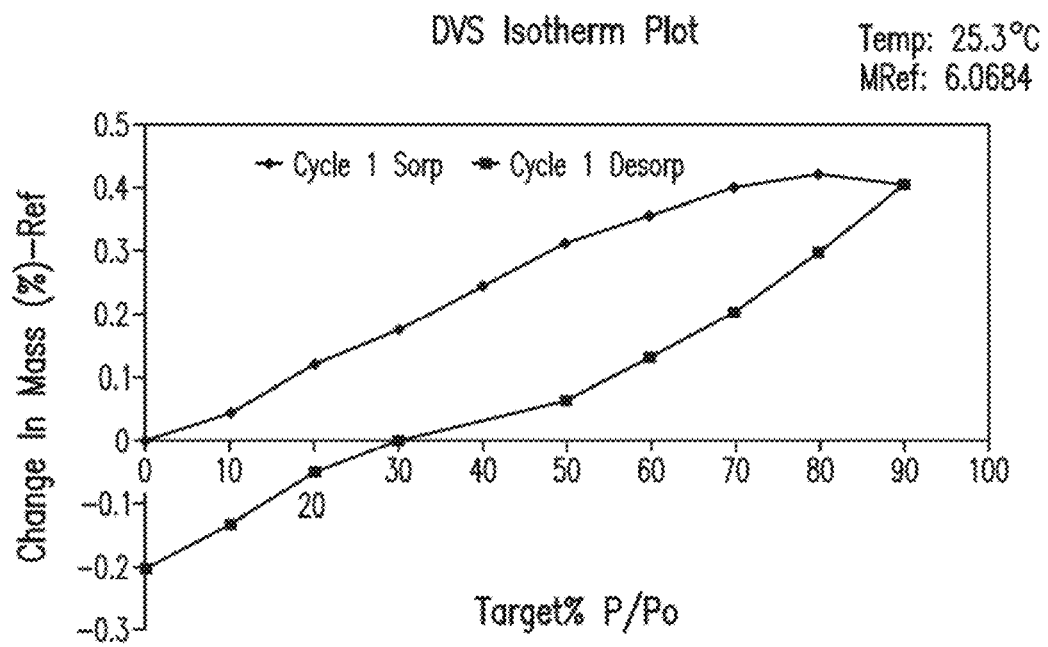

FIG. 20 provides a DVS isotherm plot of Form C of Compound 1.

Figure 21:
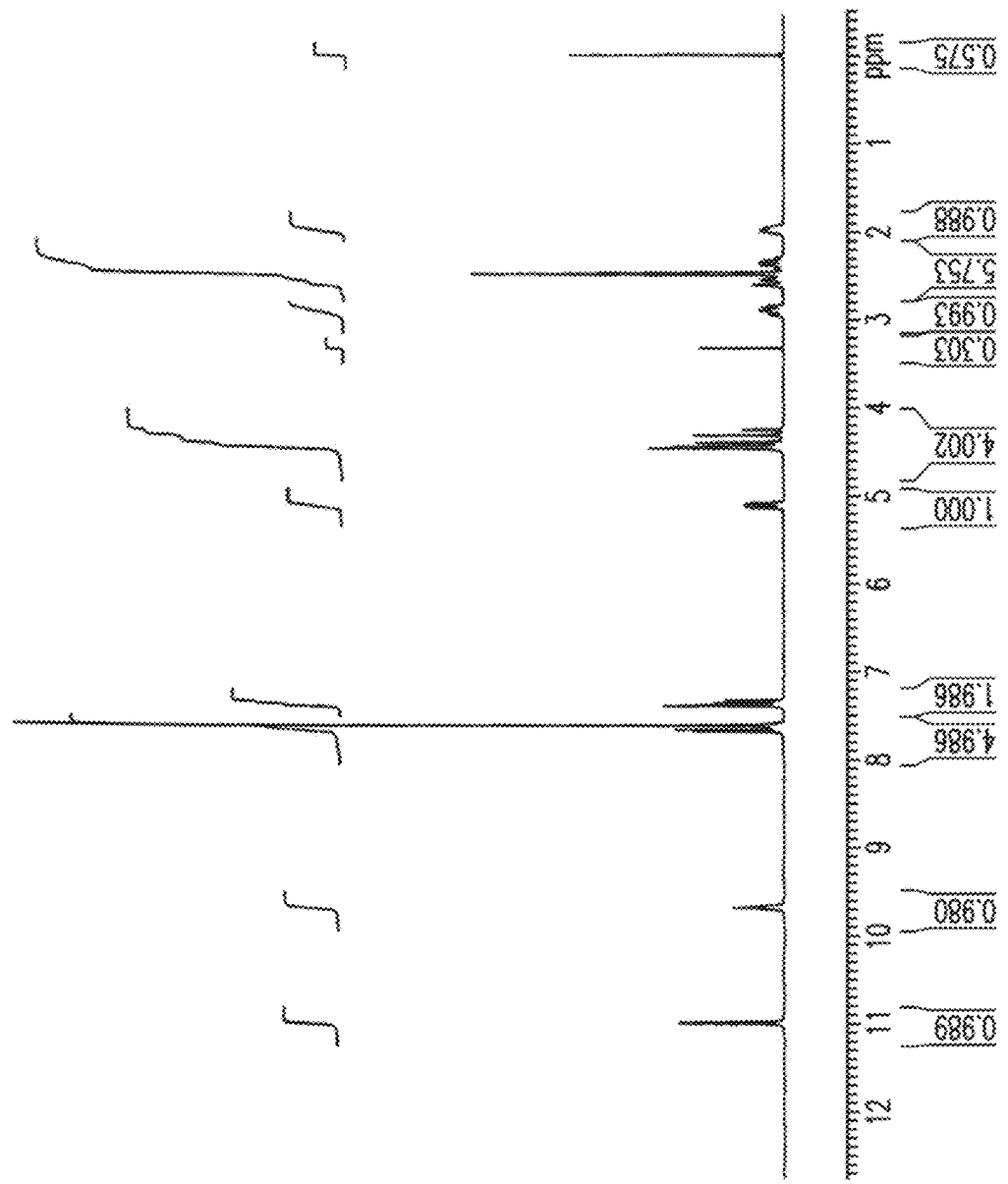

FIG. 21 provides a $^1$H NMR spectrum of Form C of Compound 1.

Figure 22:
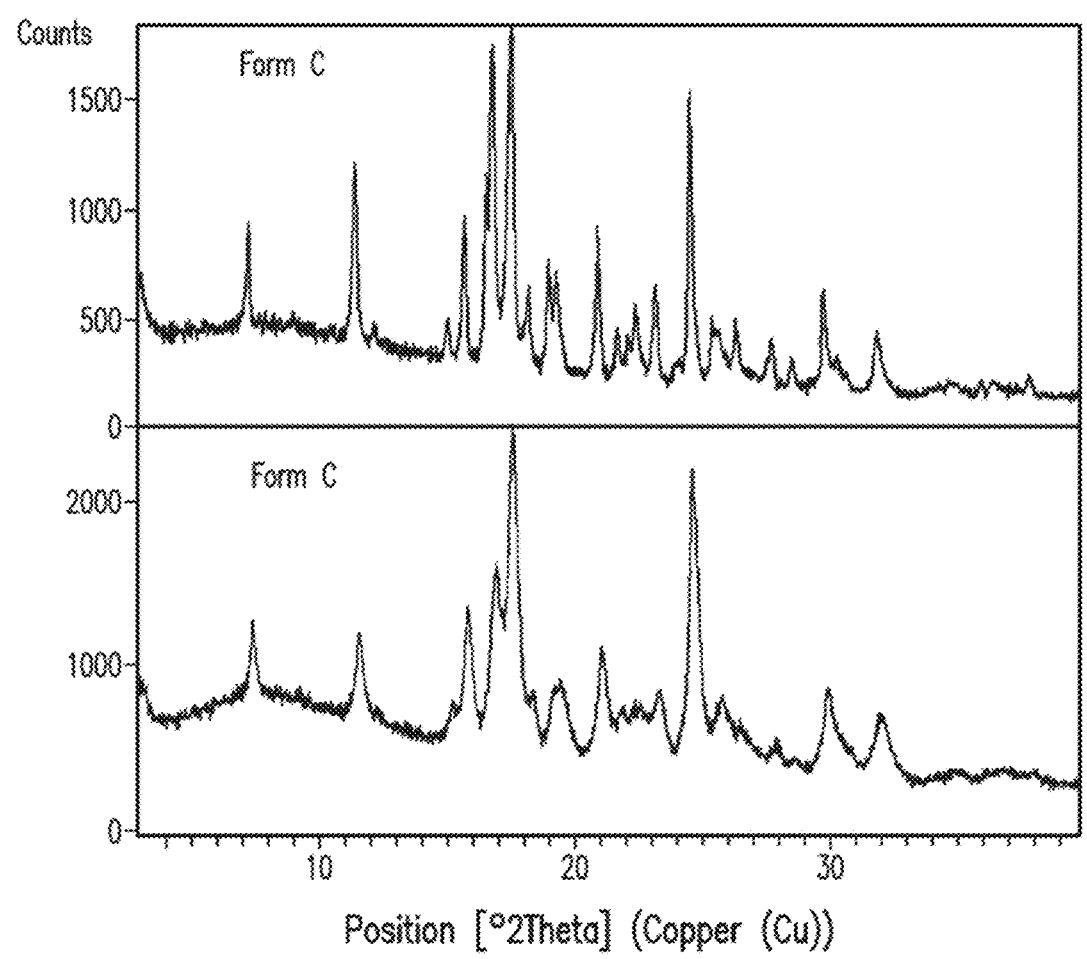

FIG. 22 depicts the comparison of the X-ray powder diffractogram plots of Form C of Compound 1 before (a) and after (b) compression.

Figure 23:
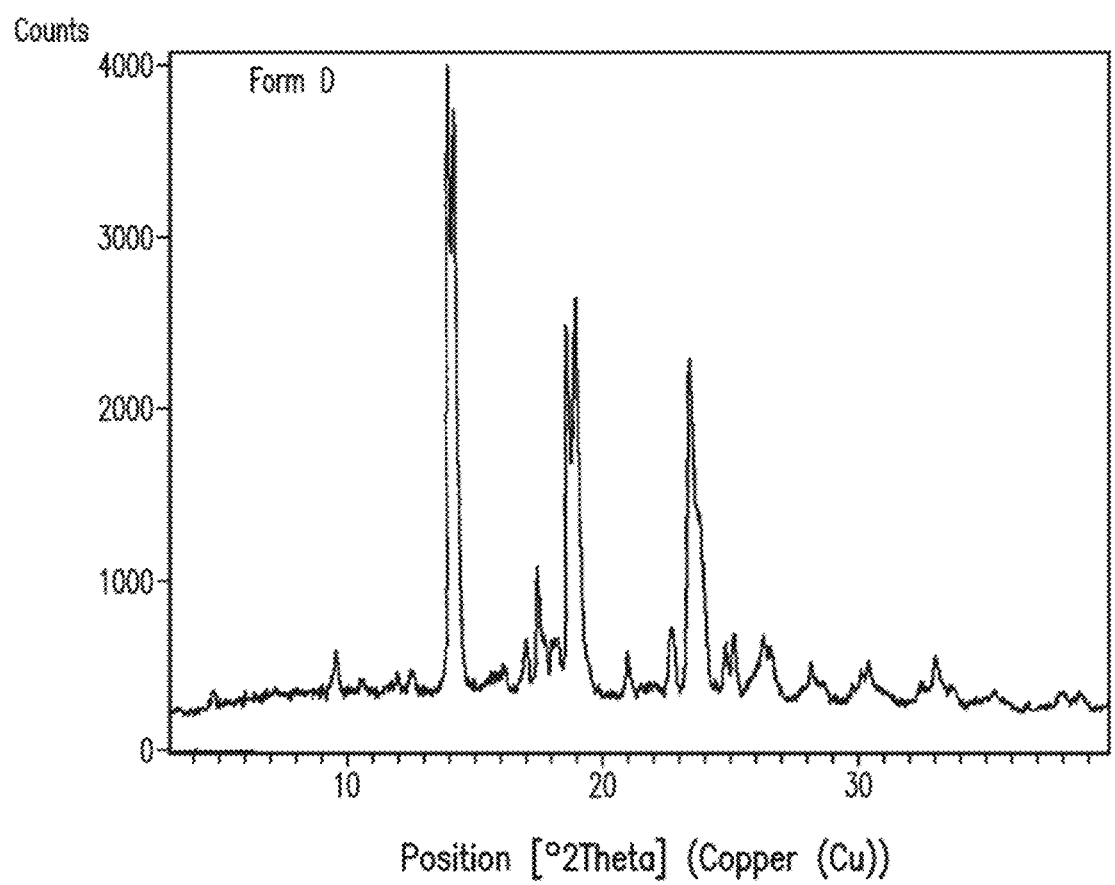

FIG. 23 depicts an XRPD plot of Form D of Compound 1.

Figure 24:
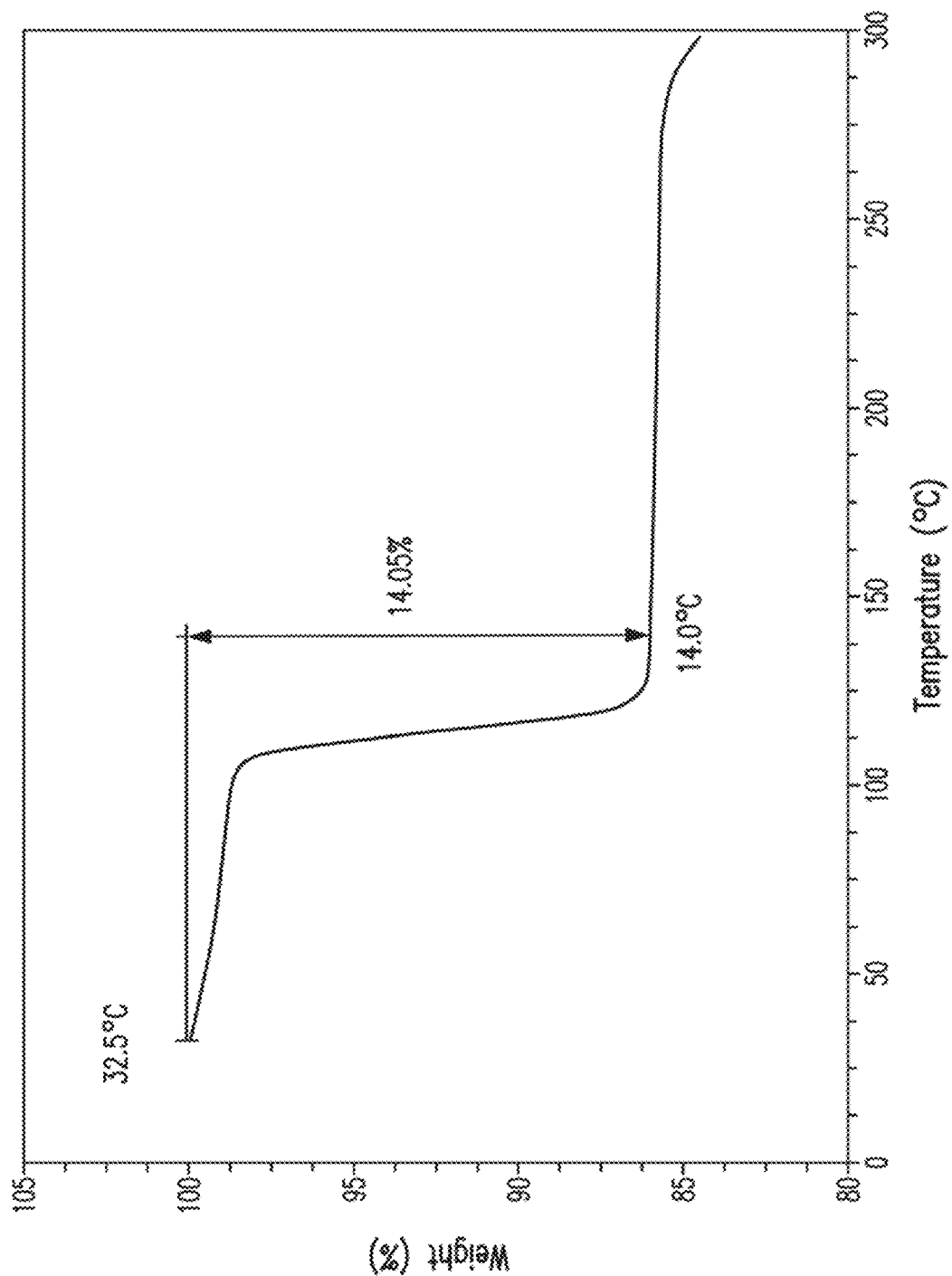

FIG. 24 depicts a TGA thermogram plot of Form D of Compound 1.

Figure 25:
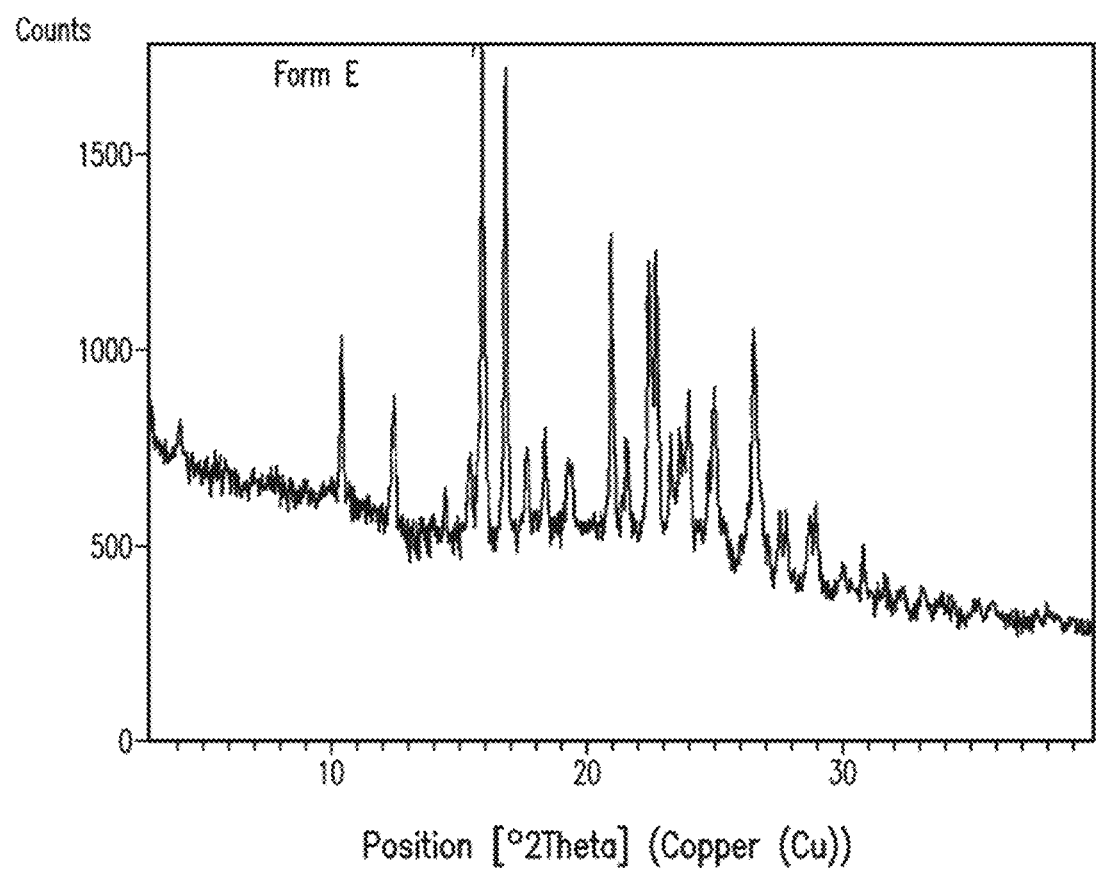

FIG. 25 depicts an XRPD plot of Form E of Compound 1.

Figure 26:
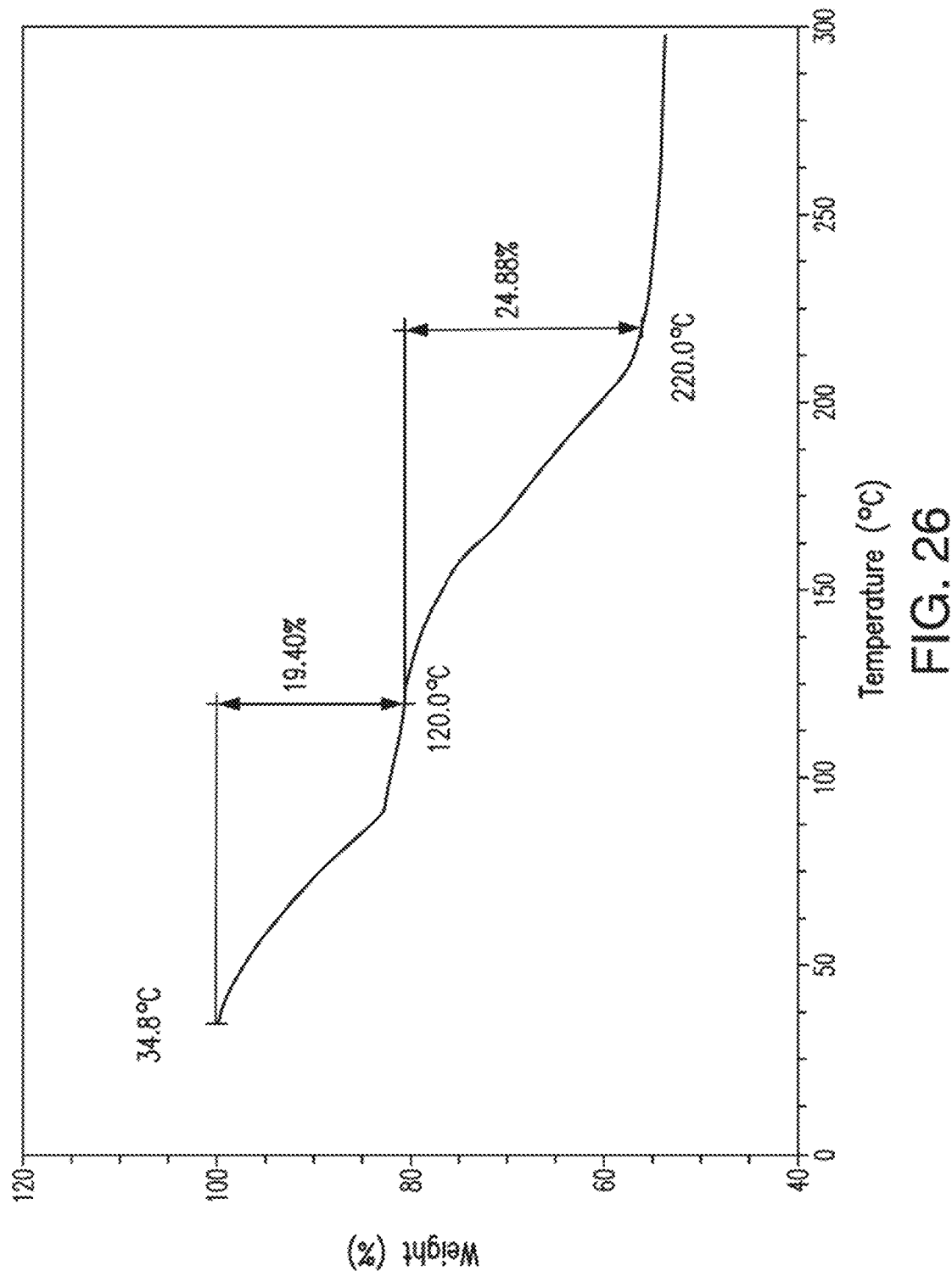

FIG. 26 depicts a TGA thermogram plot of Form E of Compound 1.

Figure 27:
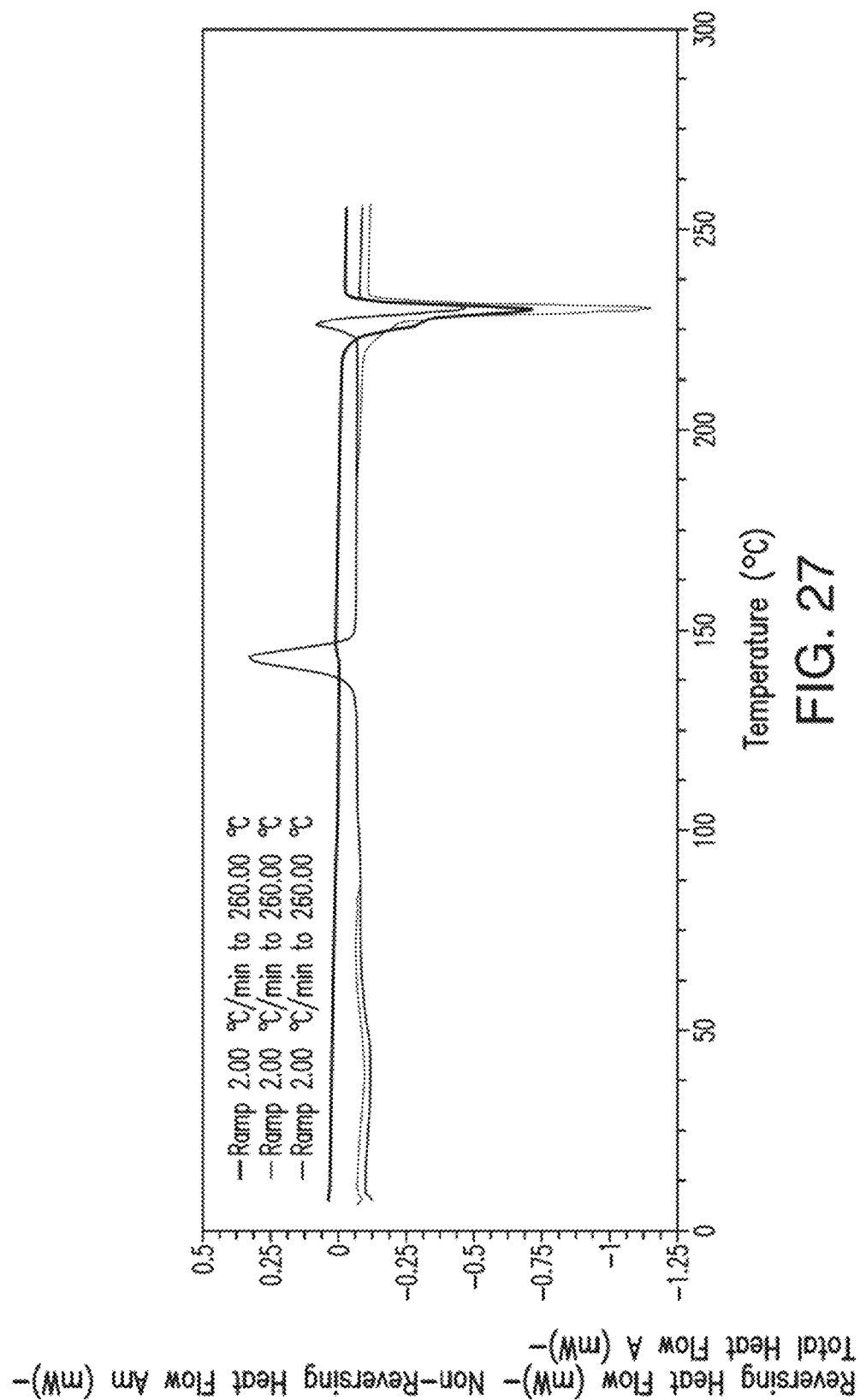

FIG. 27 depicts the modulated DSC thermogramplot of amorphous Compound 1.

Figure 28:
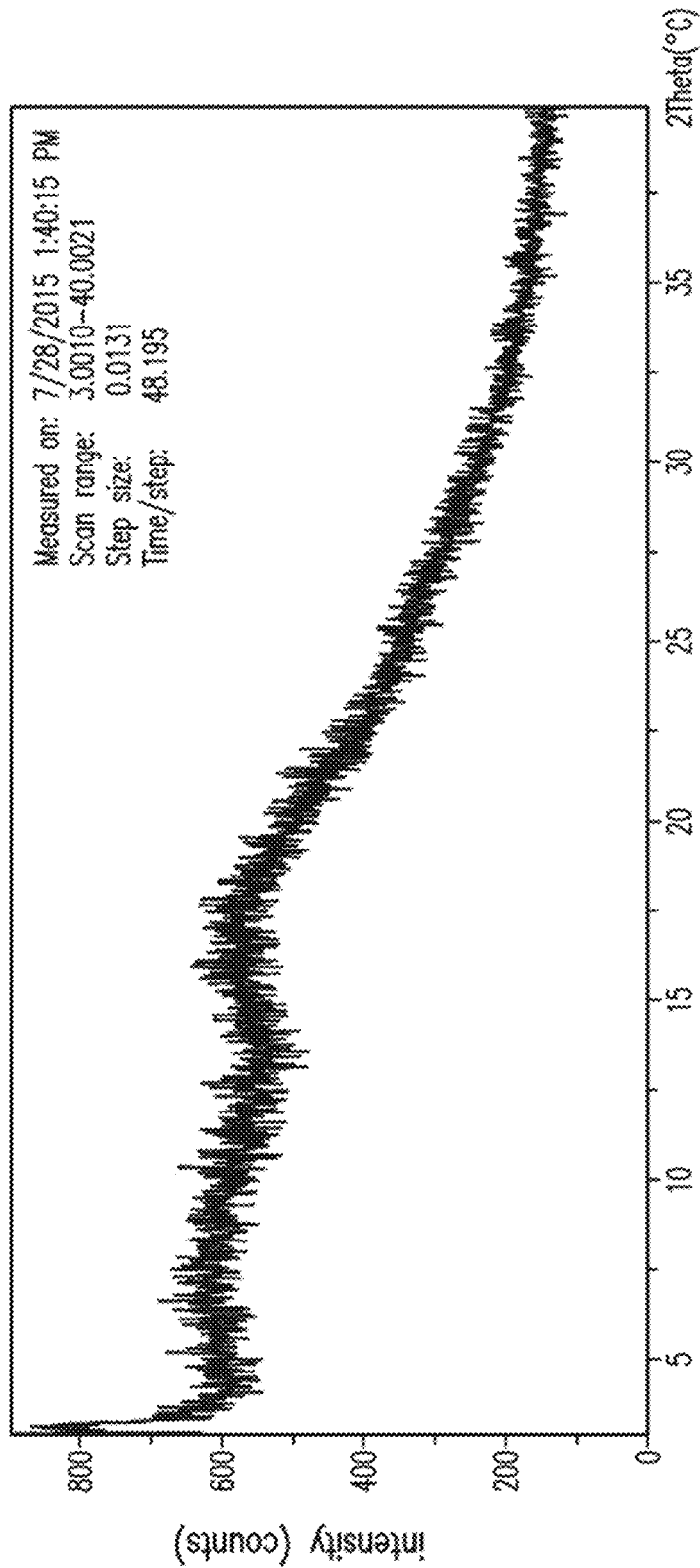

FIG. 28 depicts an XRPD plot of amorphous Compound 1.

Figure 29:
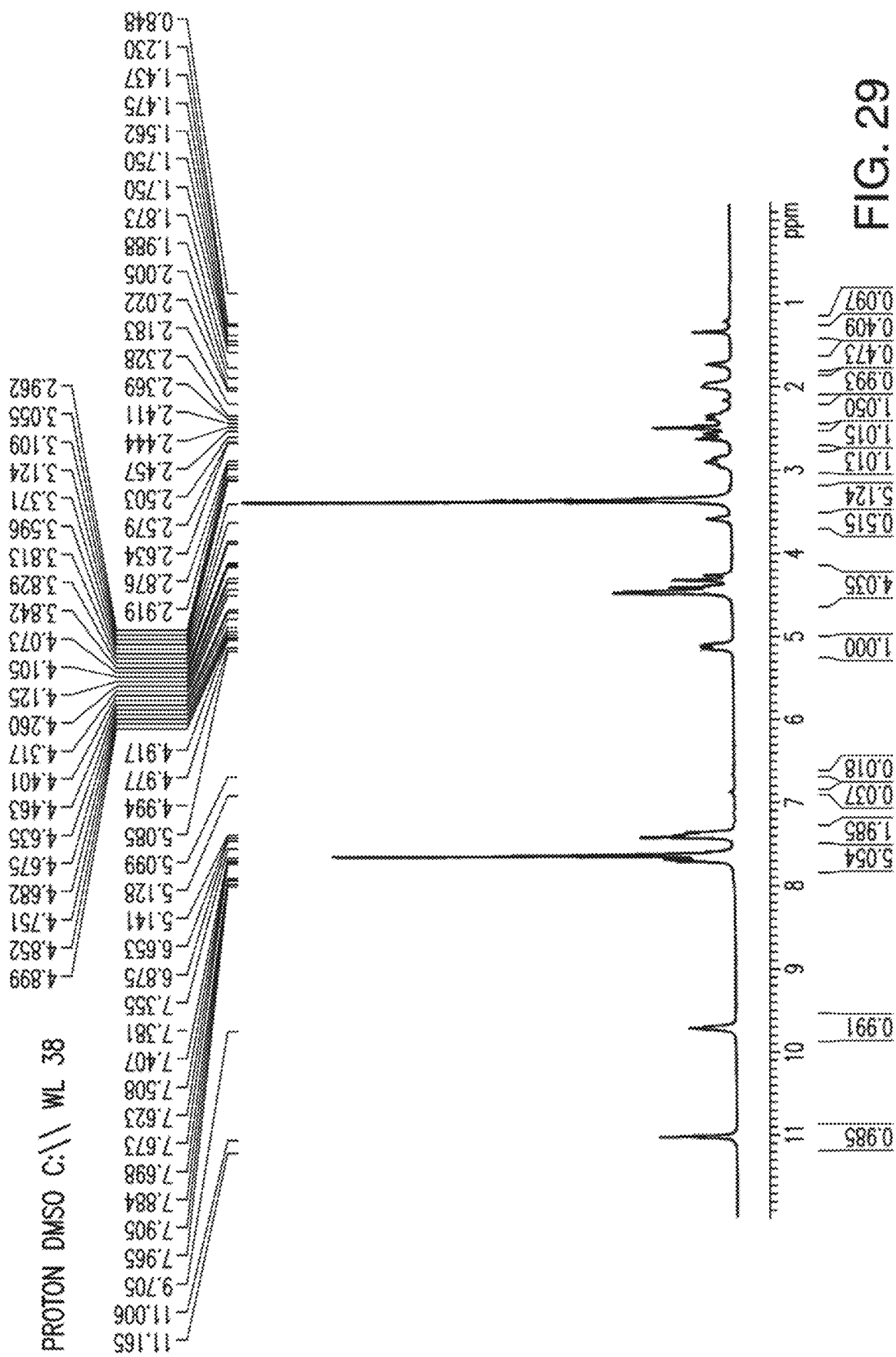

FIG. 29 depicts a $^1$H NMR spectrum of amorphous Compound 1.

6. DETAILED DESCRIPTION

6.1. Definitions

As used herein, the term "Compound 1" refers to 2-(4-chlorophenyl)-N-((2-(2,6-dioxopiperidin-3-yl)-1-oxoisoindolin-5-yl)methyl)-2,2-difluoroacetamide, which has the following structure:

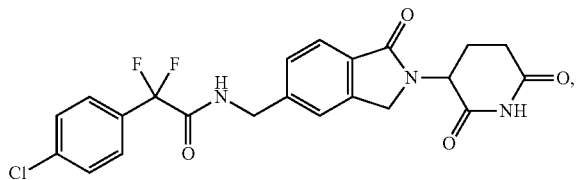 [SMILES: O=C1CCC(N2Cc3cc(CNC(=O)C(F)(F)c4ccc(Cl)cc4)ccc3C2=O)C(=O)N1]

and tautomers thereof.

As used herein and unless otherwise specified, the terms "solid form" and related terms refer to a physical form which is not predominantly in a liquid or a gaseous state. As used herein and unless otherwise specified, the term "solid form" and related terms, when used herein to refer to Compound 1, refer to a physical form comprising Compound 1 which is not predominantly in a liquid or a gaseous state. The solid forms may be crystalline, amorphous, or mixtures thereof. In particular embodiments, solid forms may be liquid crystals. A "single-component" solid form comprising Compound 1 consists essentially of Compound 1. A "multiple-component" solid form comprising Compound 1 comprises a significant quantity of one or more additional species, such as ions and/or molecules, within the solid form. Multiple-component solid forms comprising Compound 1 include co-crystals, solvates (e.g., hydrates), and clathrates of Compound 1. In particular embodiments, the term "solid form comprising Compound 1" and related terms include single-component and multiple-component solid forms comprising Compound 1. In particular embodiments, "solid forms comprising Compound 1" and related terms include crystal forms comprising Compound 1, amorphous forms comprising Compound 1, and mixtures thereof.

As used herein and unless otherwise specified, the term "crystalline" and related terms used herein, when used to describe a compound, substance, modification, material, component or product, unless otherwise specified, mean that the compound, substance, modification, material, component or product is substantially crystalline as determined by X-ray diffraction. See, e.g., Remington: The Science and Practice of Pharmacy, 21$^{st}$ edition, Lippincott, Williams and Wilkins, Baltimore, Md. (2005); The United States Pharmacopeia, 23$^{rd}$ ed., 1843-1844 (1995).

As used herein and unless otherwise specified, the term "crystal forms," "crystalline forms" and related terms herein refer to solid forms that are crystalline. Crystal forms include single-component crystal forms and multiple-component crystal forms, and include polymorphs, solvates, hydrates, and/or other molecular complexes. In certain embodiments, a crystal form of a substance may be substantially free of amorphous forms and/or other crystal forms. In certain embodiments, a crystal form of a substance may contain less than about 1%, 2%, 3%, 4%, 5%, 6%, 7%, 8%, 9%, 10%, 15%, 20%, 25%, 30%, 35%, 40%, 45% or 50% of one or more amorphous forms and/or other crystal forms on a weight basis. In certain embodiments, a crystal form of a substance may be physically and/or chemically pure. In certain embodiments, a crystal form of a substance may be about 99%, 98%, 97%, 96%, 95%, 94%, 93%, 92%, 91% or 90% physically and/or chemically pure.

As used herein and unless otherwise specified, the terms "polymorphs," "polymorphic forms" and related terms herein, refer to two or more crystal forms that consist essentially of the same molecule, molecules, and/or ions. Like different crystal forms, different polymorphs may have different physical properties such as, e.g., melting temperature, heat of fusion, solubility, dissolution properties and/or vibrational spectra, as a result of the arrangement or conformation of the molecules and/or ions in the crystal lattice. The differences in physical properties may affect pharmaceutical parameters such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some solid-state transitions may result in lack of potency or, at the other extreme, toxicity. In addition, the physical properties may be important in processing (e.g., one polymorph might be more likely to form solvates or might be difficult to filter and wash free of impurities, and particle shape and size distribution might be different between polymorphs).

As used herein and unless otherwise specified, the terms "solvate" and "solvated," refer to a crystal form of a substance which contains solvent. The terms "hydrate" and "hydrated" refer to a solvate wherein the solvent comprises water. "Polymorphs of solvates" refers to the existence of more than one crystal form for a particular solvate composition. Similarly, "polymorphs of hydrates" refers to the existence of more than one crystal form for a particular hydrate composition. The term "desolvated solvate," as used herein, refers to a crystal form of a substance which may be prepared by removing the solvent from a solvate.

As used herein and unless otherwise specified, the term "amorphous," "amorphous form," and related terms used herein, mean that the substance, component or product in question is not substantially crystalline as determined by X-ray diffraction. In particular, the term "amorphous form" describes a disordered solid form, i.e., a solid form lacking long range crystalline order. In certain embodiments, an amorphous form of a substance may be substantially free of other amorphous forms and/or crystal forms. In other embodiments, an amorphous form of a substance may contain less than about 1%, 2%, 3%, 4%, 5%, 10%, 15%, 20%, 25%, 30%, 35%, 40%, 45% or 50% of one or more other amorphous forms and/or crystal forms on a weight basis. In certain embodiments, an amorphous form of a substance may be physically and/or chemically pure. In certain embodiments, an amorphous form of a substance be about 99%, 98%, 97%, 96%, 95%, 94%, 93%, 92%, 91% or 90% physically and/or chemically pure.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

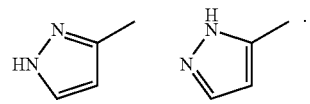

As readily understood by one skilled in the art, a wide variety of functional groups and other structures may exhibit tautomerism and all tautomers of Compound 1 are within the scope of the present invention.

Techniques for characterizing crystal forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility measurements, dissolution measurements, elemental analysis, and Karl Fischer analysis. Characteristic unit cell parameters may be determined using one or more techniques such as, but not limited to, X-ray diffraction and neutron diffraction, including single-crystal diffraction and powder diffraction. Techniques useful for analyzing powder diffraction data include profile refinement, such as Rietveld refinement, which may be used, e.g., to analyze diffraction peaks associated with a single phase in a sample comprising more than one solid phase. Other methods useful for analyzing powder diffraction data include unit cell indexing, which allows one of skill in the art to determine unit cell parameters from a sample comprising crystalline powder.

As used herein and unless otherwise specified, the terms "about" and "approximately," when used in connection with a numeric value or a range of values which is provided to characterize a particular solid form, e.g., a specific temperature or temperature range, such as, e.g., that describing a DSC or TGA thermal event, including, e.g., melting, dehydration, desolvation or glass transition events; a mass change, such as, e.g., a mass change as a function of temperature or humidity; a solvent or water content, in terms of, e.g., mass or a percentage; or a peak position, such as, e.g., in analysis by IR or Raman spectroscopy or)(RFD; indicate that the value or range of values may deviate to an extent deemed reasonable to one of ordinary skill in the art while still describing the particular solid form. For example, in particular embodiments, the terms "about" and "approximately," when used in this context and unless otherwise specified, indicate that the numeric value or range of values may vary within 25%, 20%, 15%, 10%, 9%, 8%, 7%, 6%, 5%, 4%, 3%, 2%, 1.5%, 1%, 0.5%, or 0.25% of the recited value or range of values.

As used herein and unless otherwise specified, a sample comprising a particular crystal form or amorphous form that is "substantially pure," e.g., substantially free of other solid forms and/or of other chemical compounds, contains, in particular embodiments, less than about 25%, 20%, 15%, 10%, 9%, 8%, 7%, 6%, 5%, 4%, 3%, 2%, 1%, 0.75%, 0.5%, 0.25% or 0.1% percent by weight of one or more other solid forms and/or of other chemical compounds.

As used herein and unless otherwise specified, a sample or composition that is "substantially free" of one or more other solid forms and/or other chemical compounds means that the composition contains, in particular embodiments, less than about 25%, 20%, 15%, 10%, 9%, 8%, 7%, 6%, 5%, 4%, 3%, 2%, 1%, 0.75%, 0.5%, 0.25% or 0.1% percent by weight of one or more other solid forms and/or other chemical compounds.

As used herein, the term "patient" refers to a mammal, particularly a human.

As used herein, term "adverse effects" includes, but is not limited to gastrointestinal, renal and hepatic toxicities, leukopenia, increases in bleeding times due to, e.g., thrombocytopenia, and prolongation of gestation, nausea, vomiting, somnolence, asthenia, dizziness, teratogenicity, extra-pyramidal symptoms, akathisia, cardiotoxicity including cardiovascular disturbances, inflammation, male sexual dysfunction, and elevated serum liver enzyme levels. The term "gastrointestinal toxicities" includes, but is not limited to, gastric and intestinal ulcerations and erosions. The term "renal toxicities" includes, but is not limited to, such conditions as papillary necrosis and chronic interstitial nephritis.

As used herein and unless otherwise indicated, the phrases "reduce or avoid adverse effects" and "reducing or avoiding adverse effects" mean the reduction of the severity of one or more adverse effects as defined herein.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a patient with such a disease or disorder. In some embodiments, the terms refer to the administration of a compound provided herein, with or without other additional active agent, after the onset of symptoms of the particular disease.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of diseases or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. Often, the beneficial effects that a patient derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, a "therapeutically effective amount" of a compound is an amount sufficient to provide a therapeutic benefit in the treatment and/or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

As used herein, the term "tumor," refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

As used herein, "hematologic malignancy" refers to cancer of the body's blood-forming and immune system-the bone marrow and lymphatic tissue. Such cancers include leukemias, lymphomas (Non-Hodgkin's Lymphoma), Hodgkin's disease (also called Hodgkin's Lymphoma) and myeloma. In one embodiment, the myeloma is multiple myeloma. In some embodiments, the leukemia is, for example, acute myelogenous leukemia (AML), acute lymphocytic leukemia (ALL), adult T-cell leukemia, chronic lymphocytic leukemia (CLL), hairy cell leukemia, myelodysplasia, myeloproliferative disorders, chronic myelogenous leukemia (CML), myelodysplastic syndrome (MDS), human lymphotropic virus-type 1 (HTLV-1) leukemia, mastocytosis, or B-cell acute lymphoblastic leukemia. In some embodiments, the lymphoma is, for example, diffuse large B-cell lymphoma (DLBCL), B-cell immunoblastic lymphoma, small non-cleaved cell lymphoma, human lymphotropic virus-type 1 (HTLV-1) leukemia/lymphoma, adult T-cell lymphoma, peripheral T-cell lymphoma (PTCL), cutaneous T-cell lymphoma (CTCL), mantle cell lymphoma (MCL), Hodgkin lymphoma (HL), non-Hodgkin lymphoma (NHL), AIDS-related lymphoma, follicular lymphoma, small lymphocytic lymphoma, T-cell/histiocyte rich large B-cell lymphoma, transformed lymphoma, primary mediastinal (thymic) large B-cell lymphoma, splenic marginal zone lymphoma, Richter's transformation, nodal marginal zone lymphoma, or ALK-positive large B-cell lymphoma. In one embodiment, the hematological cancer is indolent lymphoma including, for example, DLBCL, follicular lymphoma, or marginal zone lymphoma.

The term "leukemia" refers to malignant neoplasms of the blood-forming tissues. The leukemia includes, but is not limited to, chronic lymphocytic leukemia, chronic myelocytic leukemia, acute lymphoblastic leukemia, acute myeloid leukemia, and acute myeloblastic leukemia. The leukemia can be relapsed, refractory or resistant to conventional therapy.

The term "myelodysplastic syndrome" refers to hematological conditions characterized by abnormalities in the production of one or more of the cellular components of blood (red cells, white cells (other than lymphocytes) and platelets (or their progenitor cells, megakaryocytes)), and includes the following disorders: refractory anemia (RA); RA with ringed sideroblasts (RARS); RA with excess of blasts (RAEB); refractory cytopenia with multilineage dysplasia (RCMD), refractory cytopenia with unilineage dysplasia (RCUD); unclassifiable myelodysplastic syndrome (MDS-U), myelodysplastic syndrome associated with an isolated del(5q) chromosome abnormality, therapy-related myeloid neoplasms and chronic myelomonocytic leukemia (CMML).

As used herein, "promyelocytic leukemia" or "acute promyelocytic leukemia" refers to a malignancy of the bone marrow in which there is a deficiency of mature blood cells in the myeloid line of cells and an excess of immature cells called promyelocytes. It is usually marked by an exchange of regions of chromosomes 15 and 17.

As used herein, "acute lymphocytic leukemia (ALL)", also known as "acute lymphoblastic leukemia" refers to a malignant disease caused by the abnormal growth and development of early nongranular white blood cells, or lymphocytes.

As used herein, "T-cell leukemia" refers to a disease in which certain cells of the lymphoid system called T lymphocytes or T cells are malignant. T cells are white blood cells that normally can attack virus-infected cells, foreign cells, and cancer cells and produce substances that regulate the immune response.

The term "relapsed" refers to a situation where patients who have had a remission of leukemia after therapy have a return of leukemia cells in the marrow and a decrease in normal blood cells.

The term "refractory or resistant" refers to a circumstance where patients, even after intensive treatment, have residual leukemia cells in their marrow.

The terms "co-administration" and "in combination with" include the administration of two therapeutic agents (for example, a compound provided herein and another anti-cancer agent) either simultaneously, concurrently or sequentially with no specific time limits. In one embodiment, both agents are present in the cell or in the patient's body at the same time or exert their biological or therapeutic effect at the same time. In one embodiment, the two therapeutic agents are in the same composition or unit dosage form. In another embodiment, the two therapeutic agents are in separate compositions or unit dosage forms.

The term "the supportive care agent" refers to any substance that treats, prevents and/or manages an adverse effect from treatment with the solid form of Compound 1.

The term "biological therapy" refers to administration of biological therapeutics such as cord blood, stem cells, growth factors and the like.

As used herein, overall survival (OS) means the time from randomization in a clinical trial until death from any cause. As used herein, progression-free survival (PFS) means the time from randomization in a clinical trial until progression or death. As used herein, event-free survival (EFS) means the time from study entry until any treatment failure, including disease progression, treatment discontinuation for any reason, or death. As used herein, overall response rate (ORR) means the sum of the percentage of patients who achieve complete and partial responses. As used herein, duration of response (DoR) is the time from achieving a response until relapse or disease progression.

"Anti-cancer agents" refer to anti-metabolites (e.g., 5-fluoro-uracil, methotrexate, fludarabine), antimicrotubule agents (e.g., *vinca* alkaloids such as vincristine, vinblastine; taxanes such as paclitaxel, docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, JM-216 or satraplatin, CI-973), anthracyclines (e.g., doxorubicin, daunorubicin), antitumor antibiotics (e.g., mitomycin, idarubicin, adriamycin, daunomycin), topoisomerase inhibitors (e.g., etoposide, camptothecins), anti-angiogenesis agents (e.g. Sutent® and Bevacizumab) or any other cytotoxic agents, (estramustine phosphate, prednimustine), hormones or hormone agonists, antagonists, partial agonists or partial antagonists, kinase inhibitors, checkpoint inhibitors, and radiation treatment.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the diluent, excipient or carrier must be compatible with the other ingredients of the formulation and not deleterious to the recipient thereof.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

This disclosure relates to solid forms of Compound 1, which is 2-(4-chlorophenyl)-N-((2-(2,6-dioxopiperidin-3-yl)-1-oxoisoindolin-5-yl)methyl)-2,2-difluoroacetamide and tautomers thereof, as well as methods of using, and compositions comprising, a solid form of Compound 1. For example, the present disclosure encompasses the in vitro and in vivo use of a solid form of Compound 1, and the incorporation of a solid form of Compound 1 into pharmaceutical compositions and single unit dosage forms useful in the treatment and prevention of a variety of diseases and disorders.

6.2. Solid Forms of Compound 1

In one embodiment, provided herein are solid forms of Compound 1.

Compound 1 can be prepared using the methods as described in U.S. Pat. No. 9,499,514 and International Patent Publication No. WO 2016/007848, the disclosures of each which are incorporated herein by reference in their entireties.

The solid forms comprising Compound 1 include single-component and multiple-component forms, including crystal forms and amorphous forms. Particular embodiments herein provide single-component amorphous solid forms of Compound 1. Particular embodiments herein provide single-component crystalline solid forms of Compound 1. Particular embodiments herein provide multiple-component amorphous forms comprising Compound 1. Particular embodiments herein provide multiple-component crystalline solid forms comprising Compound 1.

The solid forms comprising Compound 1 can be prepared by the methods described herein, including the methods described in the Examples below, or by techniques known in the art, including heating, cooling, freeze drying, lyophilization, quench cooling the melt, rapid solvent evaporation, slow solvent evaporation, solvent recrystallization, antisolvent addition, slurry recrystallization, crystallization from the melt, desolvation, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid cooling, slow cooling, exposure to solvent and/or water, drying, including, e.g., vacuum drying, vapor diffusion, sublimation, grinding (including, e.g., cryo-grinding, solvent-drop grinding or liquid assisted grinding), microwave-induced precipitation, sonication-induced precipitation, laser-induced precipitation and precipitation from a supercritical fluid. The particle size of the resulting solid forms, which can vary, (e.g., from nanometer dimensions to millimeter dimensions), can be controlled, e.g., by varying crystallization conditions, such as, e.g., the rate of crystallization and/or the crystallization solvent system, or by particle-size reduction techniques, e.g., grinding, milling, micronizing or sonication.

While not intending to be bound by any particular theory, certain solid forms are characterized by physical properties, e.g., stability, solubility and dissolution rate, appropriate for pharmaceutical and therapeutic dosage forms. Moreover, while not wishing to be bound by any particular theory, certain solid forms are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art.

The solid forms provided herein (e.g., Form A, Form B, Form C, Form D, Form E and amorphous of Compound 1) may be characterized using a number of methods known to a person having ordinary skill in the art, including, but not limited to, single crystal X-ray diffraction, X-ray powder diffraction (MUD), microscopy (e.g., scanning electron microscopy (SEM)), thermal analysis (e.g., differential scanning calorimetry (DSC), thermal gravimetric analysis (TGA), and hot-stage microscopy), spectroscopy (e.g., infrared, Raman, and solid-state nuclear magnetic resonance), single differential thermal analysis (SDTA), high performance liquid chromatography coupled with mass spectroscopy (HPLC-MS), thermogravimetrical analysis coupled with single differential thermal analysis (TGA-SDTA), and thermogravimetric analysis coupled with mass spectroscopy (TGA-MS). The particle size and size distribution of the solid form provided herein may be determined by conventional methods, such as laser light scattering technique.

The purity of the solid forms provided herein may be determined by standard analytical methods, such as thin layer chromatography (TLC), gel electrophoresis, gas chromatography, high performance liquid chromatography (HPLC), and mass spectrometry (MS).

It should be understood that the numerical values of the peaks of an X-ray powder diffraction pattern may vary slightly from one machine to another or from one sample to another, and so the values quoted are not to be construed as absolute, but with an allowable variability, such as ±0.2 degrees two theta (° 2θ) (see United State Pharmacopoeia, page 2228 (2003)).

Certain embodiments herein provide compositions comprising one or more of the solid forms. Certain embodiments provide compositions of one or more solid forms in combination with other active ingredients. Certain embodiments provide methods of using these compositions in the treatment, prevention and/or management of diseases and disorders including, but not limited to, the diseases and disorders provided herein.

The solid forms provided herein may also comprise unnatural proportions of atomic isotopes at one or more of the atoms in Compound 1. For example, the compound may be radiolabeled with radioactive isotopes, such as for example tritium ($^3H$), or carbon-14 ($^{14}C$), or may be isotopically enriched, such as with deuterium ($^2H$), carbon-13 ($^{13}C$), or nitrogen-15 ($^{15}N$). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of Compound 1, whether radioactive or not, are intended to be encompassed within the scope of the embodiments provided herein. In some embodiments, there are provided isotopologues of Compound 1, for example, the isotopologues are deuterium, carbon-13, or nitrogen-15 enriched Compound 1.

The compound may be radiolabeled with radioactive isotopes, such as for example tritium ($^3H$), iodine-125 ($^{125}I$) sulfur-35 ($^{35}S$), or carbon-14 ($^{14}C$). Radiolabeled compounds are useful as therapeutic agents, e.g., cancer therapeutic agents, research reagents, e.g., binding assay reagents, and diagnostic agents, e.g., in vivo imaging agents. All isotopic variations of Compound 1 or isotopologies of Compound 1, whether radioactive or not, are intended to be encompassed within the scope of the embodiments provided herein.

6.2.1. Form a of Compound 1

In certain embodiments, provided herein is Form A of Compound 1.

In one embodiment, Form A is an anhydrous form of Compound 1. In another embodiment, Form A of Compound 1 is crystalline.

In certain embodiments, Form A is obtained by crystallization from certain solvent systems, for example, solvent systems comprising one or more of the following solvents: acetone and the solvent mixture of isopropanol and water at room temperature. In certain embodiments, Form A is obtained as an intermediate solid form from slurries at elevated temperature, for example about 50° C., in ethanol/water (1:1), acetone or acetonitrile.

In certain embodiments, Form A is substantially crystalline, as indicated by, e.g., X-ray powder diffraction measurements. In one embodiment, Form A of Compound 1 has an X-ray powder diffraction pattern substantially as shown in FIG. 2.

Figure 2:
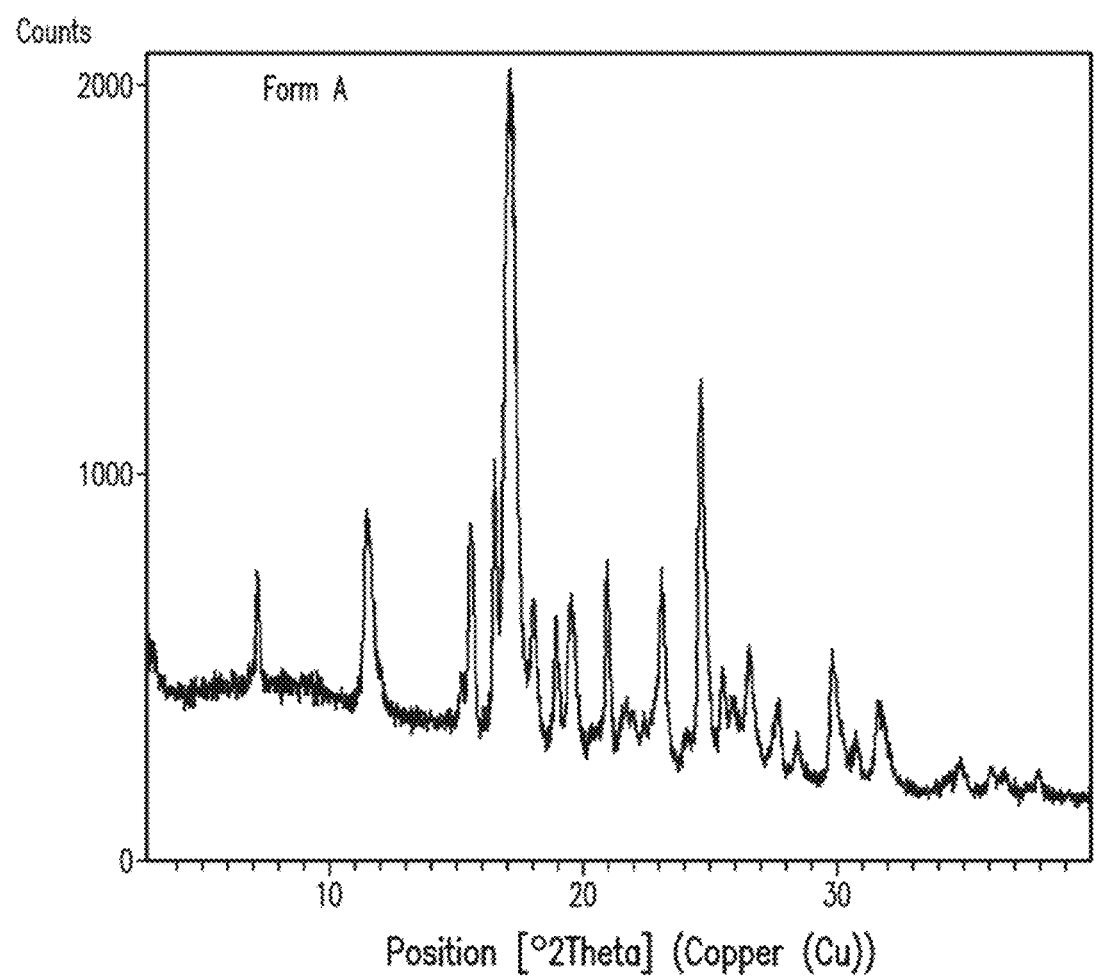
FIG. 2 depicts an X-ray powder diffractogram (XRPD) plot of Form A of Compound 1.

In one embodiment, Form A of Compound 1 has one or more characteristic X-ray powder diffraction peaks at a two-theta angle of approximately 11.5, 15.6, 16.6, 17.2, 18.1, 19.0, 19.6, 21.1, 23.2 or 24.8 degrees 2θ as depicted in FIG. 2. In another embodiment, Form A of Compound 1 has one, two, three or four characteristic X-ray powder diffraction peaks at a two-theta angle of approximately 15.6, 16.6, 17.2 or 24.8 degrees 2θ. In another embodiment, Form A of Compound 1 has one, two, three, four, five, six or seven characteristic X-ray powder diffraction peaks as set forth in Table 1. In another embodiment, Form A of Compound 1 has one, two, or three characteristic X-ray powder diffraction peaks as set forth in Table 1.

Figure 3:
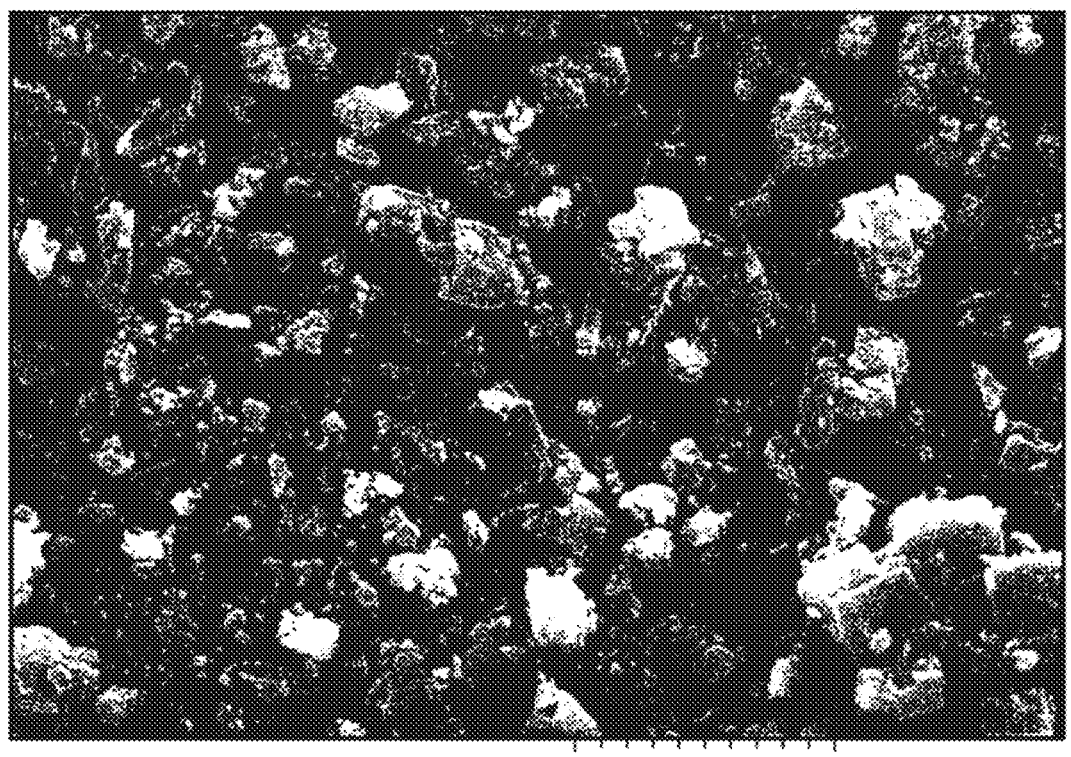
FIG. 3 depicts a SEM image of Form A of Compound 1.

In one embodiment, Form A of Compound 1 has the SEM picture as shown in FIG. 3.

Figure 4:
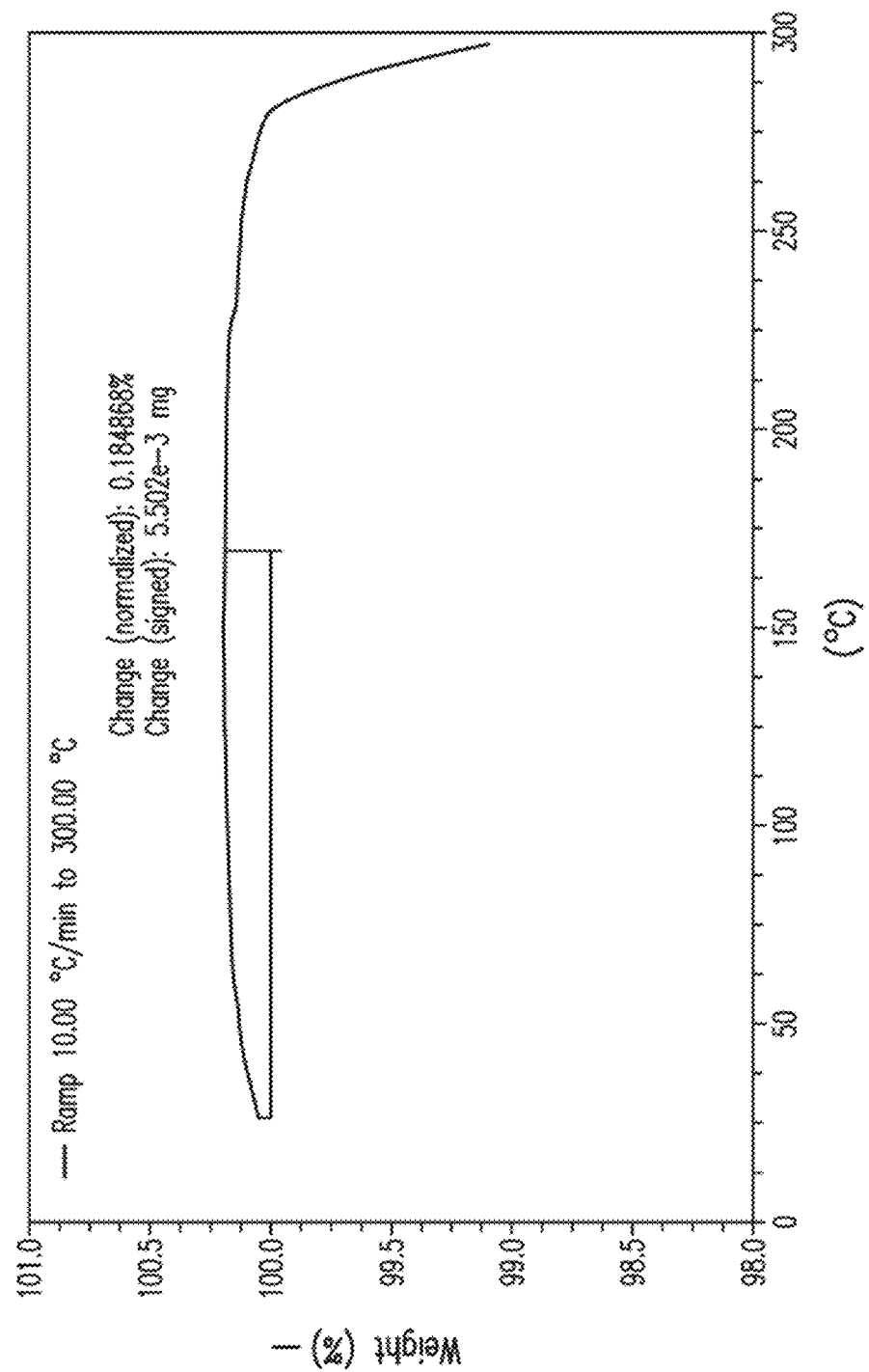
FIG. 4 depicts a thermogravimetrical analysis (TGA) plot of Form A of Compound 1.

In one embodiment, provided herein is a crystalline form of Compound 1 having a thermogravimetric (TGA) thermograph corresponding substantially to the representative TGA thermogram as depicted in FIG. 4. In certain embodiments, no TGA weight loss is observed for Form A.

Figure 5:
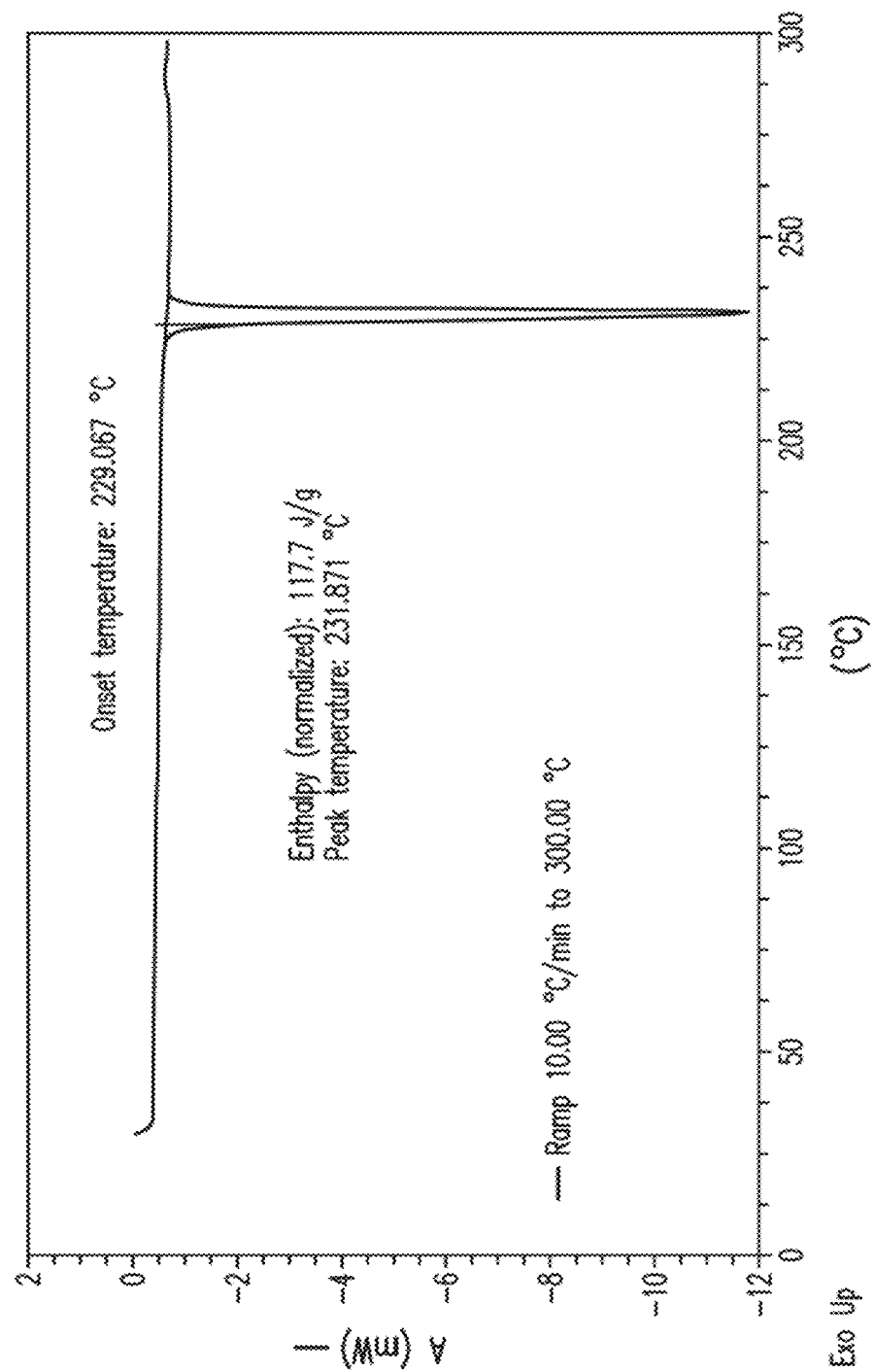
FIG. 5 depicts a differential scanning calorimetry (DSC) thermogram plot of Form A of Compound 1.

In one embodiment, provided herein is crystalline form A of Compound 1 having a DSC thermogram corresponding substantially as depicted in FIG. 5. In certain embodiments, Form A is characterized by a DSC plot comprising a melting event with an onset temperature of 229° C. and heat of fusion of 118 J/g.

In certain embodiments, Form A is characterized by dynamic vapor sorption analysis. A representative dynamic vapor sorption (DVS) isotherm plot is shown in FIG. 6. In certain embodiments, when the relative humidity ("RH") is increased from about 0% to about 90% RH, Form A exhibits less than 1.5%, less than 1.2% or about 1.2% w/w water uptake. In certain embodiments, Form A comprises less than 0.1% water as determined in a coulometric Karl Fischer (KF) titrator equipped with an oven sample processor set at 225° C.

In certain embodiments, no significant degradation or residual solvent for Form A is observed by $^1$H NMR (FIG. 7).

In certain embodiments, Form A of Compound 1 is characterized by its stability profile upon compression. In certain embodiments, Form A is stable, e.g., its XRPD pattern remains substantially unchanged with broader diffraction peaks, upon application of 2000-psi pressure for about 1 minute (FIG. 8).

In still another embodiment, Form A of Compound 1 is substantially pure. In certain embodiments, the substantially pure Form A of Compound 1 is substantially free of other solid forms, e.g., amorphous form. In certain embodiments, the purity of the substantially pure Form A of Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

Certain embodiments herein provide Form A of Compound 1 which is substantially pure. Certain embodiments herein provide Form A of Compound 1 which is substantially free of other solid forms comprising Compound 1 including, e.g., Forms B, C, D, E and/or an amorphous solid form comprising Compound 1 as provided herein. Certain embodiments herein provide Form A as a mixture of solid forms comprising Compound 1, including, e.g., a mixture comprising one or more of the following: Forms B, C, D, E and an amorphous solid form comprising Compound 1 as provided herein.

6.2.2. Form B of Compound 1

In certain embodiments, provided herein is anhydrous Form B of Compound 1.

In certain embodiments, Form B is obtained by anti-solvent recrystallization from certain solvent systems, for example, solvent systems comprising one or more of the following solvents: methanol/water, DMSO/isopropanol, DMSO/toluene, and DMSO/water. In certain embodiments, Form B is obtained by cooling recrystallization from THF/water (1:1).

In certain embodiments, Form B is crystalline, as indicated by, e.g., X-ray powder diffraction measurements. In one embodiment, Form B of Compound 1 has an X-ray powder diffraction pattern substantially as shown in FIG. 9.

In one embodiment, Form B of Compound 1 has one or more characteristic X-ray powder diffraction peaks at a two-theta angle of approximately 15.4, 16.3, 16.7, 17.7, 20.4, 25.6 or 27.5, degrees 2θ as depicted in FIG. 9. In another embodiment, Form B of Compound 1 has one, two, three or four characteristic X-ray powder diffraction peaks at a two-theta angle of approximately 16.7, 25.6, 15.4 or 16.3 degrees 2θ. In another embodiment, Form B of Compound 1 has one, two, three, four, five, six or seven characteristic X-ray powder diffraction peaks as set forth in Table 2. In another embodiment, Form B of Compound 1 has one, two, or three characteristic X-ray powder diffraction peaks as set forth in Table 2.

In one embodiment, Form B of Compound 1 has the SEM picture as shown in FIG. 10. In one embodiment, provided herein is a crystalline form of Compound 1 having a thermogravimetric (TGA) thermograph corresponding substantially to the representative TGA thermogram as depicted in FIG. 11. In certain embodiments, Form B shows no TGA weight loss below 170° C. In certain embodiments, Form B shows a TGA weight loss of 0.4% between 170~230° C.

In one embodiment, provided herein is crystalline Form B of Compound 1 having a DSC thermogram corresponding substantially as depicted in FIG. 12. In certain embodiments, Form B is characterized by a DSC plot comprising a melt/recrystallization event at 219~224° C. and a major melting event with a peak temperature of 231° C.

In certain embodiments, Form B is characterized by dynamic vapor sorption analysis. A representative dynamic vapor sorption (DVS) isotherm plot is shown in FIG. 13. In certain embodiments, when the relative humidity ("RH") is increased from about 0% to about 90% RH, Form B exhibits about 1.4% w/w water uptake. In certain embodiments, Form B comprises less than 0.1% water as determined in a coulometric Karl Fischer (KF) titrator equipped with an oven sample processor set at 225° C.

In certain embodiments, Form B shows no significant degradation or residual solvent by $^1$H NMR (FIG. 14).

In certain embodiments, Form B of Compound 1 is characterized by its stability profile upon compression. In certain embodiments, Form B is stable, e.g., its XRPD pattern remains substantially unchanged with broader diffraction peaks, upon application of 2000-psi pressure for about 1 minute (FIG. 15).

In still another embodiment, Form B of Compound 1 is substantially pure. In certain embodiments, the substantially pure Form B of Compound 1 is substantially free of other solid forms, e.g., amorphous form. In certain embodiments, the purity of the substantially pure Form B of Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

Certain embodiments herein provide Form B of Compound 1 which is substantially pure. Certain embodiments herein provide Form B of Compound 1 which is substantially free of other solid forms comprising Compound 1 including, e.g., Forms A, C, D, E, and/or an amorphous solid form comprising Compound 1 as provided herein. Certain embodiments herein provide Form B as a mixture of solid forms comprising Compound 1, including, e.g., a mixture comprising one or more of the following: Forms A, C, D, E, and an amorphous solid form comprising Compound 1 as provided herein.

6.2.3. Form C of Compound 1

In certain embodiments, provided herein is anhydrous Form C of Compound 1. In certain embodiments, Form C is the most thermodynamically stable anhydrate among the crystal forms of Compound 1 provided herein.

In certain embodiments, Form C is obtained by slurrying Compound 1 in certain solvent systems, for example, solvent systems comprising one or more of the following solvents: acetonitrile/water, acetone, or ethanol/water for an extended period of time.

In certain aspects, Form C is obtained by slurrying Form B (1× wt) in acetone (30×vol) at an elevated temperature, for example, from 60-80° C. or 70-75° C. for at least 24 hours, and cooling the mixture to room temperature. In one aspect, the slurrying is conducted at a temperature of 70-75° C. under nitrogen pressure of 50-55-psi. In one aspect, the mixture is cooled to room temperature over at least 6 hours.

In certain embodiments, Form C is crystalline, as indicated by, e.g., X-ray powder diffraction measurements. In one embodiment, Form C of Compound 1 has an X-ray powder diffraction pattern substantially as shown in FIG. 16.

In one embodiment, Form C of Compound 1 has one or more characteristic X-ray powder diffraction peaks at a two-theta angle of approximately 7.4, 11.5, 15.8, 16.7, 16.9, 17.7, 18.4, 19.2, 19.5, 21.1, 23.4, 24.7, or 29.9, degrees 2θ as depicted in FIG. 16. In another embodiment, Form C of Compound 1 has one, two, three or four characteristic X-ray powder diffraction peaks at a two-theta angle of approximately 16.7, 16.9, 17.7 or 24.7 degrees 2θ. In another embodiment, Form C of Compound 1 has one, two, three, four, five, six or seven characteristic X-ray powder diffraction peaks as set forth in Table 3. In another embodiment, Form C of Compound 1 has one, two, or three characteristic X-ray powder diffraction peaks as set forth in Table 3.

In one embodiment, Form C of Compound 1 has the SEM picture as shown in FIG. 17. In one embodiment, provided herein is a crystalline form of Compound 1 having a thermogravimetric (TGA) thermograph corresponding substantially to the representative TGA thermogram as depicted in FIG. 18. In certain embodiments, Form C shows no TGA weight loss.

In one embodiment, provided herein is crystalline Form C of Compound 1 having a DSC thermogram corresponding substantially as depicted in FIG. 19. In certain embodiments, Form C is characterized by a DSC plot comprising melting event with an onset temperature of 232° C. and heat of fusion of 126 J/g.

In certain embodiments, Form C is characterized by dynamic vapor sorption analysis. A representative dynamic vapor sorption (DVS) isotherm plot is shown in FIG. 20. In certain embodiments, when the relative humidity ("RH") is increased from about 0% to about 90% RH, Form C exhibits about 0.6% w/w water uptake. In certain embodiments, Form C comprises less than 0.1% water as determined in a coulometric Karl Fischer (KF) titrator equipped with an oven sample processor set at 225° C.

In certain embodiments, Form C shows no significant degradation or residual solvent by $^1$H NMR (FIG. 21).

In certain embodiments, Form C of Compound 1 is characterized by its stability profile upon compression. In certain embodiments, Form C is stable, e.g., its XRPD pattern remains substantially unchanged with broader diffraction peaks, upon application of 2000-psi pressure for about 1 minute (FIG. 22).

In still another embodiment, Form C of Compound 1 is substantially pure. In certain embodiments, the substantially pure Form C of Compound 1 is substantially free of other solid forms, e.g., amorphous form. In certain embodiments, the purity of the substantially pure Form C of Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

Certain embodiments herein provide Form C of Compound 1 which is substantially pure. Certain embodiments herein provide Form C of Compound 1 which is substantially free of other solid forms comprising Compound 1 including, e.g., Forms A, B, D, E, and/or an amorphous solid form comprising Compound 1 as provided herein. Certain embodiments herein provide Form C as a mixture of solid forms comprising Compound 1, including, e.g., a mixture comprising one or more of the following: Forms A, B, D, E, and an amorphous solid form comprising Compound 1 as provided herein.

6.2.4. Form D of Compound 1

In certain embodiments, provided herein is Form D of Compound 1. In certain embodiments, Form D of Compound 1 is a DMSO solvate.

In certain embodiments, Form D is obtained by heating Form B in DMSO/methyl isobutyl ketone and cooling the solution.

In certain embodiments, Form D is crystalline, as indicated by, e.g., X-ray powder diffraction measurements. In one embodiment, Form D of Compound 1 has an X-ray powder diffraction pattern substantially as shown in FIG. 23.

In one embodiment, Form D of Compound 1 has one or more characteristic X-ray powder diffraction peaks at a two-theta angle of approximately 14.1, 14.3, 18.8, 19.1, 23.6 or 24.0 degrees 2θ as depicted in FIG. 23. In another embodiment, Form D of Compound 1 has one, two, three or four characteristic X-ray powder diffraction peaks at a two-theta angle of approximately 14.1, 14.3, 18.8 or 19.1 degrees 2θ. In another embodiment, Form D of Compound 1 has one, two, three, four, five, six or seven characteristic X-ray powder diffraction peaks as set forth in Table 4. In another embodiment, Form D of Compound 1 has one, two, or three characteristic X-ray powder diffraction peaks as set forth in Table 4.

In one embodiment, provided herein is a crystalline form of Compound 1 having a thermogravimetric (TGA) thermograph corresponding substantially to the representative TGA thermogram as depicted in FIG. 24. In certain embodiments, Form D shows TGA weight loss of about 14.1% up to 140° C.

In certain embodiments, Form D comprises DMSO in about 14.3 wt % as measured by gas chromatography.

In still another embodiment, Form D of Compound 1 is substantially pure. In certain embodiments, the substantially pure Form D of Compound 1 is substantially free of other solid forms, e.g., amorphous form. In certain embodiments, the purity of the substantially pure Form D of Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

Certain embodiments herein provide Form D of Compound 1 which is substantially pure. Certain embodiments herein provide Form D of Compound 1 which is substantially free of other solid forms comprising Compound 1 including, e.g., Forms A, B, C, E, and/or an amorphous solid form comprising Compound 1 as provided herein. Certain embodiments herein provide Form D as a mixture of solid forms comprising Compound 1, including, e.g., a mixture comprising one or more of the following: Forms A, B, C, E, and an amorphous solid form comprising Compound 1 as provided herein.

6.2.5. Form E of Compound 1

In certain embodiments, provided herein is Form E of Compound 1. In certain embodiments, Form E of Compound 1 is a DMSO solvate.

In certain embodiments, Form E is obtained from Form C in DMSO/MIBK or DMSO/IPA or DMSO/anisole at room temperature.

In certain embodiments, Form E is crystalline, as indicated by, e.g., X-ray powder diffraction measurements. In one embodiment, Form E of Compound 1 has an X-ray powder diffraction pattern substantially as shown in FIG. 25.

In one embodiment, Form E of Compound 1 has one or more characteristic X-ray powder diffraction peaks at a two-theta angle of approximately 10.5, 12.5, 16.1, 17.0, 18.5, 21.2, 21.7, 22.6, 22.9, 23.4, 23.8, 24.1, 25.1 or 26.7, degrees 2θ as depicted in FIG. 25. In another embodiment, Form E of Compound 1 has one, two, three or four characteristic X-ray powder diffraction peaks at a two-theta angle of approximately 16.1, 17.0, 21.2 or 22.9 degrees 2θ. In another embodiment, Form E of Compound 1 has one, two, three, four, five, six or seven characteristic X-ray powder diffraction peaks as set forth in Table 5. In another embodiment, Form E of Compound 1 has one, two, or three characteristic X-ray powder diffraction peaks as set forth in Table 5.

In one embodiment, provided herein is a crystalline form of Compound 1 having a thermogravimetric (TGA) thermograph corresponding substantially to the representative TGA thermogram as depicted in FIG. 26. In certain embodiments, Form E shows TGA weight loss of about 19.4% up to 120° C. In certain embodiments, Form E shows additional weight loss of 24.9% between 120 and 220° C.

In one embodiment, Form E of Compound 1 is substantially pure. In certain embodiments, the substantially pure Form E of Compound 1 is substantially free of other solid forms, e.g., amorphous form. In certain embodiments, the purity of the substantially pure Form E of Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

Certain embodiments herein provide Form E of Compound 1 which is substantially pure. Certain embodiments herein provide Form E of Compound 1 which is substantially free of other solid forms comprising Compound 1 including, e.g., Forms A, B, C, D and/or an amorphous solid form comprising Compound 1 as provided herein. Certain embodiments herein provide Form C as a mixture of solid forms comprising Compound 1, including, e.g., a mixture comprising one or more of the following: Forms A, B, C, D and an amorphous solid form comprising Compound 1 as provided herein.

6.2.6. Amorphous Compound 1

In certain embodiments, provided herein is amorphous Compound 1.

In certain embodiments, provided herein are methods for making the amorphous form by heating Compound 1 in THF and water, and lyophilizing the solution. In one embodiment the lyophilizing comprises freezing the solution and removing the solvent under reduced pressure.

In one embodiment, provided herein is an amorphous solid form of Compound 1 having a DSC thermogram as depicted in FIG. 27.

In one embodiment, amorphous Compound 1 has an X-ray powder diffraction pattern substantially as shown in FIG. 28.

In one embodiment, amorphous Compound 1 has a $^1$H NMR spectrum substantially as shown in FIG. 29.

In still another embodiment, amorphous Compound 1 is substantially pure. In certain embodiments, the substantially pure amorphous Compound 1 is substantially free of other solid forms, e.g., Form A, Form B, Form C, Form D or Form E. In certain embodiments, the purity of the substantially pure amorphous Compound 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

6.2.7. Isotopologues of Compound 1

Also provided herein are isotopically enriched analogs of the compounds ("isotopologues") provided herein. Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., *Food Cosmet. Toxicol.*, 20: 393 (1982); Lijinsky et. al., *J. Nat. Cancer Inst.*, 69: 1127 (1982); Mangold et. al., *Mutation Res.* 308: 33 (1994); Gordon et. al., *Drug Metab. Dispos.*, 15: 589 (1987); Zello et. al., *Metabolism*, 43: 487 (1994); Gately et. al., *J. Nucl. Med.*, 27: 388 (1986); Wade D, *Chem. Biol. Interact.* 117: 191 (1999).

Without being limited by any particular theory, iotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6)

decrease the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g, Foster et al., *Adv. Drug Res.*, vol. 14, pp. 1-36 (1985); Kushner et al., *Can. J. Physiol. Pharmacol.*, vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. Without being limited by a particular theory, high DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects.

Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, will provide a similar kinetic isotope effects.

6.3. Methods of Treatment

In one embodiment, provided herein is a method of treating and preventing cancer, which comprises administering to a patient a solid form of Compound 1 provided herein.

In another embodiment, provided herein is method of managing cancer, which comprises administering to a patient a solid form of Compound 1 provided herein.

Also provided herein are methods of treating patients who have been previously treated for cancer but are non-responsive to standard therapies, as well as those who have not previously been treated. The invention also encompasses methods of treating patients regardless of patient's age, although some diseases or disorders are more common in certain age groups. The invention further encompasses methods of treating patients who have undergone surgery in an attempt to treat the disease or condition at issue, as well as those who have not. Because patients with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

As used herein, the term "cancer" includes, but is not limited to, solid tumors and blood borne tumors. The term "cancer" refers to disease of skin tissues, organs, blood, and vessels, including, but not limited to, cancers of the bladder, bone, blood, brain, breast, cervix, chest, colon, endrometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant giolma, anaplastic astrocytoma, anaplastic oligodendroglioma, neuroendocrine tumor, rectal adenocarcinoma, colorectal cancer, including stage 3 and stage 4 colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma.

In certain embodiments, the cancer is a solid tumor. In certain embodiments, the solid tumor is metastatic. In certain embodiments, the solid tumor is drug-resistant. In certain embodiments, the solid tumor is hepatocellular carcinoma, prostate cancer, ovarian cancer, or glioblastoma.

In certain embodiments, the cancer is a blood borne tumor. In certain embodiments, the blood borne tumor is metastatic. In certain embodiments, the blood borne tumor is drug resistant. In certain embodiments, the cancer is leukemia.

In one embodiment, methods provided herein encompass treating, preventing and/or managing various types of leukemias such as chronic lymphocytic leukemia (CLL), chronic myelocytic leukemia (CML), acute lymphoblastic leukemia (ALL), acute myeloid leukemia (AML), and acute myeloblastic leukemia (AML) by administering a therapeutically effective amount of a solid form of Compound 1 provided herein.

In some embodiments, the methods provided herein encompass treating, preventing and/or managing acute leukemia in a subject. In some embodiments, the acute leukemia is acute myeloid leukemia (AML), which includes, but is not limited to, undifferentiated AML (M0), myeloblastic leukemia (M1), myeloblastic leukemia (M2), promyelocytic leukemia (M3 or M3 variant (M3V)), myelomonocytic leukemia (M4 or M4 variant with eosinophilia (M4E)), monocytic leukemia (M5), erythroleukemia (M6), and megakaryoblastic leukemia (M7). In one embodiment, the acute myeloid leukemia is undifferentiated AML (M0). In one embodiment, the acute myeloid leukemia is myeloblastic leukemia (M1). In one embodiment, the acute myeloid leukemia is myeloblastic leukemia (M2). In one embodiment, the acute myeloid leukemia is promyelocytic leukemia (M3 or M3 variant (M3V)). In one embodiment, the acute myeloid leukemia is myelomonocytic leukemia (M4 or M4 variant with eosinophilia (M4E)). In one embodiment, the acute myeloid leukemia is monocytic leukemia (M5). In one embodiment, the acute myeloid leukemia is erythroleukemia (M6). In one embodiment, the acute myeloid leukemia is megakaryoblastic leukemia (M7).

In certain embodiments, the methods of treating, preventing and/or managing acute myeloid leukemia in a subject comprise the step of administering to the subject an amount of a solid form of Compound 1 provided herein effective to treat, prevent and/or manage acute myeloid leukemia alone or in combination.

In one embodiment, provided herein are methods of treating, preventing and/or managing acute myeloid leukemia by intravenous administration of a solid form of Compound 1. In one embodiment, the solid form of Compound 1 is dissolved in water to form an aqueous solution for intravenous administration in methods of treating, preventing and/or managing acute myeloid leukemia provided herein.

In one embodiment, provided herein are methods of treating, preventing and/or managing acute myeloid leukemia by intravenous administration of Form C of Compound 1. In one embodiment, Form C of Compound 1 is dissolved in water to form an aqueous solution for intravenous administration in methods of treating, preventing and/or managing acute myeloid leukemia provided herein.

In some embodiments, the methods comprise the step of administering to the subject a solid form of Compound 1 provided herein in combination with a second active agent in amounts effective to treat, prevent and/or manage acute myeloid leukemia.

In some embodiments, the methods provided herein encompass treating, preventing and/or managing acute lymphocytic leukemia (ALL) in a subject. In some embodiments, acute lymphocytic leukemia includes leukemia that originates in the blast cells of the bone marrow (B-cells), thymus (T-cells), and lymph nodes. The acute lymphocytic leukemia can be categorized according to the French-American-British (FAB) Morphological Classification Scheme as L1—Mature-appearing lymphoblasts (T-cells or pre-B-cells), L2—Immature and pleomorphic (variously shaped) lymphoblasts (T-cells or pre-B-cells), and L3—Lymphoblasts (B-cells; Burkitt's cells). In one embodiment, the acute lymphocytic leukemia originates in the blast cells of the bone marrow (B-cells). In one embodiment, the acute lymphocytic leukemia originates in the thymus (T-cells). In one embodiment, the acute lymphocytic leukemia originates in the lymph nodes. In one embodiment, the acute lymphocytic leukemia is L1 type characterized by mature-appearing lymphoblasts (T-cells or pre-B-cells). In one embodiment, the acute lymphocytic leukemia is L2 type characterized by immature and pleomorphic (variously shaped) lymphoblasts (T-cells or pre-B-cells). In one embodiment, the acute lymphocytic leukemia is L3 type characterized by lymphoblasts (B-cells; Burkitt's cells). In certain embodiments, the acute lymphocytic leukemia is T-cell leukemia. In one embodiment, the T-cell leukemia is peripheral T-cell leukemia. In another embodiment, the T-cell leukemia is T-cell lymphoblastic leukemia. In another embodiment, the T-cell leukemia is cutaneous T-cell leukemia. In another embodiment, the T-cell leukemia is adult T-cell leukemia. Thus, the methods of treating, preventing and/or managing acute lymphocytic leukemia in a subject comprise the step of administering to the subject an amount of a solid form of Compound 1 provided herein effective to treat, prevent and/or manage acute lymphocytic leukemia alone or in combination with a second active agent. In some embodiments, the methods comprise the step of administering to the subject a solid form of Compound 1 provided herein in combination with a second active agent in amounts effective to treat, prevent and/or manage acute lymphocytic leukemia.

In some embodiments, the methods provided herein encompass treating, preventing and/or managing chronic myelogenous leukemia (CML) in a subject. The methods comprise the step of administering to the subject an amount of a solid form of Compound 1 provided herein effective to treat, prevent and/or manage chronic myelogenous leukemia. In some embodiments, the methods comprise the step of administering to the subject a solid form of Compound 1 provided herein in combination with a second active agent in amounts effective to treat, prevent and/or manage chronic myelogenous leukemia.

In some embodiments, the methods provided herein encompass treating, preventing and/or managing chronic lymphocytic leukemia (CLL) in a subject. The methods comprise the step of administering to the subject an amount of a solid form of Compound 1 provided herein effective to treat, prevent and/or manage chronic lymphocytic leukemia. In some embodiments, the methods comprise the step of administering to the subject a solid form of Compound 1 provided herein in combination with a second active agent in amounts effective to treat, prevent and/or manage chronic lymphocytic leukemia.

In certain embodiments, provided herein are methods of treating, preventing, and/or managing disease in patients with impaired renal function. In certain embodiments, provided herein are method of treating, preventing, and/or managing cancer in patients with impaired renal function. In certain embodiments, provided herein are methods of providing appropriate dose adjustments for patients with impaired renal function due to, but not limited to, disease, aging, or other patient factors.

In certain embodiments, provided herein are methods of treating, preventing, and/or managing lymphoma, including non-Hodgkin's lymphoma. In some embodiments, provided herein are methods for the treatment and/or management of non-Hodgkin's lymphoma (NHL), including but not limited to, diffuse large B-cell lymphoma (DLBCL), using prognostic factors.

In certain embodiments, provided herein are methods of treating, preventing, and/or managing multiple myeloma, including relapsed/refractory multiple myeloma in patients with impaired renal function or a symptom thereof, comprising administering a therapeutically effective amount of a solid form of Compound 1 provided herein to a patient having relapsed/refractory multiple myeloma with impaired renal function.

In one embodiment, provided herein are methods of treating, preventing, and/or managing a myelodysplastic syndrome (MDS) by administering a therapeutically active amount of a solid form of Compound 1 provided herein. In one embodiment, the MDS is relapsed, resistant or refractory MDS. In one embodiment, MDS is selected from refractory anemia (RA); RA with ringed sideroblasts (RARS); RA with excess of blasts (RAEB); refractory cytopenia with multilineage dysplasia (RCMD), refractory cytopenia with unilineage dysplasia (RCUD); unclassifiable myelodysplastic syndrome (MDS-U), myelodysplastic syndrome associated with an isolated del(5q) chromosome abnormality, therapy-related myeloid neoplasms and chronic myelomonocytic leukemia (CMML).

In certain embodiments, a therapeutically or prophylactically effective amount of a solid form of Compound 1 provided herein is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, from about 0.05 to about 10 mg per day, from about 0.05 to about 5 mg per day, from about 0.1 to about 5 mg per day, or from about 0.5 to about 5 mg per day.

In certain embodiments, the therapeutically or prophylactically effective amount is about 0.1, about 0.2, about 0.5, about 1, about 2, about 3, about 4, about 5, about 6, about 7, about 8, about 9, about 10, about 15, about 20, about 25, about 30, about 40, about 45, about 50, about 60, about 70, about 80, about 90, about 100, or about 150 mg per day. In some such embodiments, the therapeutically or prophylactically effective amount is about 2, about 3, about 4, about 5, about 6 or about 7 mg per day.

In one embodiment, the recommended daily dose range of a solid form of Compound 1 provided herein, for the conditions described herein lie within the range of from about 0.05 mg to about 50 mg per day, preferably given as a single once-a-day dose, or in divided doses throughout a day. In some embodiments, the dosage ranges from about 1 mg to about 50 mg per day. In other embodiments, the dosage ranges from about 0.5 to about 5 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In a specific embodiment, the recommended starting dosage may be 0.1, 0.5, 1, 2, 3, 4, 5, 10, 15, 20, 25 or 50 mg per day. In another embodiment, the recommended starting dosage may be 0.1, 0.5, 1, 2, 3, 4, or 5 mg per day. The dose may be escalated to 15, 20, 25, 30, 35, 40, 45 and 50 mg/day. In a specific embodiment, a solid form of Compound 1 can be administered in an amount of about 25 mg/day to patients with leukemia, including AML. In a particular embodiment, a solid form of Compound 1 can be administered in an amount of about 10 mg/day to patients with leukemia, including AML. In a particular embodiment, a solid form of Compound 1 can be administered in an amount of about 5 mg/day to patients with leukemia, including AML. In a particular embodiment, a solid form of Compound 1 can be administered in an amount of about 4 mg/day to patients with leukemia, including AML. In a particular embodiment, a solid form of Compound 1 provided herein can be administered in an amount of about 3 mg/day to patients with leukemia, including AML. In a particular embodiment, Compound 1 provided herein can be administered in an amount of about 2 mg/day to patients with leukemia, including AML. In a particular embodiment, Compound 1 provided herein can be administered in an amount of about 1 mg/day to patients with leukemia, including AML. In a particular embodiment, Compound 1 provided herein can be administered in an amount of about 0.5 mg/day to patients with leukemia, including AML.

In a specific embodiment, a solid form of Compound 1 can be administered in an amount of about 25 mg/day to patients with MDS. In a particular embodiment, a solid form of Compound 1 can be administered in an amount of about 10 mg/day to patients with MDS. In a particular embodiment, a solid form of Compound 1 can be administered in an amount of about 5 mg/day to patients with MDS. In a particular embodiment, a solid form of Compound 1 can be administered in an amount of about 4 mg/day to patients with MDS. In a particular embodiment, a solid form of Compound 1 provided herein can be administered in an amount of about 3 mg/day to patients with MDS. In a particular embodiment, a solid form of Compound 1 provided herein can be administered in an amount of about 2 mg/day to patients with MDS. In a particular embodiment, a solid form of Compound 1 provided herein can be administered in an amount of about 1 mg/day to patients with MDS. In a particular embodiment, a solid form of Compound 1 provided herein can be administered in an amount of about 0.5 mg/day to patients with MDS.

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, from about 0.01 to about 1 mg/kg/day, or from about 0.01 to about 0.05 mg/kg/day.

The administered dose can also be expressed in units other than mg/kg/day. For example, doses for parenteral administration can be expressed as $mg/m^2/day$. One of ordinary skill in the art would readily know how to convert doses from mg/kg/day to $mg/m^2/day$ to given either the height or weight of a subject or both (see, www.fda.gov/cder/cancer/animalframe.htm). For example, a dose of 1 mg/kg/day for a 65 kg human is approximately equal to 38 $mg/m^2/day$.

In certain embodiments, the amount of a solid form of Compound 1 administered is sufficient to provide a plasma concentration of the compound at steady state, ranging from about 0.001 to about 500 μM, about 0.002 to about 200 μM, about 0.005 to about 100 μM, about 0.01 to about 50 μM, from about 1 to about 50 μM, about 0.02 to about 25 μM, from about 0.05 to about 20 μM, from about 0.1 to about 20 μM, from about 0.5 to about 20 μM, or from about 1 to about 20 μM.

In other embodiments, the amount of a solid form of Compound 1 administered is sufficient to provide a plasma concentration of the compound at steady state, ranging from about 5 to about 100 nM, about 5 to about 50 nM, about 10 to about 100 nM, about 10 to about 50 nM or from about 50 to about 100 nM.

As used herein, the term "plasma concentration at steady state" is the concentration reached after a period of administration of a solid form of Compound 1 provided herein. Once steady state is reached, there are minor peaks and troughs on the time dependent curve of the plasma concentration of the solid form.

In certain embodiments, the amount of a solid form of Compound 1 administered is sufficient to provide a maximum plasma concentration (peak concentration) of the compound, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In certain embodiments, the amount of a solid form of Compound 1 administered is sufficient to provide a minimum plasma concentration (trough concentration) of the compound, ranging from about 0.001 to about 500 µM, about 0.002 to about 200 µM, about 0.005 to about 100 µM, about 0.01 to about 50 µM, from about 1 to about 50 µM, about 0.01 to about 25 µM, from about 0.01 to about 20 µM, from about 0.02 to about 20 µM, from about 0.02 to about 20 µM, or from about 0.01 to about 20 µM.

In certain embodiments, the amount of a solid form of Compound 1 administered is sufficient to provide an area under the curve (AUC) of the compound, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

In certain embodiments, the patient to be treated with one of the methods provided herein has not been treated with anticancer therapy prior to the administration of a solid form of Compound 1 provided herein. In certain embodiments, the patient to be treated with one of the methods provided herein has been treated with anticancer therapy prior to the administration of a solid form of Compound 1 provided herein. In certain embodiments, the patient to be treated with one of the methods provided herein has developed drug resistance to the anticancer therapy.

The methods provided herein encompass treating a patient regardless of patient's age, although some diseases or disorders are more common in certain age groups.

Depending on the disease to be treated and the subject's condition, a solid form of Compound 1 provided herein may be administered by parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. The solid forms of Compound 1 may be formulated, alone or together, in suitable dosage unit with pharmaceutically acceptable excipients, carriers, adjuvants and vehicles, appropriate for each route of administration.

In another embodiment, the solid form of Compound 1 is administered parenterally. In certain embodiments, an aqueous solution containing one or more solid forms of Compound 1 is administered parenterally.

In yet another embodiment, a solid form of Compound 1 provided herein is administered intravenously. In certain embodiments, an aqueous solution containing one or more solid forms of Compound 1 is administered intravenously.

The solid forms of Compound 1 provided herein can be delivered as a single dose such as, e.g., a single bolus injection, or over time, such as, e.g., continuous infusion over time or divided bolus doses over time. The solid forms of Compound 1 can be administered repeatedly if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, *Journal of the National Cancer Institute* 92(3): 205-216 (2000). Stable disease or lack thereof is determined by methods known in the art such as evaluation of patient symptoms, physical examination, visualization of the tumor that has been imaged using X-ray, CAT, PET, or MM scan and other commonly accepted evaluation modalities.

The solid forms of Compound 1 provided herein can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as a solid form of Compound 1, is administered once or more than once each day, for example, for a period of time. The term "continuous" is intended to mean that a therapeutic compound, such as a solid form of Compound 1, is administered daily for an uninterrupted period of at least 10 days to 52 weeks. The term "intermittent" or "intermittently" as used herein is intended to mean stopping and starting at either regular or irregular intervals. For example, intermittent administration of the solid form of Compound 1 is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as a solid form of Compound 1, is administered daily or continuously but with a rest period. In some such embodiments, administration is once a day for two to six days, then a rest period with no administration for five to seven days. In some other such embodiments, administration is once a day for the first two to five or ten days of a 28 day cycle, followed by a rest period with no administration for the rest of the 28 day cycle.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, a solid form of Compound 1 is administered once a day. In another embodiment, a solid form of Compound 1 is administered twice a day. In yet another embodiment, a solid form of Compound 1 provided herein is administered three times a day. In still another embodiment, a solid form of Compound 1 provided herein is administered four times a day.

In certain embodiments, a solid form of Compound 1 provided herein is administered once per day from one day to six months, from one week to three months, from one week to four weeks, from one week to three weeks, or from one week to two weeks. In certain embodiments, a solid form of Compound 1 provided herein is administered once per day for one week, two weeks, three weeks, or four weeks. In one embodiment, a solid form of Compound 1 provided herein is administered once per day for 4 days. In one embodiment, a solid form of Compound 1 provided herein is administered once per day for 5 days. In one embodiment, a solid form of Compound 1 provided herein is administered once per day for 6 days. In one embodiment, a solid form of Compound 1 provided herein is administered once per day for one week. In another embodiment, a solid form of Compound 1 provided herein is administered once per day for two weeks. In yet another embodiment, a solid form of Compound 1 provided herein is administered once per day for three weeks. In still another embodiment, a solid form of Compound 1 provided herein is administered once per day for four weeks.

6.3.1. Combination Therapy With A Second Active Agent

The solid forms of Compound 1 provided herein can also be combined or used in combination with other therapeutic agents useful in the treatment and/or prevention of cancer described herein.

In one embodiment, provided herein is a method of treating, preventing, and/or managing cancer, comprising administering to a patient a solid form of Compound 1 provided herein in combination with one or more second active agents, and optionally in combination with radiation therapy, blood transfusions, or surgery. Examples of second active agents are disclosed herein.

The solid forms of Compound 1 provided herein can also be combined or used in combination with other therapeutic agents useful in the treatment and/or prevention of MDS described herein.

In one embodiment, provided herein is a method of treating, preventing, and/or managing MDS, comprising administering to a patient a solid form of Compound 1 provided herein in combination with one or more second active agents, and optionally in combination with radiation therapy, blood transfusions, or surgery. Examples of second active agents are disclosed herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a patient with a disease or disorder. A first therapy (e.g., a prophylactic or therapeutic agent such as a compound provided herein, a compound provided herein, e.g., a solid form of Compound 1 can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

Administration of a solid form of Compound 1 provided herein and one or more second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the cancer being treated.

The route of administration of a solid form of Compound 1 is independent of the route of administration of a second therapy. In another embodiment, solid form of Compound 1 is administered intravenously. Thus, in accordance with these embodiments, a solid form of Compound 1 is administered intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, a solid form of Compound 1 and a second therapy are administered by the same mode of administration, orally or by IV. In another embodiment, a solid form of Compound 1 is administered by one mode of administration, e.g., by IV, whereas the second agent (an anticancer agent) is administered by another mode of administration, e.g., orally.

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated and/or managed, the severity and stage of disease, and the amount of the solid form of Compound 1 provided herein and any optional additional active agents concurrently administered to the patient.

One or more second active ingredients or agents can be used together with a solid form of Compound 1 in the methods and compositions provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies, particularly, therapeutic antibodies to cancer antigens. Typical large molecule active agents are biological molecules, such as naturally occurring or synthetic or recombinant proteins. Proteins that are particularly useful in the methods and compositions provided herein include proteins that stimulate the survival and/or proliferation of hematopoietic precursor cells and immunologically active poietic cells in vitro or in vivo. Other useful proteins stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

In certain embodiments, GM-CSF, G-CSF, SCF or EPO is administered subcutaneously during about five days in a four or six week cycle in an amount ranging from about 1 to about 750 mg/m$^2$/day, from about 25 to about 500 mg/m$^2$/day, from about 50 to about 250 mg/m$^2$/day, or from about 50 to about 200 mg/m$^2$/day. In certain embodiments, GM-CSF may be administered in an amount of from about 60 to about 500 mcg/m$^2$ intravenously over 2 hours or from about 5 to about 12 mcg/m$^2$/day subcutaneously. In certain embodiments, G-CSF may be administered subcutaneously in an amount of about 1 mcg/kg/day initially and can be adjusted depending on rise of total granulocyte counts. The maintenance dose of G-CSF may be administered in an amount of about 300 (in smaller patients) or 480 mcg subcutaneously. In certain embodiments, EPO may be administered subcutaneously in an amount of 10,000 Unit 3 times per week.

Particular proteins that can be used in the methods and compositions include, but are not limited to: filgrastim, which is sold in the United States under the trade name Neupogen® (Amgen, Thousand Oaks, Calif.); sargramostim, which is sold in the United States under the trade name Leukine® (Immunex, Seattle, Wash.); and recombinant EPO, which is sold in the United States under the trade name Epogen® (Amgen, Thousand Oaks, Calif.).

Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; the entireties of which are incorporated herein by reference.

Also provided for use in combination with a solid form of Compound 1 provided herein are native, naturally occurring, and recombinant proteins. Further encompassed are mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Antibodies that can be used in combination with a solid form of Compound 1 provided herein include monoclonal and polyclonal antibodies. Examples of antibodies include, but are not limited to, trastuzumab (Herceptin®), rituximab (Rituxan®), bevacizumab (Avastin™), pertuzumab (Omnitarg™), tositumomab (Bexxar®), edrecolomab (Panorex®), and G250. The solid forms of Compound 1 can also be combined with, or used in combination with, anti-TNF-α antibodies, and/or anti-EGFR antibodies, such as, for example, Erbitux® or panitumumab.

Large molecule active agents may be administered in the form of anti-cancer vaccines. For example, vaccines that secrete, or cause the secretion of, cytokines such as IL-2, G-CSF, and GM-CSF can be used in the methods and pharmaceutical compositions provided. See, e.g., Emens, L. A., et al., *Curr. Opinion Mol. Ther.* 3(1):77-84 (2001).

Second active agents that are small molecules can also be used to alleviate adverse effects associated with the administration of a solid form of Compound 1 provided herein. However, like some large molecules, many are believed to be capable of providing a synergistic effect when administered with (e.g., before, after or simultaneously) a solid form of Compound 1 provided herein. Examples of small molecule second active agents include, but are not limited to, anti-cancer agents, antibiotics, immunosuppressive agents, and steroids.

In certain embodiments, the second agent is an HSP inhibitor, a proteasome inhibitor, a FLT3 inhibitior or a TOR kinase inhibitor.

Examples of anti-cancer agents to be used within the methods or compositions described herein include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; clofarabine; crisnatol mesylate; cyclophosphamide; Ara-C; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; omacetaxine; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sorafenib; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs to be included within the methods or compositions include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; Ara-C ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevee); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurprin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

In certain embodiments, a solid form of Compound 1 is administered in combination with checkpoint inhibitors. In one embodiment, one checkpoint inhibitor is used in combination with a solid form of Compound 1 in connection with the methods provided herein. In another embodiment, two checkpoint inhibitors are used in combination with a solid form of Compound 1 in connection with the methods provided herein. In yet another embodiment, three or more checkpoint inhibitors are used in combination with a solid form of Compound 1 in connection with the methods provided herein.

As used herein, the term "immune checkpoint inhibitor" or "checkpoint inhibitor" refers to molecules that totally or partially reduce, inhibit, interfere with or modulate one or more checkpoint proteins. Without being limited by a particular theory, checkpoint proteins regulate T-cell activation or function. Numerous checkpoint proteins are known, such as CTLA-4 and its ligands CD80 and CD86; and PD-1 with its ligands PD-L1 and PD-L2 (Pardoll, Nature Reviews Cancer, 2012, 12, 252-264). These proteins appear responsible for co-stimulatory or inhibitory interactions of T-cell responses. Immune checkpoint proteins appear to regulate and maintain self-tolerance and the duration and amplitude of physiological immune responses. Immune checkpoint inhibitors include antibodies or are derived from antibodies.

In one embodiment, the checkpoint inhibitor is a CTLA-4 inhibitor. In one embodiment, the CTLA-4 inhibitor is an anti-CTLA-4 antibody. Examples of anti-CTLA-4 antibodies include, but are not limited to, those described in U.S.

Pat. Nos. 5,811,097; 5,811,097; 5,855,887; 6,051,227; 6,207,157; 6,682,736; 6,984,720; and 7,605,238, all of which are incorporated herein in their entireties. In one embodiment, the anti-CTLA-4 antibody is tremelimumab (also known as ticilimumab or CP-675,206). In another embodiment, the anti-CTLA-4 antibody is ipilimumab (also known as MDX-010 or MDX-101). Ipilimumab is a fully human monoclonal IgG antibody that binds to CTLA-4. Ipilimumab is marketed under the trade name Yervoy™.

In one embodiment, the checkpoint inhibitor is a PD-1/PD-L1 inhibitor. Examples of PD-1/PD-L1 inhibitors include, but are not limited to, those described in U.S. Pat. Nos. 7,488,802; 7,943,743; 8,008,449; 8,168,757; 8,217,149, and PCT Patent Application Publication Nos. WO2003042402, WO2008156712, WO2010089411, WO2010036959, WO2011066342, WO2011159877, WO2011082400, and WO2011161699, all of which are incorporated herein in their entireties.

In one embodiment, the checkpoint inhibitor is a PD-1 inhibitor. In one embodiment, the PD-1 inhibitor is an anti-PD-1 antibody. In one embodiment, the anti-PD-1 antibody is nivolumab (also known as ONO-4538, BMS-936558, or MDX1106) or pembrolizumab (also known as MK-3475, SCH 900475, or lambrolizumab). In one embodiment, the anti-PD-1 antibody is nivolumab. Nivolumab is a human IgG4 anti-PD-1 monoclonal antibody, and is marketed under the trade name Opdivo™. In another embodiment, the anti-PD-1 antibody is pembrolizumab. Pembrolizumab is a humanized monoclonal IgG4 antibody and is marketed under the trade name Keytruda™. In yet another embodiment, the anti-PD-1 antibody is CT-011, a humanized antibody. CT-011 administered alone has failed to show response in treating acute myeloid leukemia (AML) at relapse. In yet another embodiment, the anti-PD-1 antibody is AMP-224, a fusion protein.

In one embodiment, the checkpoint inhibitor is a PD-L1 inhibitor. In one embodiment, the PD-L1 inhibitor is an anti-PD-L1 antibody. In one embodiment, the anti-PD-L1 antibody is MEDI4736 (durvalumab). In another embodiment, the anti-PD-L1 antibody is BMS-936559 (also known as MDX-1105-01). In yet another embodiment, the PD-L1 inhibitor is atezolizumab (also known as MPDL3280A, and Tecentriq®).

In one embodiment, the checkpoint inhibitor is a PD-L2 inhibitor. In one embodiment, the PD-L2 inhibitor is an anti-PD-L2 antibody. In one embodiment, the anti-PD-L2 antibody is rHIgM12B7A.

In one embodiment, the checkpoint inhibitor is a lymphocyte activation gene-3 (LAG-3) inhibitor. In one embodiment, the LAG-3 inhibitor is IMP321, a soluble Ig fusion protein (Brignone et al., *J. Immunol.*, 2007, 179, 4202-4211). In another embodiment, the LAG-3 inhibitor is BMS-986016.

In one embodiment, the checkpoint inhibitors is a B7 inhibitor. In one embodiment, the B7 inhibitor is a B7-H3 inhibitor or a B7-H4 inhibitor. In one embodiment, the B7-H3 inhibitor is MGA271, an anti-B7-H3 antibody (Loo et al., *Clin. Cancer Res.*, 2012, 3834).

In one embodiment, the checkpoint inhibitors is a TIM3 (T-cell immunoglobulin domain and mucin domain 3) inhibitor (Fourcade et al., *J. Exp. Med.*, 2010, 207, 2175-86; Sakuishi et al., *J. Exp. Med.*, 2010, 207, 2187-94).

In one embodiment, the checkpoint inhibitor is an OX40 (CD134) agonist. In one embodiment, the checkpoint inhibitor is an anti-OX40 antibody. In one embodiment, the anti-OX40 antibody is anti-OX-40. In another embodiment, the anti-OX40 antibody is MEDI6469.

In one embodiment, the checkpoint inhibitor is a GITR agonist. In one embodiment, the checkpoint inhibitor is an anti-GITR antibody. In one embodiment, the anti-GITR antibody is TRX518.

In one embodiment, the checkpoint inhibitor is a CD137 agonist. In one embodiment, the checkpoint inhibitor is an anti-CD137 antibody. In one embodiment, the anti-CD137 antibody is urelumab. In another embodiment, the anti-CD137 antibody is PF-05082566.

In one embodiment, the checkpoint inhibitor is a CD40 agonist. In one embodiment, the checkpoint inhibitor is an anti-CD40 antibody. In one embodiment, the anti-CD40 antibody is CF-870,893.

In one embodiment, the checkpoint inhibitor is recombinant human interleukin-15 (rhIL-15).

In one embodiment, the checkpoint inhibitor is an IDO inhibitor. In one embodiment, the IDO inhibitor is INCB024360. In another embodiment, the IDO inhibitor is indoximod.

In certain embodiments, the combination therapies provided herein include two or more of the checkpoint inhibitors described herein (including checkpoint inhibitors of the same or different class). Moreover, the combination therapies described herein can be used in combination with second active agents as described herein where appropriate for treating diseases described herein and understood in the art.

In certain embodiments, Compound 1 can be used in combination with one or more immune cells expressing one or more chimeric antigen receptors (CARs) on their surface (e.g., a modified immune cell). Generally, CARs comprise an extracellular domain from a first protein e.g., an antigen-binding protein), a transmembrane domain, and an intracellular signaling domain. In certain embodiments, once the extracellular domain binds to a target protein such as a tumor-associated antigen (TAA) or tumor-specific antigen (TSA), a signal is generated via the intracellular signaling domain that activates the immune cell, e.g., to target and kill a cell expressing the target protein.

Extracellular domains: The extracellular domains of the CARs bind to an antigen of interest. In certain embodiments, the extracellular domain of the CAR comprises a receptor, or a portion of a receptor, that binds to said antigen. In certain embodiments, the extracellular domain comprises, or is, an antibody or an antigen-binding portion thereof. In specific embodiments, the extracellular domain comprises, or is, a single chain Fv (scFv) domain. The single-chain Fv domain can comprise, for example, a $V_L$ linked to $V_H$ by a flexible linker, wherein said $V_L$ and $V_H$ are from an antibody that binds said antigen.

In certain embodiments, the antigen recognized by the extracellular domain of a polypeptide described herein is a tumor-associated antigen (TAA) or a tumor-specific antigen (TSA). In various specific embodiments, the tumor-associated antigen or tumor-specific antigen is, without limitation, Her2, prostate stem cell antigen (PSCA), alpha-fetoprotein (AFP), carcinoembryonic antigen (CEA), cancer antigen-125 (CA-125), CA19-9, calretinin, MUC-1, B cell maturation antigen (BCMA), epithelial membrane protein (EMA), epithelial tumor antigen (ETA), tyrosinase, melanoma-24 associated antigen (MAGE), CD19, CD22, CD27, CD30, CD34, CD45, CD70, CD99, CD117, EGFRvIII (epidermal growth factor variant III), mesothelin, PAP (prostatic acid phosphatase), prostein, TARP (T cell receptor gamma alternate reading frame protein), Trp-p8, STEAPI (six-transmembrane epithelial antigen of the prostate 1), chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-I), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), an abnormal ras protein, or an abnormal p53 protein. In certain other embodiments, the TAA or TSA recognized by the extracellular domain of a CAR is integrin αvβ3 (CD61), galactin, or Ral-B.

In certain embodiments, the TAA or TSA recognized by the extracellular domain of a CAR is a cancer/testis (CT) antigen, e.g., BAGE, CAGE, CTAGE, FATE, GAGE, HCA661, HOM-TES-85, MAGEA, MAGEB, MAGEC, NA88, NY-ESO-1, NY-SAR-35, OY-TES-1, SPANXBI, SPA17, SSX, SYCPI, or TPTE.

In certain other embodiments, the TAA or TSA recognized by the extracellular domain of a CAR is a carbohydrate or ganglioside, e.g., fuc-GMI, GM2 (oncofetal antigen-immunogenic-1; OFA-I-1); GD2 (OFA-I-2), GM3, GD3, and the like.

In certain other embodiments, the TAA or TSA recognized by the extracellular domain of a CAR is alpha-actinin-4, Bage-1, BCR-ABL, Bcr-Abl fusion protein, beta-catenin, CA 125, CA 15-3 (CA 27.29\BCAA), CA 195, CA 242, CA-50, CAM43, Casp-8, cdc27, cdk4, cdkn2a, CEA, coa-1, dek-can fusion protein, EBNA, EF2, Epstein Barr virus antigens, ETV6-AML1 fusion protein, HLA-A2, HLA-All, hsp70-2, KIAA0205, Mart2, Mum-1, 2, and 3, neo-PAP, myosin class I, OS-9, pml-RARα fusion protein, PTPRK, K-ras, N-ras, triosephosphate isomerase, Gage 3,4,5,6,7, GnTV, Herv-K-mel, Lage-1, NA-88, NY-Eso-1/Lage-2, SP17, SSX-2, TRP2-Int2, gp100 (Pme117), tyrosinase, TRP-1, TRP-2, MAGE-1, MAGE-3, RAGE, GAGE-1, GAGE-2, p15(58), RAGE, SCP-1, Hom/Me1-40, PRAME, p53, HRas, HER-2/neu, E2A-PRL, H4-RET, IGH-IGK, MYL-RAR, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, 13-Catenin, Mum-1, p16, TAGE, PSMA, CT7, telomerase, 43-9F, 5T4, 791Tgp72, 13HCG, BCA225, BTAA, CD68\KP1, CO-029, FGF-5, G250, Ga733 (EpCAM), HTgp-175, M344, MA-50, MG7-Ag, MOV18, NB\70K, NY-C0-1, RCAS1, SDC-CAG16, TA-90, TAAL6, TAG72, TLP, or TPS.

In various specific embodiments, the tumor-associated antigen or tumor-specific antigen is an AML-related tumor antigens, as described in S. Anguille et al, *Leukemia* (2012), 26, 2186-2196.

Other tumor-associated and tumor-specific antigens are known to those in the art.

Receptors, antibodies, and scFvs that bind to TSAs and TAAs, useful in constructing chimeric antigen receptors, are known in the art, as are nucleotide sequences that encode them.

In certain specific embodiments, the antigen recognized by the extracellular domain of a chimeric antigen receptor is an antigen not generally considered to be a TSA or a TAA, but which is nevertheless associated with tumor cells, or damage caused by a tumor. In certain embodiments, for example, the antigen is, e.g., a growth factor, cytokine or interleukin, e.g., a growth factor, cytokine, or interleukin associated with angiogenesis or vasculogenesis. Such growth factors, cytokines, or interleukins can include, e.g., vascular endothelial growth factor (VEGF), basic fibroblast growth factor (bFGF), platelet-derived growth factor (PDGF), hepatocyte growth factor (HGF), insulin-like growth factor (IGF), or interleukin-8 (IL-8). Tumors can also create a hypoxic environment local to the tumor. As such, in other specific embodiments, the antigen is a hypoxia-associated factor, e.g., HIF-1α, HIF-2α, HIF-2β, HIF-3α, or HIF-3β. Tumors can also cause localized damage to normal tissue, causing the release of molecules known as damage associated molecular pattern molecules (DAMPs; also known as alarmins). In certain other specific embodiments, therefore, the antigen is a DAMP, e.g., a heat shock protein, chromatin-associated protein high mobility group box 1 (HMGB 1), S100A8 (MRP8, calgranulin A), S100A9 (MRP14, calgranulin B), serum amyloid A (SAA), or can be a deoxyribonucleic acid, adenosine triphosphate, uric acid, or heparin sulfate.

Transmembrane domain: In certain embodiments, the extracellular domain of the CAR is joined to the transmembrane domain of the polypeptide by a linker, spacer or hinge polypeptide sequence, e.g., a sequence from CD28 or a sequence from CTLA4. The transmembrane domain can be obtained or derived from the transmembrane domain of any transmembrane protein, and can include all or a portion of such transmembrane domain. In specific embodiments, the transmembrane domain can be obtained or derived from, e.g., CD8, CD16, a cytokine receptor, and interleukin receptor, or a growth factor receptor, or the like.

Intracellular signaling domains: In certain embodiments, the intracellular domain of a CAR is or comprises an intracellular domain or motif of a protein that is expressed on the surface of T cells and triggers activation and/or proliferation of said T cells. Such a domain or motif is able to transmit a primary antigen-binding signal that is necessary for the activation of a T lymphocyte in response to the antigen's binding to the CAR's extracellular portion. Typically, this domain or motif comprises, or is, an ITAM (immunoreceptor tyrosine-based activation motif). ITAM-containing polypeptides suitable for CARs include, for example, the zeta CD3 chain (CD3) or ITAM-containing portions thereof. In a specific embodiment, the intracellular domain is a CD3ζ intracellular signaling domain. In other specific embodiments, the intracellular domain is from a lymphocyte receptor chain, a TCR/CD3 complex protein, an Fe receptor subunit or an IL-2 receptor subunit. In certain embodiments, the CAR additionally comprises one or more co-stimulatory domains or motifs, e.g., as part of the intracellular domain of the polypeptide. The one or more co-stimulatory domains or motifs can be, or can comprise comprise, one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or a co-stimulatory inducible T-cell costimulatory (ICOS) polypeptide sequence, or other costimulatory domain or motif, or any combination thereof.

The CAR may also comprise a T cell survival motif. The T cell survival motif can be any polypeptide sequence or motif that facilitates the survival of the T lymphocyte after stimulation by an antigen. In certain embodiments, the T cell survival motif is, or is derived from, CD3, CD28, an intracellular signaling domain of IL-7 receptor (IL-7R), an intracellular signaling domain of IL-12 receptor, an intracellular signaling domain of IL-15 receptor, an intracellular signaling domain of IL-21 receptor, or an intracellular signaling domain of transforming growth factor 0 (TGFβ) receptor.

The modified immune cells expressing the CARs can be, e.g., T lymphocytes (T cells, e.g., CD4+ T cells or CD8+ T cells), cytotoxic lymphocytes (CTLs) or natural killer (NK) cells. T lymphocytes used in the compositions and methods provided herein may be naive T lymphocytes or MHC-restricted T lymphocytes. In certain embodiments, the T lymphocytes are tumor infiltrating lymphocytes (TILs). In certain embodiments, the T lymphocytes have been isolated from a tumor biopsy, or have been expanded from T lymphocytes isolated from a tumor biopsy. In certain other embodiments, the T cells have been isolated from, or are expanded from T lymphocytes isolated from, peripheral blood, cord blood, or lymph. Immune cells to be used to generate modified immune cells expressing a CAR can be isolated using art-accepted, routine methods, e.g., blood collection followed by apheresis and optionally antibody-mediated cell isolation or sorting.

The modified immune cells are preferably autologous to an individual to whom the modified immune cells are to be administered. In certain other embodiments, the modified immune cells are allogeneic to an individual to whom the modified immune cells are to be administered. Where allogeneic T lymphocytes or NK cells are used to prepare modified T lymphocytes, it is preferable to select T lymphocytes or NK cells that will reduce the possibility of graft-versus-host disease (GVHD) in the individual. For example, in certain embodiments, virus-specific T lymphocytes are selected for preparation of modified T lymphocytes; such lymphocytes will be expected to have a greatly reduced native capacity to bind to, and thus become activated by, any recipient antigens. In certain embodiments, recipient-mediated rejection of allogeneic T lymphocytes can be reduced by co-administration to the host of one or more immunosuppressive agents, e.g., cyclosporine, tacrolimus, sirolimus, cyclophosphamide, or the like.

T lymphocytes, e.g., unmodified T lymphocytes, or T lymphocytes expressing CD3 and CD28, or comprising a polypeptide comprising a CD3t signaling domain and a CD28 co-stimulatory domain, can be expanded using antibodies to CD3 and CD28, e.g., antibodies attached to beads; see, e.g., U.S. Pat. Nos. 5,948,893; 6,534,055; 6,352,694; 6,692,964; 6,887,466; and 6,905,681.

The modified immune cells, e.g., modified T lymphocytes, can optionally comprise a "suicide gene" or "safety switch" that enables killing of substantially all of the modified immune cells when desired. For example, the modified T lymphocytes, in certain embodiments, can comprise an HSV thymidine kinase gene (HSV-TK), which causes death of the modified T lymphocytes upon contact with gancyclovir. In another embodiment, the modified T lymphocytes comprise an inducible caspase, e.g., an inducible caspase 9 (icaspase9), e.g., a fusion protein between caspase 9 and human FK506 binding protein allowing for dimerization using a specific small molecule pharmaceutical. See Straathof et al., Blood 1 05(11):4247-4254 (2005).

Specific second active agents particularly useful in the methods or compositions include, but are not limited to, rituximab, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, interferon alpha, pegylated interferon alpha (e.g., PEG INTRON-A), capecitabine, cisplatin, thiotepa, fludarabine, carboplatin, liposomal daunorubicin, Ara-C, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

In certain embodiments of the methods provided herein, use of a second active agent in combination with a solid form of Compound 1 provided herein may be modified or delayed during or shortly following administration of a solid form of Compound 1 provided herein as deemed appropriate by the practitioner of skill in the art. In certain embodiments, subjects being administered a solid form of Compound 1 provided herein alone or in combination with other therapies may receive supportive care including antiemetics, myeloid growth factors, and transfusions of platelets, when appropriate. In some embodiments, subjects being administered a solid form of Compound 1 provided herein may be administered a growth factor as a second active agent according to the judgment of the practitioner of skill in the art. In some embodiments, provided is administration of a solid form of Compound 1 provided herein in combination with erythropoietin or darbepoetin (Aranesp).

In certain embodiments, a solid form of Compound 1 provided herein is administered with gemcitabine, cisplatinum, 5-fluorouracil, mitomycin, methotrexate, vinblastine, doxorubicin, carboplatin, thiotepa, paclitaxel or docetaxel to patients with locally advanced or metastatic transitional cell bladder cancer.

In certain embodiments, a solid form of Compound 1 provided herein is administered in combination with a second active ingredient as follows: temozolomide to pediatric patients with relapsed or progressive brain tumors or recurrent neuroblastoma; celecoxib, etoposide and cyclophosphamide for relapsed or progressive CNS cancer; temodar to patients with recurrent or progressive meningioma, malignant meningioma, hemangiopericytoma, multiple brain metastases, relapased brain tumors, or newly diagnosed glioblastoma multiforms; irinotecan to patients with recurrent glioblastoma; carboplatin to pediatric patients with brain stem glioma; procarbazine to pediatric patients with progressive malignant gliomas; cyclophosphamide to patients with poor prognosis malignant brain tumors, newly diagnosed or recurrent glioblastoma multiforms; Gliadel® for high grade recurrent malignant gliomas; temozolomide and tamoxifen for anaplastic astrocytoma; or topotecan for gliomas, glioblastoma, anaplastic astrocytoma or anaplastic oligodendroglioma.

In certain embodiments, a solid form of Compound 1 provided herein is administered with methotrexate, cyclophosphamide, 5-fluorouracil, taxane, everolimus, abraxane, lapatinib, herceptin, pamidronate disodium, eribulin mesylate, everolimus, gemcitabine, palbociclib, ixabepilone, kadcyla, pertuzumab, theotepa, aromatase inhibitors, exemestane, selective estrogen modulators, estrogen receptor antagonists, anthracyclines, emtansine, and/or pexidartinib to patients with metastatic breast cancer.

In certain embodiments, a solid form of Compound 1 provided herein is administered with temozolomide, doxorubicin (Adriamycin), fluorouracil (Adrucil, 5-fluorouracil), or streptozocin (Zanosar) to patients with neuroendocrine tumors.

In certain embodiments, a solid form of Compound 1 provided herein is administered with methotrexate, gemcitabine, cisplatin, cetuximab, 5-fluorouracil, bleomycin, docetaxel or carboplatin to patients with recurrent or metastatic head or neck cancer.

In certain embodiments, a solid form of Compound 1 provided herein is administered with gemcitabine, abraxane, 5-fluorouracil, afinitor, irinotecan, mitomycin C, sunitinib or tarceva to patients with pancreatic cancer.

In certain embodiments, a solid form of Compound 1 provided herein is administered to patients with colon cancer in combination with ARISA®, avastatin, oxaliplatin, 5-fluorouracil, irinotecan, capecitabine, cetuximab, ramucirumab, panitumumab, bevacizumab, leucovorin calcium, lonsurf, regorafenib, ziv-aflibercept, taxol, and/or taxotere.

In certain embodiments, a solid form of Compound 1 provided herein is administered with capecitabine and/or vemurafenib to patients with refractory colorectal cancer or patients who fail first line therapy or have poor performance in colon or rectal adenocarcinoma.

In certain embodiments, a solid form of Compound 1 provided herein is administered in combination with fluorouracil, leucovorin, and irinotecan to patients with Dukes C & D colorectal cancer or to patients who have been previously treated for metastatic colorectal cancer.

In certain embodiments, a solid form of Compound 1 provided herein is administered to patients with refractory colorectal cancer in combination with capecitabine, xeloda, and/or irinotecan.

In certain embodiments, a solid form of Compound 1 provided herein is administered with capecitabine and irinotecan to patients with refractory colorectal cancer or to patients with unresectable or metastatic colorectal carcinoma.

In certain embodiments, a solid form of Compound 1 provided herein is administered alone or in combination with interferon alpha or capecitabine to patients with unresectable or metastatic hepatocellular carcinoma; or with cisplatin and thiotepa, or with sorafenib tosylate to patients with primary or metastatic liver cancer.

In certain embodiments, a solid form of Compound 1 provided herein is administered in combination with doxorubicin, paclitaxel, vinblastine or pegylated interferon alpha to patients with Kaposi's sarcoma.

In certain embodiments, a solid form of Compound 1 provided herein is administered in combination with arsenic trioxide, fludarabine, carboplatin, daunorubicin, cyclophosphamide, cytarabine, doxorubicin, idarubicin, mitoxantrone hydrochloride, thioguanine, vincritine, and/or topotecan to patients with refractory or relapsed or high-risk acute myeloid leukemia.

In certain embodiments, a solid form of Compound 1 provided herein is administered in combination with liposomal daunorubicin, topotecan and/or cytarabine to patients with unfavorable karotype acute myeloblastic leukemia.

In certain embodiments, a solid form of Compound 1 provided herein is administered in combination with methotrexate, mechlorethamine hydrochloride, afatinib dimaleate, pemetrexed, bevacizumab, carboplatin, cisplatin, ceritinib, crizotinib, ramucirumab, pembrolizumab, docetaxel, vinorelbine tartrate, gemcitabine, abraxane, erlotinib, geftinib, and/or irinotecan to patients with non-small cell lung cancer.

In certain embodiments, a solid form of Compound 1 provided herein is administered in combination with carboplatin and irinotecan to patients with non-small cell lung cancer.

In certain embodiments, a solid form of Compound 1 provided herein is administered with doxetaxol to patients with non-small cell lung cancer who have been previously treated with carbo/etoposide and radiotherapy.

In certain embodiments, a solid form of Compound 1 provided herein is administered in combination with carboplatin and/or taxotere, or in combination with carboplatin, pacilitaxel and/or thoracic radiotherapy to patients with non-small cell lung cancer.

In certain embodiments, a solid form of Compound 1 provided herein is administered in combination with taxotere to patients with stage IIIB or IV non-small cell lung cancer.

In certain embodiments, a solid form of Compound 1 provided herein is administered in combination with oblimersen (Genasense®), methotrexate, mechlorethamine hydrochloride, etoposide, topotecan or doxorubicin to patients with small cell lung cancer.

In certain embodiments, a solid form of Compound 1 provided herein is administered in combination with ABT-737 (Abbott Laboratories) and/or obatoclax (GX15-070) to patients with lymphoma and other blood cancers.

In certain embodiments, a solid form of Compound 1 provided herein is administered alone or in combination with a second active ingredient such as vinblastine or fludarabine adcetris, ambochlorin, becenum, bleomycin, brentuximab vedotin, carmustinem chlorambucil, cyclophosphamide, dacarbazine, doxorubicin, lomustine, matulane, mechlorethamine hydrochloride, prednisone, procarbazine hydrochloride or vincristine to patients with various types of lymphoma, including, but not limited to, Hodgkin's lymphoma, non-Hodgkin's lymphoma, cutaneous T-Cell lymphoma, cutaneous B-Cell lymphoma, diffuse large B-Cell lymphoma or relapsed or refractory low grade follicular lymphoma.

In certain embodiments, a solid form of Compound 1 provided herein is administered in combination with taxotere, dabrafenib, imlygic, ipilimumab, pembrolizumab, nivolumab, trametinib, vemurafenib, talimogene laherparepvec, IL-2, IFN, GM-CSF, and/or dacarbazine to patients with various types or stages of melanoma.

In certain embodiments, a solid form of Compound 1 provided herein is administered alone or in combination with vinorelbine to patients with malignant mesothelioma, or stage IIIB non-small cell lung cancer with pleural implants or malignant pleural effusion mesothelioma syndrome.

In certain embodiments, a solid form of Compound 1 provided herein is administered to patients with various types or stages of multiple myeloma in combination with dexamethasone, zoledronic acid, palmitronate, GM-CSF, biaxin, vinblastine, melphalan, busulphan, cyclophosphamide, IFN, prednisone, bisphosphonate, celecoxib, arsenic trioxide, PEG INTRON-A, vincristine, becenum, bortezomib, carfilzomib, doxorubicin, panobinostat, lenalidomide, pomalidomide, thalidomide, mozobil or a combination thereof.

In certain embodiments, a solid form of Compound 1 provided herein is administered to patients with various types or stages of multiple myeloma in combination with chimeric antigen receptor (CAR) T-cells.

In certain embodiments, a solid form of Compound 1 provided herein is administered to patients with relapsed or refractory multiple myeloma in combination with doxorubicin (Doxir®), vincristine and/or dexamethasone (Decadron®).

In certain embodiments, a solid form of Compound 1 provided herein is administered to patients with various types or stages of ovarian cancer such as peritoneal carcinoma, papillary serous carcinoma, refractory ovarian cancer or recurrent ovarian cancer, in combination with taxol, carboplatin, doxorubicin, gemcitabine, cisplatin, xeloda, paclitaxel, dexamethasone, avastin, cyclophosphamide, topotecan, olaparib, thiotepa, or a combination thereof.

In certain embodiments, a solid form of Compound 1 provided herein is administered to patients with various types or stages of prostate cancer, in combination with xeloda, 5 FU/LV, gemcitabine, irinotecan plus gemcitabine, cyclophosphamide, vincristine, dexamethasone, GM-CSF, celecoxib, taxotere, ganciclovir, paclitaxel, adriamycin, docetaxel, estramustine, Emcyt, denderon, zytiga, bicalutamide, cabazitaxel, degarelix, enzalutamide, zoladex, leuprolide acetate, mitoxantrone hydrochloride, prednisone, sipuleucel-T, radium 223 dichloride, or a combination thereof.

In certain embodiments, a solid form of Compound 1 provided herein is administered to patients with various types or stages of renal cell cancer, in combination with capecitabine, IFN, tamoxifen, IL-2, GM-CSF, Celebrex®, or a combination thereof.

In certain embodiments, a solid form of Compound 1 provided herein is administered to patients with various types or stages of gynecologic, uterus or soft tissue sarcoma cancer in combination with IFN, dactinomycin, doxorubicin, imatinib mesylate, pazopanib, hydrochloride, trabectedin, a COX-2 inhibitor such as Celebrex®, and/or sulindac.

In certain embodiments, a solid form of Compound 1 provided herein is administered to patients with various types or stages of solid tumors in combination with celebrex, etoposide, cyclophosphamide, docetaxel, apecitabine, IFN, tamoxifen, IL-2, GM-CSF, or a combination thereof.

In certain embodiments, a solid form of Compound 1 provided herein is administered to patients with scleroderma or cutaneous vasculitis in combination with celebrex, etoposide, cyclophosphamide, docetaxel, apecitabine, IFN, tamoxifen, IL-2, GM-CSF, or a combination thereof.

In certain embodiments, a solid form of Compound 1 provided herein is administered to patients with MDS in combination with azacitidine, cytarabine, daunorubicin, decitabine, idarubicin, lenalidomide or a combination thereof.

Also encompassed herein is a method of increasing the dosage of an anti-cancer drug or agent that can be safely and effectively administered to a patient, which comprises administering to the patient (e.g., a human) a solid form of Compound 1 provided herein. Patients that can benefit by this method are those likely to suffer from an adverse effect associated with anti-cancer drugs for treating a specific cancer of the skin, subcutaneous tissue, lymph nodes, brain, lung, liver, bone, intestine, colon, heart, pancreas, adrenal, kidney, prostate, breast, colorectal, or combinations thereof. The administration of a solid form of Compound 1 provided herein alleviates or reduces adverse effects which are of such severity that it would otherwise limit the amount of anti-cancer drug.

In one embodiment, a solid form of Compound 1 provided herein is administered daily in an amount ranging from about 0.1 to about 150 mg, from about 1 to about 50 mg, or from about 2 to about 25 mg, or from about 1 to about 10 mg, prior to, during, or after the occurrence of the adverse effect associated with the administration of an anti-cancer drug to a patient. In certain embodiments, a solid form of Compound 1 provided herein is administered in combination with specific agents such as heparin, aspirin, coumadin, or G-CSF to avoid adverse effects that are associated with anti-cancer drugs such as but not limited to neutropenia or thrombocytopenia.

In one embodiment, a solid form of Compound 1 provided herein is administered to patients with diseases and disorders associated with or characterized by, undesired angiogenesis in combination with additional active ingredients, including, but not limited to, anti-cancer drugs, anti-inflammatories, antihistamines, antibiotics, and steroids.

In another embodiment, encompassed herein is a method of treating, preventing and/or managing cancer, which comprises administering a solid form of Compound 1 provided herein in conjunction with (e.g. before, during, or after) conventional therapy including, but not limited to, surgery, immunotherapy, biological therapy, radiation therapy, or other non-drug based therapy presently used to treat, prevent and/or manage cancer. The combined use of the compound provided herein and conventional therapy may provide a unique treatment regimen that is unexpectedly effective in certain patients. Without being limited by theory, it is believed that a solid form of Compound 1 provided herein may provide additive or synergistic effects when given concurrently with conventional therapy.

As discussed elsewhere herein, encompassed herein is a method of reducing, treating and/or preventing adverse or undesired effects associated with conventional therapy including, but not limited to, surgery, chemotherapy, radiation therapy, hormonal therapy, biological therapy and immunotherapy. A solid form of Compound 1 provided herein and other active ingredient can be administered to a patient prior to, during, or after the occurrence of the adverse effect associated with conventional therapy.

In certain embodiments, the methods provided herein comprise administration of calcium, calcitriol, and vitamin D supplementation with a solid form of Compound 1. In certain embodiments, the methods provided herein comprise administration of calcium, calcitriol, and vitamin D supplementation prior to the treatment with a solid form of Compound 1.

In certain embodiments, calcium supplementation is administered to deliver at least 1200 mg of elemental calcium per day given in divided doses. In certain embodiments, calcium supplementation is administered as calcium carbonate in a dose of 500 mg administered three times a day per orally (PO).

In certain embodiments, calcitriol supplementation is administered to deliver 0.25 µg calcitriol (PO) once daily.

In certain embodiments, vitamin D supplementation is administered to deliver about 500 IU to about 5000 IU vitamin D once daily. In certain embodiments, vitamin D supplementation is administered to deliver about 1000 IU vitamin D once daily. In certain embodiments, vitamin D supplementation is administered to deliver about 50,000 IU vitamin D weekly. In certain embodiments, vitamin D supplementation is administered to deliver about 1000 IU vitamin D2 or D3 once daily. In certain embodiments, vitamin D supplementation is administered to deliver about 50,000 IU vitamin D2 or D3 weekly.

In one embodiment, the solid form of Compound 1 can be administered in an amount ranging from about 0.1 to about 150 mg, from about 1 to about 25 mg, or from about 2 to about 10 mg daily alone, or in combination with a second active agent disclosed herein, prior to, during, or after the use of conventional therapy.

In certain embodiments, a solid form of Compound 1 provided herein and doxetaxol are administered to patients with non-small cell lung cancer who were previously treated with carbo/VP 16 and radiotherapy.

6.3.2. Use With Transplantation Therapy

The solid forms of Compound 1 provided herein provided herein can be used to reduce the risk of Graft Versus Host Disease (GVHD). Therefore, encompassed herein is a method of treating, preventing and/or managing cancer, which comprises administering a solid form of Compound 1 provided herein in conjunction with transplantation therapy.

As those of ordinary skill in the art are aware, the treatment of cancer is often based on the stages and mechanism of the disease. For example, as inevitable leukemic transformation develops in certain stages of cancer, transplantation of peripheral blood stem cells, hematopoietic stem cell preparation or bone marrow may be necessary. The combined use of a solid form of Compound 1 provided herein provided herein and transplantation therapy provides a unique and unexpected synergism. In particular, a solid form of Compound 1 provided herein exhibits immunomodulatory activity that may provide additive or synergistic effects when given concurrently with transplantation therapy in patients with cancer.

The solid forms of Compound 1 provided herein can work in combination with transplantation therapy reducing complications associated with the invasive procedure of transplantation and risk of GVHD. Encompassed herein is a method of treating, preventing and/or managing cancer which comprises administering to a patient (e.g., a human) solid form of Compound 1 provided herein before, during, or after the transplantation of umbilical cord blood, placental blood, peripheral blood stem cell, hematopoietic stem cell preparation, or bone marrow. Some examples of stem cells suitable for use in the methods provided herein are disclosed in U.S. Pat. No. 7,498,171, the disclosure of which is incorporated herein by reference in its entirety.

In one embodiment, a solid form of Compound 1 provided herein is administered to patients with acute myeloid leukemia before, during, or after transplantation.

In one embodiment, a solid form of Compound 1 provided herein is administered to patients with multiple myeloma before, during, or after the transplantation of autologous peripheral blood progenitor cell.

In one embodiment, a solid form of Compound 1 provided herein is administered to patients with NHL (e.g., DLBCL) before, during, or after the transplantation of autologous peripheral blood progenitor cell.

6.3.3. Cycling Therapy

In certain embodiments, the prophylactic or therapeutic agents provided herein are cyclically administered to a patient. Cycling therapy involves the administration of an active agent for a period of time, followed by a rest for a period of time, and repeating this sequential administration. Cycling therapy can reduce the development of resistance to one or more of the therapies, avoid, or reduce the side effects of one of the therapies, and/or improves the efficacy of the treatment.

Consequently, in certain embodiments, a solid form of Compound 1 provided herein provided herein is administered daily in a single or divided doses in a four to six week cycle with a rest period of about a week or two weeks. The cycling method further allows the frequency, number, and length of dosing cycles to be increased. Thus, encompassed herein in certain embodiments is the administration of a solid form of Compound 1 provided herein for more cycles than are typical when it is administered alone. In certain embodiments, a solid form of Compound 1 provided herein is administered for a greater number of cycles that would typically cause dose-limiting toxicity in a patient to whom a second active ingredient is not also being administered.

In one embodiment, a solid form of Compound 1 provided herein is administered daily and continuously for three or four weeks at a dose of from about 0.1 to about 150 mg/d followed by a break of one or two weeks. In another embodiment, a solid form of Compound 1 provided herein is administered once a day for the first two to five or ten days of a 28 day cycle, followed by a rest period with no administration for the rest of the 28 day cycle in a dose from about 1 to about 10 mg.

In another embodiment, a solid form of Compound 1 provided herein and a second active ingredient are administered orally, with administration of the solid form of Compound 1 occurring 30 to 60 minutes prior to a second active ingredient, during a cycle of four to six weeks. In certain embodiments, the combination of a solid form of Compound 1 provided herein and a second active ingredient is administered by intravenous infusion over about 90 minutes every cycle. In certain embodiments, one cycle comprises the administration from about 0.1 to about 150 mg/day of a solid form of Compound 1 provided herein and from about 50 to about 200 mg/m$^2$/day of a second active ingredient daily for three to four weeks and then one or two weeks of rest. In certain embodiments, the number of cycles during which the combinatorial treatment is administered to a patient is ranging from about one to about 24 cycles, from about two to about 16 cycles, or from about four to about three cycles.

6.4. Patient Population

In certain embodiments of the methods provided herein, the subject is an animal, preferably a mammal, more preferably a non-human primate. In particular embodiments, the subject is a human. The subject can be a male or female subject.

Particularly useful subjects for the methods provided herein include human cancer patients, for example, those who have been diagnosed with leukemia, including acute myeloid leukemia, acute lymphocytic leukemia, chronic myelogenous leukemia, and chronic myelogenous leukemia. In certain embodiments, the subject has not been diagnosed with acute promyelocytic leukemia.

In some embodiments, the subject has a higher than normal blast population. In some embodiments, the subject has a blast population of at least 10%. In some embodiments, the subject has a blast population of between 10 and 15%. In some embodiments, the subject has a blast population of at least 15%. In some embodiments, the subject has a blast population of between 15 and 20%. In some embodiments, the subject has a blast population of at least 20%. In some embodiments, the subject has a blast population of about 10-15%, about 15-20%, or about 20-25%. In other embodiments, the subject has a blast population of less than 10%. In the context of the methods described herein, useful subjects having a blast population of less than 10% includes those subjects that, for any reason according to the judgment of the skilled practitioner in the art, are in need of treatment with a compound provided herein, alone or in combination with a second active agent.

In some embodiments, the subject is treated based on the Eastern Cooperative Oncology Group (ECOG) performance status score of the subject for leukemia. ECOG performance status can be scored on a scale of 0 to 5, with 0 denoting asymptomatic; 1 denoting symptomatic but completely ambulant; 2 denoting symptomatic and <50% in bed during the day; 3 denoting symptomatic and >50% in bed, but not bed bound; 4 denoting bed bound; and 5 denoting death. In some embodiments, the subject has an ECOG performance status score of 0 or 1. In some embodiments, the subject has an ECOG performance status score of 0. In some embodiments, the subject has an ECOG performance status score of 1. In other embodiments, the subject has an ECOG performance status score of 2.

In certain embodiments, the methods provided herein encompass the treatment of subjects who have not been previously treated for leukemia. In some embodiments, the subject has not undergone allogeneic bone marrow transplantation. In some embodiments, the subject has not undergone a stem cell transplantation. In some embodiments, the subject has not received hydroxyurea treatment. In some embodiments, the subject has not been treated with any investigational products for leukemia. In some embodiments, the subject has not been treated with systemic glucocorticoids.

In other embodiments, the methods encompass treating subjects who have been previously treated or are currently being treated for leukemia. For example, the subject may have been previously treated or are currently being treated with a standard treatment regimen for leukemia. The subject may have been treated with any standard leukemia treatment regimen known to the practitioner of skill in the art. In certain embodiments, the subject has been previously treated with at least one induction/reinduction or consolidation AML regimen. In some embodiments, the subject has undergone autologous bone marrow transplantation or stem cell transplantation as part of a consolidation regimen. In some embodiments, the bone marrow or stem cell transplantation occurred at least 3 months prior to treatment according to the methods provided herein. In some embodiments, the subject has undergone hydroxyurea treatment. In some embodiments, the hydroxyurea treatment occurred no later than 24 hours prior to treatment according to the methods provided herein. In some embodiments, the subject has undergone prior induction or consolidation therapy with cytarabine (Ara-C). In some embodiments, the subject has undergone treatment with systemic glucocorticosteroids. In some embodiments, the glucocorticosteroid treatment occurred no later 24 hours prior to treatment according to the methods described herein. In other embodiments, the methods encompass treating subjects who have been previously treated for cancer, but are non-responsive to standard therapies.

Also encompassed are methods of treating subjects having relapsed or refractory leukemia. In some embodiments, the subject has been diagnosed with a relapsed or refractory AML subtype, as defined by the World Health Organization (WHO). Relapsed or refractory disease may be de novo AML or secondary AML, e.g., therapy-related AML (t-AML).

In some embodiments, the methods provided herein are used to treat drug resistant leukemias, such as chronic myelogenous leukemia (CML). Thus, treatment with a compound provided herein could provide an alternative for patients who do not respond to other methods of treatment. In some embodiments, such other methods of treatment encompass treatment with Gleevec® (imatinib mesylate). In some embodiments, provided herein are methods of treatment of Philadelphia chromosome positive chronic myelogenous leukemia (Ph+CML). In some embodiments, provided herein are methods of treatment of Gleevec® (imatinib mesylate) resistant Philadelphia chromosome positive chronic myelogenous leukemia (Ph+CML).

Also encompassed are methods of treating a subject regardless of the subject's age, although some diseases or disorders are more common in certain age groups. In some embodiments, the subject is at least 18 years old. In some embodiments, the subject is more than 18, 25, 35, 40, 45, 50, 55, 60, 65, or 70 years old. In other embodiments, the subject is less than 65 years old. In some embodiments, the subject is less than 18 years old. In some embodiments, the subject is less than 18, 15, 12, 10, 9, 8 or 7 years old.

In some embodiments, the methods may find use in subjects at least 50 years of age, although younger subjects could benefit from the method as well. In other embodiments, the subjects are at least 55, at least 60, at least 65, and at least 70 years of age. In another embodiment, the subjects have adverse cytogenetics. "Adverse cytogenetics" is defined as any nondiploid karyotype, or greater than or equal to 3 chromosomal abnormalities. In another embodiment, the subjects are at least 60 years of age and have adverse cytogenetics. In another embodiment, the subjects are 60-65 years of age and have adverse cytogenetics. In another embodiment, the subjects are 65-70 years of age and have adverse cytogenetics.

In certain embodiments, the subject treated has no history of myocardial infarction within three months of treatment according to the methods provided herein. In some embodiments, the subject has no history of cerebrovascular accident or transient ischemic attack within three months of treatment according to the methods provided herein. In some embodiments, the subject has no suffered no thromboembelic event, including deep vein thrombosis or pulmonary embolus, within 28 days of treatment according to the methods provided herein. In other embodiments, the subject has not experienced or is not experiencing uncontrolled disseminated intravascular coagulation.

Because subjects with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual subject with cancer.

It will be appreciated that every suitable combination of the compounds provided herein with one or more of the aforementioned compounds and optionally one or more further pharmacologically active substances is contemplated herein.

6.5. Formulation of Pharmaceutical Compositions

The pharmaceutical compositions provided herein contain therapeutically effective amounts of one or more solid forms of Compound 1 provided herein and a pharmaceutically acceptable carrier, diluent or excipient.

In one embodiment, the pharmaceutical compositions provided herein comprise Form A of Compound 1 and one or more pharmaceutically acceptable excipients or carriers. In one embodiment, the pharmaceutical compositions provided herein comprise Form B of Compound 1 and one or more pharmaceutically acceptable excipients or carriers. In one embodiment, the pharmaceutical compositions provided herein comprise Form C of Compound 1 and one or more pharmaceutically acceptable excipients or carriers. In one embodiment, the pharmaceutical compositions provided herein comprise Form D of Compound 1 and one or more pharmaceutically acceptable excipients or carriers. In one embodiment, the pharmaceutical compositions provided herein comprise Form E of Compound 1 and one or more pharmaceutically acceptable excipients or carriers. In one embodiment, the pharmaceutical compositions provided herein comprise amorphous Compound 1 and one or more pharmaceutically acceptable excipients or carriers.

The compounds can be formulated into suitable pharmaceutical preparations such as in sterile solutions or suspensions for ophthalmic or parenteral administration, as well as transdermal patch preparation and dry powder inhalers. Typically the solid forms of Compound 1 described above are formulated into pharmaceutical compositions using techniques and procedures well known in the art (see, e.g., Ansel Introduction to Pharmaceutical Dosage Forms, Seventh Edition 1999).

In the compositions, effective concentrations of one or more solid forms of Compound 1 is mixed with a suitable pharmaceutical carrier or vehicle. In certain embodiments, the concentrations of the solid forms of Compound 1 in the compositions are effective for delivery of an amount, upon administration, that treats, prevents, or ameliorates one or more of the symptoms and/or progression of cancer, including solid tumors and blood borne tumors.

Typically, the compositions are formulated for single dosage administration. To formulate a composition, the weight fraction of a solid form of Compound 1 is dissolved, suspended, dispersed or otherwise mixed in a selected vehicle at an effective concentration such that the treated condition is relieved or ameliorated. Pharmaceutical carriers or vehicles suitable for administration of the solid forms of Compound 1 provided herein include any such carriers known to those skilled in the art to be suitable for the particular mode of administration.

In addition, the solid forms of Compound 1 may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

A solid form of Compound 1 is included in the pharmaceutically acceptable carrier in an amount sufficient to exert a therapeutically useful effect in the absence of undesirable side effects on the patient treated. The therapeutically effective concentration may be determined empirically by testing the solid forms of Compound 1 in in vitro and in vivo systems described herein and then extrapolated therefrom for dosages for humans.

The concentration of a solid form of Compound 1 in the pharmaceutical composition will depend on absorption, tissue distribution, inactivation and excretion rates of the solid form of Compound 1, the physicochemical characteristics of the solid form of Compound 1, the dosage schedule, and amount administered as well as other factors known to those of skill in the art. For example, the amount that is delivered is sufficient to ameliorate one or more of the symptoms of cancer, including solid tumors and blood borne tumors.

In certain embodiments, a therapeutically effective dosage should produce a serum concentration of active ingredient of from about 0.1 ng/mL to about 50-100 µg/mL. In one embodiment, the pharmaceutical compositions provide a dosage of from about 0.001 mg to about 2000 mg of compound per kilogram of body weight per day. Pharmaceutical dosage unit forms are prepared to provide from about 1 mg to about 1000 mg and in certain embodiments, from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Thus, effective concentrations or amounts of one or more of the solid forms of Compound 1 described herein are mixed with a suitable pharmaceutical carrier or vehicle for systemic, topical or local administration to form pharmaceutical compositions. The solid forms of Compound 1 are included in an amount effective for ameliorating one or more symptoms of, or for treating, retarding progression, or preventing. The concentration of a solid form of Compound 1 in the composition will depend on absorption, tissue distribution, inactivation, excretion rates of the solid form of Compound 1, the dosage schedule, amount administered, particular formulation as well as other factors known to those of skill in the art.

The compositions are intended to be administered by a suitable route, including but not limited to parenterally, rectally, topically and locally. The compositions are in liquid, semi-liquid or solid form and are formulated in a manner suitable for each route of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, pens, disposable syringes or single or multiple dose vials made of glass, plastic or other suitable material.

In instances in which the solid forms of Compound 1 exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the solid form of Compound 1 in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as powders, sterile parenteral solutions or suspensions, and oil water emulsions containing suitable quantities of the solid forms of Compound 1. The solid forms of Compound 1 are formulated and administered in unit dosage forms or multiple dosage forms. Unit dose forms as used herein refer to physically discrete units suitable for human and animal subjects and packaged individually as is known in the art. Each unit dose contains a predetermined quantity of the solid form of Compound 1 sufficient to produce the desired therapeutic effect, in association with the required pharmaceutical carrier, vehicle or diluent. Examples of unit dose forms include ampules and syringes. Unit dose forms may be administered in fractions or multiples thereof. A multiple dose form is a plurality of identical unit dosage forms packaged in a single container to be administered in segregated unit dose form. Examples of multiple dose forms include vials, or bottles of pints or gallons. Hence, multiple dose form is a multiple of unit doses which are not segregated in packaging.

Sustained-release preparations can also be prepared. Suitable examples of sustained-release preparations include semipermeable matrices of solid hydrophobic polymers containing a solid form of Compound 1 provided herein, which matrices are in the form of shaped articles, e.g., films, or microcapsule. Examples of sustained-release matrices include iontophoresis patches, polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Dosage forms or compositions containing a solid form of Compound 1 in the range of 0.005% to 100% with the balance made up from non toxic carrier may be prepared.

The compositions may include other active compounds to obtain desired combinations of properties. The solid forms of Compound 1 provided herein may also be advantageously administered for therapeutic or prophylactic purposes together with another pharmacological agent known in the general art to be of value in treating one or more of the diseases or medical conditions referred to hereinabove, such as diseases related to oxidative stress. It is to be understood that such combination therapy constitutes a further aspect of the compositions and methods of treatment provided herein.

Further encompassed are anhydrous pharmaceutical compositions and dosage forms containing a solid form of Compound 1 provided herein. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2 d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials).

6.5.1. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow release or sustained release system, such that a constant level of dosage is maintained is also contemplated herein. Briefly, a solid form of Compound 1 provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing a solid form of Compound 1 is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, such as more than 1% w/w of a solid forms of Compound 1 to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

A solid form of Compound 1 may be suspended in micronized or other suitable form or may be derivatized to produce a more soluble active product or to produce a prodrug. The form of the resulting mixture depends upon a number of factors, including the intended mode of administration and the solubility of the solid form of Compound 1 in the selected carrier or vehicle. The effective concentration is sufficient for ameliorating the symptoms of the condition and may be empirically determined.

6.5.2. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a solid form of Compound 1 provided herein in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (including but not limited to 1-1000 mg or 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 0.1-50 mg, about 0.5-50 mg, about 1 to 50 mg, about 5-35 mg, or about 9-30 mg of lyophilized powder, is added per mL of sterile water or other suitable carrier. In one embodiment, about 0.5 mg of lyophilized powder is added per mL of sterile water or other suitable carrier.

Exemplary lyophilized formulations comprising the solid forms provided herein (e.g., Form A, Form B, Form C, Form D, Form E and/or amorphous of Compound 1) are described in a U.S. provisional patent application filed concurrently herewith entitled "FORMULATIONS OF 3-(5-AMINO-2-METHYL-4-OXO-4H-QUINAZOLIN-3-YL)-PIPERIDINE-2,6-DIONE", the disclosure of which is incorporated herein by reference in its entirety.

6.5.3. Topical Administration

Topical mixtures are prepared as described for the local and systemic administration. The resulting mixture may be a solution, suspension, emulsion or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The solid forms of Compound 1 thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will have diameters of less than 50 microns or less than 10 microns.

The solid forms of Compound 1 may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the solid forms of Compound 1 alone or in combination with other pharmaceutically acceptable excipients can also be administered.

These solutions, particularly those intended for ophthalmic use, may be formulated as 0.01%-10% isotonic solutions, pH about 5-7, with appropriate salts.

6.5.4. Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin gelatin, carbowax (polyoxyethylene glycol) and appropriate mixtures of mono, di and triglycerides of fatty acids. Combinations of the various bases may be used. Agents to raise the melting point of suppositories include spermaceti and wax. Rectal suppositories may be prepared either by the compressed method or by molding. An exemplary weight of a rectal suppository is about 2 to 3 grams.

6.5.5. Sustained Release Compositions

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500 and 6,740,634, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. In one embodiment, the use of an optimally designed controlled-release preparation in medical treatment is characterized by a minimum of drug substance being employed to cure or control the condition in a minimum amount of time. In certain embodiments, advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or solid forms of Compound 1.

In certain embodiments, the agent may be administered using intravenous infusion, an implantable osmotic pump, a transdermal patch, liposomes, or other modes of administration. In one embodiment, a pump may be used (see, Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity of the therapeutic target, i.e., thus requiring only a fraction of the systemic dose (see, e.g., Goodson, Medical Applications of Controlled Release, vol. 2, pp. 115-138 (1984).

In some embodiments, a controlled release device is introduced into a subject in proximity of the site of inappropriate immune activation or a tumor. Other controlled release systems are discussed in the review by Langer (Science 249:1527-1533 (1990). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

6.5.6. Targeted Formulations

The solid forms of Compound 1 provided herein may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a solid form of Compound 1 provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

6.5.7. Articles of Manufacture

The solid forms of Compound 1 provided herein which is used for treatment, prevention or amelioration of one or more symptoms or progression of cancer, including solid tumors and blood borne tumors, and a label that indicates that the solid form of Compound 1 is used for treatment, prevention or amelioration of one or more symptoms or progression of cancer, including solid tumors and blood borne tumors.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, pens, bottles, and any packaging material suitable for a selected formulation and intended mode of administration and treatment. A wide array of formulations of the compounds and compositions provided herein are contemplated.

6.6. Evaluation of Activity

Standard physiological, pharmacological and biochemical procedures are available for testing the compounds to identify those that possess the desired anti-proliferative activity.

Such assays include, for example, biochemical assays such as binding assays, radioactivity incorporation assays, as well as a variety of cell based assays, including KG-1 cell proliferation assay described in the Example section.

7. Examples

The following Examples are presented by way of illustration, not limitation. The following abbreviations are used in descriptions and examples:
BuOH Butanol
DCM: Dichloromethane
DMSO: Dimethylsulfoxide
DSC: Differential Scanning calorimetry
DVS Dynamic vapor sorption
EDTA: Ethylenediamine tetraacetate
EtOH: Ethanol
EtOAc Ethyl acetate
HPLC: High performance liquid chromatography
IPA: 2-Propanol
KF Karl Fisher
LCMS: Liquid Chromatography with Mass Spectroscopy
MeCN Acetonitrile
MeOAc: Methylacetate
MeOH: Methanol
MEK: Methyl ethyl ketone
MIBK: Methyl isobutyl ketone
MTBE Methyl t-butyl ether
NMP: N-Methyl-2-pyrrolidone
NMR: Nuclear magnetic resonance
RH: Relative Humidity
RT: Room Temperature
SEM Scanning Electron Microscope °
TA: Thermal Analysis
TGA: Thermogravimetric Analysis
TGA-MS/TG-MS: Thermogravimetric Analysis coupled with Mass Spectroscopy
THF: Tetrahydrofuran
TLC: Thin layer chromatography
XRPD: X-Ray Powder Diffraction

7.1 Solid Forms

7.1.1 Polymorph Screen

A polymorph screen of Compound 1 was performed to investigate whether different solid forms could be generated under various conditions, such as different solvents, temperature and humidity changes.

The solvents used in the polymorph screen were either HPLC or reagent grade, including acetone, acetonitrile (MeCN), MeCN/water (1:1), n-butanol (n-BuOH), absolute ethanol (EtOH), ethanol/water (1:1), methanol (MeOH), 2-propanol (IPA), ethyl acetate (EtOAc), methyl acetate (MeOAc), dichloromethane (DCM), methyl ethyl ketone (MEK), methyl t-butyl ether (MTBE), heptane, toluene, tetrahydrofuran (THF), THF/water (1:1), water, dimethyl sufoxide (DMSO), and N-methylpyrrolidone (NMP).

The characterization of the crystal forms produced during the screen was performed by X-ray powder diffraction (XRPD), differential scanning calorimetry (DSC), thermogravimetric analysis (TGA), Miniature Scanning Electron Microscope (Mini SEM) and dynamic vapor sorption (DVS), Karl Fischer (KF), and/or $^1$H-Nuclear Magnetic Resonance (NMR).

XRPD analysis was conducted on a PANalytical Empyrean X-ray powder diffractometer using Cu Kα radiation at 1.54 Å. The PANalytical Empyrean instrument was equipped with a fine focus X-ray tube. The voltage and amperage of the X-ray generator were set at 45 kV and 40 mA, respectively. The divergence slits were set at ¹⁄₁₆° and ⅛°, and the receiving slits was set at ¹⁄₁₆°. Diffracted radiation was measured using a Pixel 2D detector. A theta-two theta continuous scan was set at step size 0.013 or 0.026 from 3° to 40° 2θ with sample spinning rate at 4. A sintered alumina standard was used to check the peak positions.

XRPD data were obtained on a PANalytical Empyrean X-ray powder diffractometer using similar instrument parameters.

DSC analyses were performed on a TA Discovery Differential Scanning calorimeter. Indium was used as the calibration standard. Approximately 1-5 mg of sample was placed into a DSC pan. The sample was heated under nitrogen at a rate of 10° C./min, up to a final temperature of 300° C. Melting points were reported as the extrapolated onset temperatures.

TGA analyses were performed on a TA Discovery Thermogravimetric Analyzer. Calcium oxalate was used for a performance check. Approximately 2-10 mg of accurately weighed sample was placed on a pan and loaded into the TGA furnace. The sample was heated under nitrogen at a rate of 10° C./min, up to a final temperature of 300° C.

TGA/SDTA analyses were performed on a TGA/SDTA851e instrument (Mettler-Toledo GmbH, Switzerland). The TGA/SDTA851e instrument was calibrated for temperature with indium and aluminium. Samples were weighed into 100 μl aluminium crucibles and sealed. The seals were pin-holed and the crucibles heated in the TGA from 25 to 300° C. at a heating rate of 10° C./min. Dry N2 gas was used for purging. The TGA data were obtained on a TA Q500 TGA instrument. The samples were heated at a rate of 10° C./min using nitrogen as the purge gas.

Morphology analysis of the samples was carried out on an Evex Mini SEM. Small amounts of samples were dispersed on a sample holder, and then coating with gold and viewed with 500× to 1000× magnification.

Hygroscopicity was determined on a Surface Measurement Systems DVS. Typically a sample size of 5-20 mg was loaded into the DVS instrument sample pan and the sample was analyzed on a DVS automated sorption analyzer at room temperature. The relative humidity was increased from 0% to 90% RH at 10% RH step, then decreased in a similar manner to accomplish a full adsorption/desorption cycle.

$^1$H NMR spectra were obtained on a Bruker 300 MHz NMR spectrometer. Samples were dissolved in DMSO-d6 and analyzed with 8-64 scans.

Solubility of Form C in selected aqueous and organic solvents was determined by mixing solid with solvents at room temperature. The solubility samples were filtered after 24 hr of agitation and quantified by an HPLC method, except for MeOH in which the solubility was determined after agitating 2 hr in order to minimize degradation.

Water content was measured using a coulometric KF titrator equipped with an oven sample processor. The oven temperature was set as 225° C.

7.1.2 Experiments and Methods

7.1.2.1 Solubility

In order to select the screening solvents and to determine the concentration range to be used in the screen, a quantitative solubility assessment was performed on Form B and Form C of Compound 1. Approximate solubility of Compound 1 Form B and solubility of Form C by HPLC at room temperature are provided in Tables 1 and 2, respectively.

TABLE 1

Approximate Solubility of Compound 1 Form B at Room Temperature.

| Solvent | Approximate Solubility (mg/mL) |
|---|---|
| Acetone | <6 |
| MeCN | <3 |
| MeCN/water (1:1) | <3 |
| n-BuOH | <2 |
| EtOH | <2 |
| EtOH/water (1:1) | <2 |
| MeOH | <15* |
| IPA | <1 |
| EtOAc | <2 |
| MEK | <3 |
| DCM | <1 |
| MTBE | <1 |
| Heptane | <1 |
| Toluene | <1 |
| THF | <12 |
| THF/water (1:1) | <10 |
| Water | <1 |
| MeOAc | <3 |
| NMP | >100 |
| DMSO | >100 |

*degradation suspected.

TABLE 2

HPLC Solubility of Form C in Selected Solvents at Room Temperature.

| Solvent | Solubility (mg/mL) |
|---|---|
| Water | 0.001 |
| 0.9% NaCl | 0.001 |
| 0.1N HCl | 0.001 |
| Acetate buffer pH 4.0 | 0.001 |
| Phosphate buffer pH 6.8 | 0.001 |
| MeCN | 1.179 |
| Acetone | 2.354 |
| MeOH | 0.843 |
| EtOH | 0.235 |
| IPA | 0.071 |
| EtOAc | 0.285 |
| THF | 4.349 |
| Heptane | <0.0001 |
| Toluene | 0.002 |
| DMSO | >200 |

7.1.2.2 Equilibration and Evaporation

Equilibration and evaporation experiments were performed at room temperature and 50° C. using Compound 1 Form B as starting material. An excess of Compound 1 Form B was added to up to 2 mL of a test solvent. The resulting mixture was agitated for 4 days at room temperature and for about 18 hours at 50° C. separately. Upon reaching equilibrium, the saturated supernatant solution was removed, filtered using 0.45 μm PTFE filters and allowed to evaporate in an open vial under nitrogen at room temperature and 50° C., respectively. The solid resulting from the equilibration was isolated and air-dried before analysis. The results are summarized in Table 3.

TABLE 3

Summary of Equilibration and Evaporation Results.

| Solvent | Form by XRPD | | | |
|---|---|---|---|---|
|  | EQ at RT | EV at RT | EQ at 50° C. | EV at 50° C. |
| Acetone | B | — | A | — |
| MeCN | B | — | A | — |
| MeCN/water | B | — | C | — |
| n-BuOH | B | — | B (+A) | — |
| EtOH | B | — | A | — |
| EtOH/water | B | — | C | — |
| MeOH | B + A | amorphous* | — | amorphous* |
| IPA | B | — | B + A | — |
| EtOAc | B | — | B + A | — |
| MEK | B + A | — | A | — |
| DCM | B | — | n/a | — |
| MTBE | B + A | — | n/a | — |
| Heptane | B | — | B | — |
| Toluene | B | — | B | — |
| THF | B + A | B | A + B | B |
| THF/water | B + A | B | B + A | B |
| water | B | — | B | — |
| MeOAc | B | — | A | — | n/a: no experiment
—: not analyzable.
*significant degradation occurred.

Equilibration in MeCN/water and EtOH/water at 50° C. afforded Compound 1 Form C. Equilibration in EtOH, MEK, and MeOAc at 50° C. afforded Form A. All other equilibration experiments afforded Form B or Form B mixed with Form A or Form C. Due to relatively low solubility, most evaporation experiments didn't afford analyzable solid. Evaporation from THF and THF/water afforded Form B. Solids from MeOH evaporation showed amorphous XRPD patterns, but $^1$H NMR spectrum of the solid showed significant degradation.

7.1.2.2 Cooling Recrystallization

Cooling recrystallization experiments were performed as described in Section 4.3. The solvents included MeOH/water (1:1), THF/water (1:1), and THF. The results are summarized in Table 4. The solids obtained from THF/water was confirmed to be Form B. A small amount of solid was obtained from MeOH/water, but showed a diffuse XRPD pattern from which the solid form can't be identified. Precipitation was not observed from the THF recrystallization experiment.

TABLE 4

Results from Cooling Recrystallization

| Solvent | Cooling Profile | Form by XRPD |
|---|---|---|
| MeOH/water (1:1) | 70 to −15° C. | ? (few peaks) |
| THF/water (1:1) | 70 to −15° C. | B |
| THF | 70 to −15° C. | — |

— no precipitation

7.1.2.3 Recrystallizations with Anti-Solvents

Recrystallizations with anti-solvents were performed as described in Section 4.3. MeOH and DMSO were used as primary solvents. MeCN, acetone, heptane, EtOAc, toluene, water, and IPA were used as anti-solvents. The results are summarized in Table 5. Precipitation was observed only from a few solvent systems, including MeOH/water, DMSO/IPA, DMSO/toluene, and DMSO/water, and all solids were confirmed to be Form B.

| Primary solvent | Anti-Solvent | Solvent Ratio | Cooling profile | Form by XRPD |
|---|---|---|---|---|
| MeOH | MeCN | 1:15 | 50 to 4° C. | — |
| MeOH | acetone | 1:15 | 50 to 4° C. | — |
| MeOH | heptane | 1:15 | 50 to 4° C. | — |
| MeOH | EtOAc | 1:15 | 50 to 4° C. | — |
| MeOH | toluene | 1:15 | 50 to 4° C. | — |
| MeOH | water | 1:15 | 50 to 4° C. | B |
| DMSO | acetone | 1:15 | RT to 4° C. | — |
| DMSO | MeCN | 1:15 | RT to 4° C. | — |
| DMSO | IPA | 1:15 | RT to 4° C. | B |
| DMSO | heptane | 1:15 | RT to 4° C. | — |
| DMSO | toluene | 1:15 | RT to 4° C. | B |
| DMSO | water | 1:15 | RT to 4° C. | B |

RT: room temperature
—: no precipitation

7.1.2.4 Slurry and Recrystallizations

Additional experiments were performed to generated materials for further characterization, as detailed in Table 6.

TABLE 6

Experiments to Generate Materials for Characterization

| Solvent | Experimental Conditions | Form by XRPD |
|---|---|---|
| MeCN/water (1:1) | Slurry, shaking at 50° C. for 1 day | C |
| EtOH/water (1:1) | Slurry, shaking at 50° C. for 1 day | A |
| EtOH/water (1:1) | Slurry, shaking at 50° C. for 3 days | C |
| THF/water (1:1) | Cooling recrystallization from ~70° C. to RT (high concentration) | B |
| THF/water (1:1) | Cooling recrystallization from ~70° C. to RT (low concentration) | B |

7.1.2.5 Interconversion Among Solid Forms

Further form conversion experiments were performed to determine interconversion among solid forms. The results are summarized in Table 7.

TABLE 7

Summary of Form Transfer Experiments

| Starting Form(s) | Solvent/ Condition | Temperature/ Condition | Resulting Form(s) |
|---|---|---|---|
| A + B + C | slurry in acetone | RT, 3 days | C |
| A + C | slurry in EtOH/water (1:1) | RT, 1 day | C |
| B + unknown A/C mix | slurry in acetone | 50° C., 1 day | C |
| B + unknown A/C mix | slurry in acetone | RT, 1 day | A |
| B + unknown A/C mix | slurry in heptane | 50° C., 3 days | A + B |
| B + unknown A/C mix | slurry in heptane | RT, 4 days | A + B |
| B + unknown A/C mix | slurry in IPA | 50° C., 2 days | A |
| B + unknown A/C mix | slurry in IPA | RT, 2 days | A + C + B? |
| B + unknown A/C mix | slurry in IPA/water | RT, 4 days | A |
| B + unknown A/C mix | slurry in IPA/water (2:1) | RT, 4 days | A |
| B + unknown A/C mix | slurry in IPA/water (3:1) | RT, 4 days | A |
| B + unknown A/C mix | slurry in IPA/water (5:1) | RT, 4 days | A |
| A | heating | 225° C., ~10 min in KF oven | A |
| B | heating | 160° C., 1 min | B |
| B | heating | 225° C., ~10 min in KF oven | A |
| C | heating | 225° C., ~10 min in KF oven | C |

RT: room temperature

7.1.2.6 Characterization of Polymorphic Forms

Figure 1:
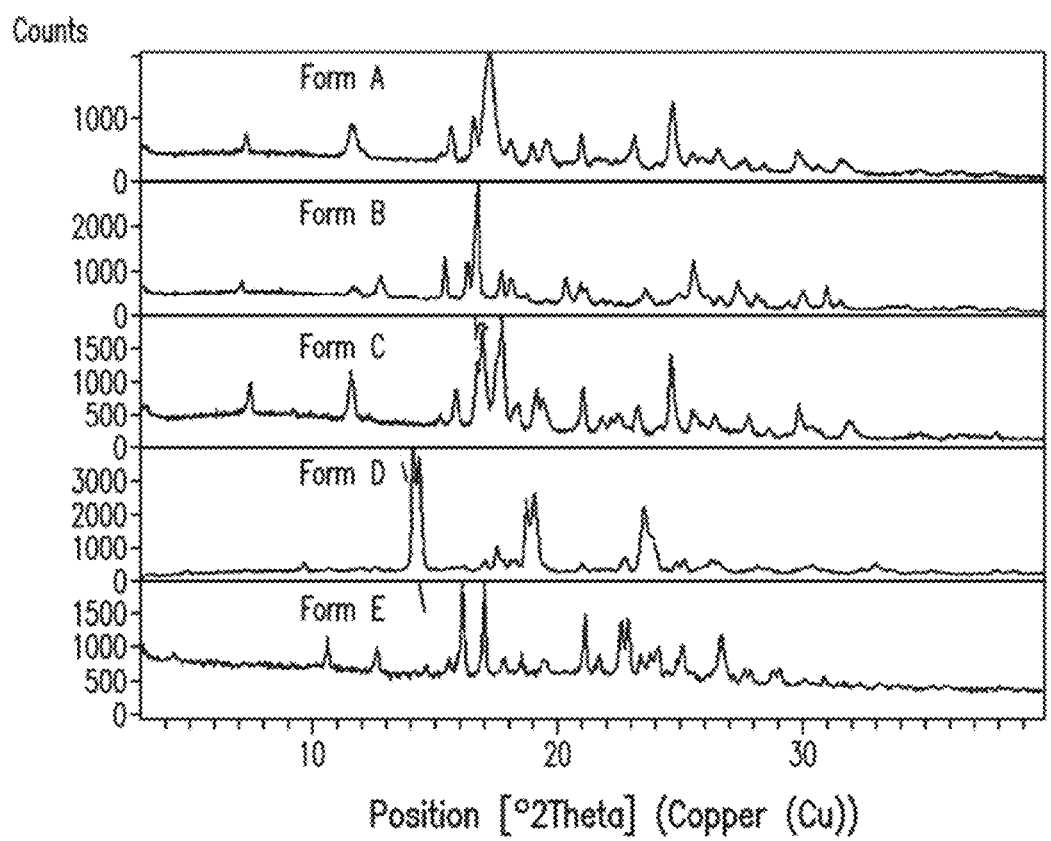
FIG. 1 depicts an X-ray powder diffractogram stack plot of Forms A, B, C, D, and E of Compound 1.

A total of 5 crystalline forms of Compound 1 were found during this polymorph screen study. The stack plot of XRPD patterns for these forms are shown in FIG. 1, and the physical characteristics are summarized in Table 8.

TABLE 8

Summary of Characterization Data for Compound 1 Polymorphs

| Form | Description | Representative conditions | DSC peak (° C.) | TGA loss (wt %) | DVS or other comments |
|---|---|---|---|---|---|
| A | anhydrate | intermediate form in slurries | 229 (onset, $\Delta H_f$ = 118 J/g) | 0 | ~1.2 wt % water uptake up to 90% RH; KF: <0.1 wt % |
| B | anhydrate | Anti-solvent recrystallizations | 219 (onset), 224 (exo peak), 231 (peak) | 0.4 (170~230° C.) | ~1.4 wt % water uptake up to 90% RH; KF: <0.1 wt % |
| C | anhydrate | EQ at 50° C. in MeCN/water, acetone, or EtOH/water | 232 (onset, $\Delta H_f$ = 126 J/g) | 0 | ~0.6 wt % water uptake up to 90% RH; KF: <0.1 wt % |
| D | solvate | recrystallization in DMSO/MIBK; slurry in DMSO/anisole | n/a | 14.1 | 14.3% DMSO (by gas chromatography) |
| E | solvate | slurry in DMSO/MIBK, DMSO/Anisole or DMSO/IPA | n/a | 19.4 (up to 120° C.), 24.9 (120~220° C.) | n/a | n/a: not available.

Form A

The XRPD pattern, TGA, DSC, DVS, $^1$H NMR, stability profile upon compression and SEM of Form A of Compound 1 are shown in FIGS. 2-8.

FIG. 2 provides an XRPD pattern of Form A of Compound 1. A list of X-Ray Diffraction Peaks for Form A of Compound 1 is provided below in Table 9.

TABLE 9

X-Ray Diffraction Peaks for Form A of Compound 1

| No. | Pos. [°2Th.] | d-spacing [Å] | Rel. Int. [%] |
|---|---|---|---|
| 1 | 7.23 | 12.2187 | 17.6 |
| 2 | 11.52 | 7.6789 | 29.7 |
| 3 | 15.22 | 5.8209 | 7.5 |
| 4 | 15.62 | 5.6720 | 31.2 |
| 5 | 16.58 | 5.3466 | 40.3 |
| 6 | 17.19 | 5.1576 | 100.0 |
| 7 | 18.08 | 4.9056 | 22.3 |
| 8 | 19.00 | 4.6702 | 19.6 |
| 9 | 19.60 | 4.5302 | 22.1 |
| 10 | 21.05 | 4.2197 | 29.2 |
| 11 | 21.74 | 4.0884 | 8.3 |
| 12 | 22.01 | 4.0388 | 7.1 |
| 13 | 22.47 | 3.9576 | 6.0 |
| 14 | 23.22 | 3.8312 | 28.6 |
| 15 | 24.17 | 3.6825 | 5.6 |
| 16 | 24.77 | 3.5945 | 57.2 |
| 17 | 25.59 | 3.4813 | 14.6 |
| 18 | 25.94 | 3.4356 | 10.5 |
| 19 | 26.63 | 3.3470 | 17.4 |
| 20 | 27.73 | 3.2172 | 10.0 |
| 21 | 28.51 | 3.1307 | 7.1 |
| 22 | 29.88 | 2.9906 | 19.3 |
| 23 | 30.76 | 2.9065 | 7.1 |
| 24 | 31.59 | 2.8327 | 11.1 |
| 25 | 34.82 | 2.5766 | 4.8 |
| 26 | 36.05 | 2.4913 | 4.3 |

No TGA weight loss was observed for Form A as depicted in FIG. 3.

A DSC plot for Form A showed a melting event with an onset temperature of 229° C. and heat of fusion of 118 J/g as depicted in FIG. 4.

A dynamic vapor sorption (DVS) isotherm plot for Form A is shown in FIG. 5. When the relative humidity ("RH") was increased from about 0% to about 90% RH, Form A exhibited about 1.2% w/w water uptake. Form A contained less than 0.1% water as determined in a coulometric Karl Fischer (KF) titrator equipped with an oven sample processor set at 225° C.

No significant degradation or residual solvent for Form A was observed by $^1$H NMR as depicted in FIG. 6.

XRPD pattern for Form A remained substantially unchanged with broader diffraction peaks, upon application of 2000-psi pressure for about 1 minute as shown in FIG. 7. The SEM picture of Form A is shown in FIG. 8.

Form B

Form B was generated by various anti-solvent recrystallization experiments, including MeOH/water, DMSO/IPA, DMSO/toluene, and DMSO/water. Cooling recrystallization from THF/water 1:1 also afforded Form B. The XRPD pattern, SEM, TGA, DSC, DVS, $^1$H NMR, and stability profile upon compression of Form B of Compound 1 are shown in FIGS. 9-15.

FIG. 9 provides an XRPD pattern of Form B of Compound 1. A list of X-Ray Diffraction Peaks for Form B of Compound 1 is provided below in Table 10.

TABLE 10

X-Ray Diffraction Peaks for Form B of Compound 1

| No. | Pos. [°2Th.] | d-spacing [Å] | Rel. Int. [%] |
|---|---|---|---|
| 1 | 7.01 | 12.6035 | 9.3 |
| 2 | 11.58 | 7.6444 | 8.3 |
| 3 | 11.80 | 7.5027 | 6.8 |
| 4 | 12.73 | 6.9551 | 18.4 |
| 5 | 15.38 | 5.7601 | 34.8 |
| 6 | 16.32 | 5.4330 | 31.4 |
| 7 | 16.72 | 5.3012 | 100.0 |
| 8 | 17.72 | 5.0046 | 26.6 |
| 9 | 18.13 | 4.8930 | 19.8 |
| 10 | 18.77 | 4.7271 | 7.5 |
| 11 | 20.41 | 4.3516 | 22.0 |
| 12 | 21.02 | 4.2258 | 15.9 |
| 13 | 21.21 | 4.1881 | 13.5 |
| 14 | 21.93 | 4.0529 | 3.4 |
| 15 | 23.68 | 3.7581 | 14.2 |
| 16 | 25.01 | 3.5601 | 10.4 |
| 17 | 25.63 | 3.4755 | 37.3 |
| 18 | 26.19 | 3.4030 | 9.8 |
| 19 | 26.73 | 3.3349 | 8.5 |
| 20 | 27.45 | 3.2499 | 20.9 |
| 21 | 27.71 | 3.2193 | 9.4 |
| 22 | 28.22 | 3.1623 | 11.8 |
| 23 | 29.48 | 3.0296 | 4.7 |
| 24 | 30.10 | 2.9692 | 15.0 |
| 25 | 31.08 | 2.8775 | 18.3 |
| 26 | 31.65 | 2.8272 | 6.2 |
| 27 | 34.29 | 2.6150 | 3.4 |

The SEM picture of Form B is shown in FIG. 10.

No TGA weight loss below 170° C. was observed for Form B. A TGA weight loss of 0.4% was observed between 170-230° C. as depicted in FIG. 11.

A DSC plot for Form B showed a melt/recrystallization event at 219~224° C. and a major melting event with a peak temperature of 231° C. as depicted in FIG. 12.

A dynamic vapor sorption (DVS) isotherm plot for Form B is shown in FIG. 13. When the relative humidity ("RH") was increased from about 0% to about 90% RH, Form B exhibited about 1.4% w/w water uptake. Form B contained less than 0.1% water as determined in a coulometric Karl Fischer (KF) titrator equipped with an oven sample processor set at 225° C.

No significant degradation or residual solvent for Form B was observed by $^1$H NMR as depicted in FIG. 14.

XRPD pattern for Form B remained substantially unchanged with broader diffraction peaks, upon application of 2000-psi pressure for about 1 minute as shown in FIG. 15.

Form C

Form C was generated by slurrying in solvent systems containing one or more of the following solvents: acetonitrile/water, acetone, or ethanol/water for extended period of time. Form B, (1×wt) was stirred in acetone (30×vol) at 70-75° C. under nitrogen pressure of 50-55-psi. The batch was agitated for at least 24 h. The mixture was cooled to room temperature over at least 6 hours. At the end of this period, the batch was filtered. The cake was washed with acetone (2.3×vol) and dried under vacuum. The solids were co-milled. This afforded a white to off-white solid, which is consistent with Form C with expected yield of 85 to 90% and expected LC purity of no less than 98.5% area. The XRPD pattern, SEM, TGA, DSC, DVS, $^1$H NMR, and stability profile upon compression of Form C of Compound 1 are shown in FIGS. 16-22.

FIG. 16 provides an XRPD pattern of Form C of Compound 1. A list of X-Ray Diffraction Peaks for Form C of Compound 1 is provided below in Table 11.

TABLE 11

X-Ray Diffraction Peaks for Form C of Compound 1

| No. | Pos. [°2Th.] | d-spacing [Å] | Rel. Int. [%] |
|---|---|---|---|
| 1 | 7.36 | 12.0091 | 32.0 |
| 2 | 9.14 | 9.6750 | 8.3 |
| 3 | 11.51 | 7.6855 | 44.7 |
| 4 | 12.22 | 7.2420 | 4.9 |
| 5 | 15.17 | 5.8398 | 8.4 |
| 6 | 15.82 | 5.6011 | 31.8 |
| 7 | 16.68 | 5.3140 | 57.1 |
| 8 | 16.92 | 5.2392 | 86.8 |
| 9 | 17.72 | 5.0057 | 100.0 |
| 10 | 18.39 | 4.8242 | 21.9 |
| 11 | 19.18 | 4.6268 | 36.4 |
| 12 | 19.45 | 4.5649 | 27.1 |
| 13 | 21.11 | 4.2077 | 40.4 |
| 14 | 21.82 | 4.0724 | 12.4 |
| 15 | 22.28 | 3.9902 | 12.0 |
| 16 | 22.57 | 3.9398 | 17.6 |
| 17 | 23.36 | 3.8082 | 24.7 |
| 18 | 24.26 | 3.6695 | 7.1 |
| 19 | 24.71 | 3.6026 | 72.5 |
| 20 | 25.74 | 3.4615 | 16.9 |
| 21 | 26.03 | 3.4231 | 9.7 |
| 22 | 26.51 | 3.3627 | 17.7 |
| 23 | 27.88 | 3.1998 | 18.0 |
| 24 | 28.70 | 3.1104 | 6.9 |
| 25 | 29.91 | 2.9871 | 30.5 |
| 26 | 30.43 | 2.9375 | 10.7 |
| 27 | 30.83 | 2.9006 | 5.8 |
| 28 | 32.01 | 2.7960 | 16.6 |
| 29 | 37.94 | 2.3718 | 5.5 |

The SEM picture of Form C is shown in FIG. 17.

No TGA weight loss was observed for Form C.

A DSC plot for Form C showed a melting event with an onset temperature of 232° C. and heat of fusion of 126 J/g as depicted in FIG. 18.

A dynamic vapor sorption (DVS) isotherm plot for Form C is shown in FIG. 20. When the relative humidity ("RH")

was increased from about 0% to about 90% RH, Form C exhibited about 0.6% w/w water uptake. Form C contained less than 0.1% water as determined in a coulometric Karl Fischer (KF) titrator equipped with an oven sample processor set at 225° C.

No significant degradation or residual solvent for Form C was observed by $^1$H NMR as depicted in FIG. 21.

XRPD pattern for Form C remained substantially unchanged with broader diffraction peaks, upon application of 2000-psi pressure for about 1 minute as shown in FIG. 22.

Form D

Form D of Compound 1 is a DMSO solvate.

Form D was obtained by 1) adding about 1.0 g of Form B to a 100-mL crystallizer, 2) heating Form B to about 70° C., 3) adding about 10 mL of DMSO/methyl isobutyl ketone (MIBK) (1:2, v/v), 4) adding about 3.8 mL of MIBK to solution over about 20 min, 5) adding about 100 mg of Form C to the solution, and stirring at about 400 rpm for one day, 6) cooling the batch to about 20° C. for about 5 h, 0.17° C./min, 7) stirring at about 20° C. over night, 8) filtering and washing wet cake with about 2 mL MIBK, and drying under vacuum at about 45° C.

The XRPD pattern and TGA of Form D of Compound 1 are shown in FIGS. 23-24, respectively.

FIG. 23 provides an XRPD pattern of Form D of Compound 1. A list of X-Ray Diffraction Peaks for Form D of Compound 1 is provided below in Table 12.

TABLE 12

X-Ray Diffraction Peaks for Form D of Compound 1

| No. | Pos. [°2Th.] | d-spacing [Å] | Rel. Int. [%] |
|---|---|---|---|
| 1 | 4.77 | 18.5435 | 3.0 |
| 2 | 9.57 | 9.2399 | 7.0 |
| 3 | 10.55 | 8.3876 | 3.1 |
| 4 | 11.95 | 7.4070 | 3.7 |
| 5 | 12.50 | 7.0808 | 3.5 |
| 6 | 14.06 | 6.2990 | 100.0 |
| 7 | 14.30 | 6.1927 | 92.9 |
| 8 | 16.13 | 5.4943 | 3.8 |
| 9 | 17.02 | 5.2097 | 8.4 |
| 10 | 17.50 | 5.0676 | 19.8 |
| 11 | 17.78 | 4.9881 | 8.0 |
| 12 | 18.09 | 4.9049 | 7.7 |
| 13 | 18.27 | 4.8561 | 9.0 |
| 14 | 18.75 | 4.7326 | 58.5 |
| 15 | 19.09 | 4.6482 | 63.5 |
| 16 | 21.04 | 4.2228 | 7.3 |
| 17 | 22.77 | 3.9053 | 10.9 |
| 18 | 23.58 | 3.7738 | 53.6 |
| 19 | 24.02 | 3.7045 | 24.6 |
| 20 | 24.90 | 3.5756 | 8.4 |
| 21 | 25.22 | 3.5310 | 10.0 |
| 22 | 26.37 | 3.3796 | 9.4 |
| 23 | 26.63 | 3.3470 | 7.9 |
| 24 | 28.21 | 3.1640 | 5.8 |
| 25 | 29.82 | 2.9958 | 3.0 |
| 26 | 30.16 | 2.9629 | 5.0 |
| 27 | 30.45 | 2.9361 | 6.7 |
| 28 | 32.48 | 2.7566 | 3.3 |
| 29 | 33.03 | 2.7120 | 8.1 |
| 30 | 33.69 | 2.6604 | 3.4 |
| 31 | 35.32 | 2.5413 | 3.0 |
| 32 | 37.96 | 2.3702 | 3.2 |
| 33 | 38.70 | 2.3269 | 3.0 |

A TGA weight loss of about 14.1% up to 140° C. was observed for Form D as depicted in FIG. 24.

Form E

Form E of Compound 1 is a DMSO solvate.

Form E was obtained by 1) adding 200 mg of Form C in to a 3-mL glass vial, 2) adding 0.5 mL of DMSO/MIBK (1:2, v/v) or DMSO/IPA (2:1, v/v) solution, 3) optionally adding Form E seed, 4) stirring at room temperature for one day, 5) filtering and washing wet cake with 2 mL MIBK or isopropanol, respectively.

The XRPD pattern and TGA of Form E of Compound 1 are shown in FIGS. 25-26, respectively.

FIG. 25 provides an XRPD pattern of Form E of Compound 1. A list of X-Ray Diffraction Peaks for Form E of Compound 1 is provided below in Table 13.

TABLE 13

X-Ray Diffraction Peaks for Form E of Compound 1

| No. | Pos. [°2Th.] | d-spacing [Å] | Rel. Int. [%] |
|---|---|---|---|
| 1 | 4.20 | 21.0329 | 9.6 |
| 2 | 10.48 | 8.4394 | 32.0 |
| 3 | 12.54 | 7.0591 | 28.4 |
| 4 | 14.52 | 6.1023 | 9.9 |
| 5 | 15.51 | 5.7131 | 17.7 |
| 6 | 16.08 | 5.5121 | 100.0 |
| 7 | 16.97 | 5.2256 | 94.5 |
| 8 | 17.77 | 4.9908 | 17.1 |
| 9 | 18.48 | 4.8001 | 20.5 |
| 10 | 19.54 | 4.5422 | 14.7 |
| 11 | 21.15 | 4.2007 | 62.8 |
| 12 | 21.72 | 4.0924 | 20.8 |
| 13 | 22.64 | 3.9270 | 57.4 |
| 14 | 22.91 | 3.8826 | 59.9 |
| 15 | 23.43 | 3.7977 | 23.6 |
| 16 | 23.83 | 3.7348 | 23.2 |
| 17 | 24.13 | 3.6881 | 29.5 |
| 18 | 25.14 | 3.5421 | 35.2 |
| 19 | 26.72 | 3.3362 | 49.5 |
| 20 | 27.68 | 3.2232 | 14.6 |
| 21 | 27.93 | 3.1949 | 15.3 |
| 22 | 28.86 | 3.0942 | 15.6 |
| 23 | 29.08 | 3.0703 | 18.3 |
| 24 | 30.12 | 2.9671 | 7.1 |
| 25 | 30.92 | 2.8923 | 12.8 |
| 26 | 32.35 | 2.7672 | 5.0 |
| 27 | 33.21 | 2.6979 | 6.9 |

A TGA weight loss of about 19.4% up to 120° C. was observed for Form E with an additional weight loss of 24.9% between 120 and 220° C. as depicted in FIG. 26.

Amorphous Form

An Amorphous Form of Compound 1 was obtained by 1) adding Compound 1 in THF and water to form a suspension; 2) heating the suspension to 35-45° C. to obtain a clear solution; 3) freezing the solution to in a cold bath of −78° C.; 4) applying high vacuum to remove the solvent, to obtain an amorphous form of Compound 1.

The DSC thermogram, XRPD pattern, and $^1$H NMR spectrum for Amorphous Form of Compound 1 are shown in FIGS. 27-29, respectively.

7.1.3 KG-1 Cell Proliferation Assay

The following is an example of an assay that can be used to determine the anti-proliferative activity of the solid forms of Compound 1 in KG-1 cell line (American Type Culture Collection [ATCC]: catalogue number ATCC® CCL-246™)

at 72 hours post-treatment. The seeding density for KG-1 can be optimized to ensure assay linearity in 384-well plates.

Increasing concentrations of the solid forms of Compound 1 (0.5 nM to 10 μM) are spotted in a 10-point serial dilution fashion (3-fold dilution) in duplicate via an acoustic dispenser (EDC ATS-100) into an empty 384-well plate. The dimethyl sulfoxide (DMSO) concentration is kept constant for a final assay concentration of 0.1% DMSO. Prior to testing, KG-1 cells are grown in RPMI-1640 (Roswell Park Memorial Institute-1640) medium with 10% FBS (fetal bovine serum: HyClone) and expanded in culture flasks to provide sufficient amounts of starting material. Cells are then diluted to 5000 cells per well, in a 50 μL volume and added directly to the compound-spotted 384-well plates. Cells are allowed to grow for 72 hours in 5% $CO_2$ at 37° C. At the time when exposure of cells to compound began (to), initial viable cell number is assessed via Cell Titer-Gb® Luminescent Cell Viability Assay at a 1 vol: 2 vol ratio according to manufacturer's instructions (Promega Corporation, Madison, Wis.) by quantifying the level of luminescence generated by adenosine-5'-triphosphate (ATP) present in viable cells. After 72 hours, cell viability of the treated cells is assessed via Cell Titer-Gb® and read for luminescence.

While the disclosure has been described with respect to the particular embodiments, it will be apparent to those skilled in the art that various changes and modifications may be made without departing from the spirit and scope of the disclosure as defined in the claims. Such modifications are also intended to fall within the scope of the appended claims.

All of the patents, patent applications and publications referred to herein are incorporated herein in their entireties. Citation or identification of any reference in this application is not an admission that such reference is available as prior art to this disclosure. The full scope of the disclosure is better understood with reference to the appended claims.

What is claimed is:

1. A solid form of 2-(4-chlorophenyl)-N-((2-(2,6-dioxopiperidin-3-yl)-1-oxoisoindolin-5-yl)methyl)-2,2-difluoroacetamide or a tautomer thereof:

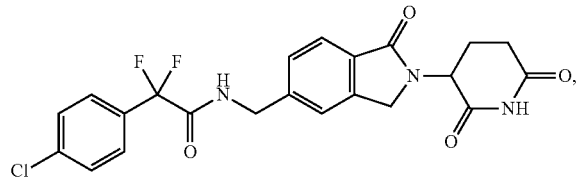 [SMILES: O=C1CCC(N2Cc3cc(CNC(=O)C(F)(F)c4ccc(Cl)cc4)ccc3C2=O)C(=O)N1]

wherein the solid form is

Form A having an X-ray powder diffraction pattern comprising peaks at about 15.6, 16.6, 17.2 or 24.8 degrees 2θ.

2. The solid form of claim 1, which is anhydrous.

3. The solid form of claim 1, which is Form A having an X-ray powder diffraction pattern comprising peaks at about 15.6, 16.6, 17.2 and 24.8 degrees 2θ.

4. The solid form of claim 1, having an X-ray powder diffraction pattern comprising peaks at about 11.5, 15.6, 16.6, 17.2, 18.1, 19.0, 19.6, 21.1, 23.2 or 24.8 degrees 2θ.

5. The solid form of claim 3, having an X-ray powder diffraction pattern substantially as shown in FIG. 2.

6. The solid form of claim 3, having a thermal gravimetric analysis plot substantially as shown in FIG. 3.

7. The solid form of claim 3, having a differential scanning calorimetry plot comprising an endothermic event with an onset temperature of about 229° C.

8. The solid form of claim 3, having a differential scanning calorimetry plot substantially as shown in FIG. 4.

9. The solid form of claim 3, which exhibits a mass increase of less than about 1.2% when subjected to an increase in relative humidity from about 0% to about 90% relative humidity.

10. The crystal form of claim 3, which is substantially pure.

* * * * *